United States Patent [19]
Spencer et al.

[11] Patent Number: 6,040,497
[45] Date of Patent: Mar. 21, 2000

[54] GLYPHOSATE RESISTANT MAIZE LINES

[75] Inventors: Michael Spencer, Mystic, Conn.; Rita Mumm, Tolono; Jeff Gwyn, Mahomet, both of Ill.

[73] Assignee: Dekalb Genetics Corporation, Dekalb, Ill.

[21] Appl. No.: 08/832,078

[22] Filed: Apr. 3, 1997

[51] Int. Cl.[7] ............................ C12N 15/00; C12N 15/82; A01H 10/06; A01H 4/00
[52] U.S. Cl. ........................ 800/288; 800/278; 800/300.1; 800/320.1; 800/275; 800/266; 536/24.1
[58] Field of Search ................................. 800/320.1, 275, 800/266, 300, 300.1, 288, 278; 435/412, 424, 430, 430.1; 536/24.1

[56] References Cited

U.S. PATENT DOCUMENTS

| | | | |
|---|---|---|---|
| 4,535,060 | 8/1985 | Comai | 435/172.3 |
| 4,761,373 | 8/1988 | Anderson et al. | 435/172.3 |
| 4,769,061 | 9/1988 | Comai | 71/86 |
| 4,940,835 | 7/1990 | Shah et al. | 800/205 |
| 4,971,908 | 11/1990 | Kishore et al. | 435/172.1 |
| 5,034,322 | 7/1991 | Rodgers et al. | 435/172.3 |
| 5,068,193 | 11/1991 | Comai | 435/252.3 |
| 5,094,945 | 3/1992 | Comai | 435/172.3 |
| 5,177,010 | 1/1993 | Goldman et al. | 435/172.3 |
| 5,188,642 | 2/1993 | Shah et al. | 47/58 |
| 5,436,389 | 7/1995 | Pfund | 800/200 |
| 5,484,956 | 1/1996 | Lundquist et al. | 800/205 |
| 5,554,798 | 9/1996 | Lundquist et al. | 800/205 |
| 5,641,664 | 6/1997 | D'Halluin et al. | 435/172.3 |
| 5,641,876 | 6/1997 | McElroy et al. | 536/24.1 |

FOREIGN PATENT DOCUMENTS

| | | |
|---|---|---|
| 0 242 236 | 1/1987 | European Pat. Off. . |
| 0 242 246 | 3/1987 | European Pat. Off. . |
| 0 218 571 | 4/1987 | European Pat. Off. . |
| 0 290 395 | 11/1988 | European Pat. Off. . |
| 0 348 348 | 6/1989 | European Pat. Off. . |
| 0 360 750 | 9/1989 | European Pat. Off. . |
| 0 353 908 | 2/1990 | European Pat. Off. . |
| 0 469 273 | 6/1991 | European Pat. Off. . |
| 2 661 421 | 4/1991 | France . |
| WO 87/05629 | 9/1987 | WIPO . |
| WO 91/02071 | 2/1991 | WIPO . |
| WO 91/09948 | 7/1991 | WIPO . |
| WO 91/10725 | 7/1991 | WIPO . |
| WO 92/04449 | 3/1992 | WIPO . |
| WO 97/4103 | 2/1997 | WIPO . |
| WO 97/23634 | 7/1997 | WIPO . |

OTHER PUBLICATIONS

Padgette et al. J. Bio. Chem. vol 266, No. 33, pp. 22364–22369, Nov. 1991.
McElroy et al., "Isolation of an Efficient Actin Promoter for Use in Rice Transformation," *The Plant Cell,* 2:163–171, 1990.
Padgette et al., "New Weed Control Opportunities: Development of Soybeans with a Roundup Ready™ Gene," In: *Herbicide–Resistant Crops,* Stephen O. Duke, Editor, Lewis Publishers, Boca Raton, Chapter 4, p. 53–84, 1996.
Amrhein et al., "Biochemical Basis for Glyphosate–Tolerance in a Bacterium and a Plant Tissue Culture," *FEBS,* 157)1):191–196, Jun. 1983.
Anderson, W. *Weed Science: Principles,* 2nd ed., West Publishing Company, St. Paul, pp. 13–15 (1983).
Ashton, F., et al. *Mode of Action of Herbicides,* John Wiley & Sons, New York, pp. vii–viii (1981).
Balthazor and Hallas, "Glyphosate–Degrading Microorganisms from Industrial Activated Sludge," *Applied and Environmental Microbiology,* 51(2):432–434, Feb. 1986.
Bishop, "Two Teams Place Genes Into Corn," The Wall Street Journal, Apr. 1990.
Chasan, "Transforming Maize Transformation," *The Plant Cell,* 4:1463–1464, Dec. 1992.
Christou, "Genetic Transformation of Crop Plants Using Microprojectile Bombardment," *The Plant Journal,* 2(3):275–281, 1992.
Christou, McCabe, and Swain, "Stable Transformation of Soybean Callus by DNA–Coated Gold Particles," *Plant Physiol.,* 87:671–674, 1988.
Clark, "Biotech Advance in Corn: Gunslinging Researchers Fire Marker Genes into Corn," *Ag Consultant,* p. 12, Jul. 1990.
Cocking and Davey, "Gene Transfer in Cereals," *Science,* 236:1259–1262, Jun. 1987.
Comai et al., "Expression in Plants of a Mutant aroA Gene from *Salmonella typhimurium* Confers Tolerance to Glyphosate," *Nature,* 317:741–744, Oct. 1985.
Comai, Sen and Stalker, "An Altered aroA Gene Product Confers Resistance to the Herbicide Glyphosate," *Science,* 221:370–371, Jul. 1983.
"Corn Plants Genetically Engineered to Express Wheat Germ Agglutinin (WGA) Genes, in Order to Confer Resistance to the European Corn Borer (*Ostrinia nubilalis*) and Tolerance to Glugosinate Herbicides," Pioneer's Application for Release Into the Environment Under 7 C.F.R. 340.
d'Amato et al., "Subcellular Localization of Chorismate–Mutase Isoenzymes in Protoplasts from Mesophyll and suspension–Cultured Cells of *Nicltiana silvestris,"* *Planta,* 162:104–108, 1984.
D'Halluin et al., "Transgenic Maize Plants by Tissue Electroporation," *The Plant Cell,* $:1495–1505, Dec. 1992.
De Block et al., "Engineering Herbicide Resistance in Plants by Expression of a Detoxifying Enzyme," *The EMBO Journal,* 6(9):2513–2518, 1987.
De Block, De Brouwer, and Tenning, "Transformation of *Brassica napus* and *Brassica oleracea* Using *Agrobacterium tumerfaciens* and the Expression of the bar and neo Genes in the Transgenic Plants," *Plant Physiol.,* 91:694–701, 1989.

(List continued on next page.)

*Primary Examiner*—Gary Benzion
*Attorney, Agent, or Firm*—Arnold, White & Durkee

[57] ABSTRACT

Methods and compositions relating to glyphosate resistant maize plants, including the GA21, GG25, GJ11 and FI117 transformation events, are disclosed. The plants of the invention represent a significant advance, in that they allow direct control of weeds in the field with glyphosate.

63 Claims, 21 Drawing Sheets

OTHER PUBLICATIONS

Evans, "Somaclonal Variation Genetic Basis and Breeding Applications," *Reviews*, 5(2):46–50, Feb. 1989.

Fishbein, Editor & Publisher, "Two Teams Succeed in Putting Foreign Genes in Corn Plants," *Genetic Engineering Letter*, 10(8):3, Apr. 1990.

Fransz, de Ruijter, and Schel, "Isoenzymes as Biochemical and Cytochemical Markers in Embryogenic Callus of Maize (*Zea mays* L.)," *Plant Cell Reports*, 8:67–70, 1989.

Fromm, "Gene Guns Succeed in Altering Corn," *Biotechnology News*, 10(11):2–3, Apr. 1990.

Fromm, "Inheritance and Expression of Chimeric Genes in the Progeny of Transgenic maize Plants," Bio/Technology, 8:833–839, Sep. 1990.

"Genetically Engineered Corn: Breakthrough Brings Market Closer," *Genetic Technology News*, p. 8 and 11, Oct. 1990.

"Genetic Engineering Advance Announced For Corn Plants," *Investor's Daily*, Apr. 19, 1990.

Goodman, et al., "Gene Transfer in Crop Improvements," *Science*, 236:48–54, Apr. 1987.

Gordon–Kamm et al., "Transformation of Maize Cells and Regeneration of Fertile Transgenic Plants," *The Plant Cell*, 2:603–618, Jul. 1990.

Guilley et al., "Transcription of Cauliflower Mosaic Virus DNA; Detection of Promoter Sequences, and Characterization of Transcripts," *Cell*, 30:763–773, Oct. 1982.

Gunset, "Corn Farmers Sell Economic, Environmental Gold in Designer Genes," Chicago Tribune, p. 1, Jan. 21, 1991.

Gunset, "Genetic Advance May Transform Corn," Chicago Tribune, Apr. 19, 1990.

Hallas, Hahn and Korndorfer, "Characterization of Microbial Traits Associated with Glyphosate Biodegradation in Industrial Activated Sludge," *Journal of Industrial Microbiology*, 3:377–385, 1988.

Howe, "Development of Glyphosate as a Selectable Marker for the Production of Fertile Transgenic Corn Plants," *In Vitro Cellular & Developmental Biology*, p. 124A, P–1136.

Jacob et al., "Metabolism of Glyphosate in Pseudomonas sp. Stran Lbr," *Applied and Environmental Microbiology*, 54(12):2953–2958, Dec. 1988.

Jensen, R.A., "The Shikimate/Arogenate pathway: Link Between Carbohydrate Metabolism and Secondary Metablosim," *Physiol. Plant.*, 66:164–168, 1985.

"Keystone Crops," *Agricultural Genetics Report*, Mar./Apr. 1990.

Klein et al., "Applications of the particle Gun in Plant Biology," Du Pont De Nemours & Co., Medical products Dept., Glasgow Site, Newark, Delaware, 19714–6101; U.S. Department of Agriculture–ARS/UC Berkeley, Plant Gene Expression Center, Albany, California, 94710.

Klein et al., "Genetic Transformation of Maize Cells by Particle Bombardment," *Plant Physiol.*, 91:440–444, 1989.

Klein et al., Genetic Transformation of Maize Cells by Particle Bombardment and the Influence of Methylation on Foreign–Gene Expression, Gene manipulation in Plant improvement II, p. 265–266, Editor J.P. Gustafson, Plenum Press, New York, 1990.

Koziel et al., "A Cauliflower Mosaic Virus Promoter Directs Expression of Kanamycin Resistance in Morphogenic Transformed Plant Cells," *Journal of Molecular and Applied Genetics*, 2:549–562, 1984.

Leemans, J., "Genetic Engineering for Sterility Control," *In Vitro Cellular & Developmental Biology*, Mar. 1992, 28(3).

Liu et al., "Degradation of the Herbicide Glyphosate by Member of the Family Rhizobiaceae," *Applied and Environmental Microbiology*, 57(6):1799–1804, Jun. 1991.

Mariani et al., "The Production and Analysis of Genetically–Engineered Male–Sterile Plants of Maize," *In Vitro Cellular & Developmental Biology*, 28(3), Part II, Mar. 1992, Poster 46.

Marshall, Kirkwood and Martin, "Studies on the Mode of Action of Asulamm Aminotriazole and Glyphosate in *Equisetum arvense* L. (Field Horsetail). II: The Metabolism of [$^{14}$C]Asulam, [$^{14}$C]Aminotriazole and [$^{14}$C]Glyphosate," *Pestic. Sci.*, 18:65–77, 1987.

Moffat, "Corn Transformed," *Science*, 249:630, 1990.

Mousdale and Coggins, "Subcellular Localization of the Common Shikimate–Pathway Enzymes in *Pisum savitum* L.," *Planta*, 163:241–249, 1985.

Murakami et al., The Bialaphos Biosynthetic Genes of *Streptomyces hygroscopicus:* Molecular Cloning and Characterization of the Gene Cluster, *Mol. Gen. Genet.*, 205:42–50, 1986.

Nafziger et al., "Selection and Characterization of a Carrolt Cell line Tolerant to Glyphosate," *Plant Physiol.*, 76:571–574, 1984.

Netzer, W.J., "Engineering Herbicide Tolerance: When Is It Worthwhile?," Bio/Technology, 2(11):939–944, Nov. 1984.

Omirulleh et al., "Activity of a Chimeric Promoter with the Doubled CaMV 35S Enhancer Element in Protoplast–Derived Cells and Transgenic Plants in Maize," *Plant Molecular Biology*, 21:415–428, 1993.

Park, "Selection of Maize Transformants from Shoot Apex Cultures Cocultivated with Argobacterium Containing the bar Gene," In Vitro Cellular & Developmental Biology, Jun. 5–9, 1993 Town & Contry Hotel San Diego, California.

Phillips et al., "Cell/Tissue Culture and In Vitro Manipulation," In Corn and Corn Improvement 3rd Edition, Editors Sprague and Dudley, American Society of Agronomy, Inc., Crop Science Society of America, Inc., and Soil Science Society of America, Inc., Madison, Wisconsin, USA, 1988.

Pipke and Amrhein, "Degradation of the Phosphonate Herbicide Glyphosate by *Arthrobacter atrocyaneus* ATCC 13752," *Applied and Environmental Microbiology*, 54(5):1293–1296, May 1988.

Rice, "DeKalb Genetics Transforms Corn with Herbicide–Resistance Gene," *Genetic Technology News*, 10(5) May 1990.

Rodgers et al., "Amplification of the aroA Gene from *Escherichcia coli* Results in Tolerance to the Herbicide Glyphosate," *Applied and Environmental Microbiology*, 46(1):37–43, Jul. 1983.

Ross and Tomes, "Transient and Stable Transgenic Cells and Calli of Tobacco and Maize Following Microprojectile Bombardment," *J. Cell. Biochem.*, Supplemental 13D, p. 268, 1989.

Rothe et al., "Evidence for an Intra– and Extraplastidic Pre–Chorismate Pathway," *Planta*, 157:358–366, 1983.

Rubin et al., "Enzymological Basis for herbicidal Action of Glyphosate," *Plant Physiol.*, 70:833–839, 1982.

Rubin et al., "Glyphosate Inhibition of 5–Enolpyruvylshikimate 3–Phosphate Synthase from Suspension–Cultured Cells of *Nicotiana silvestris,*" *Plant Physiol.*, 75:839–845, 1984.

Saijo and Takeo, "Some Properties of the Initial Four Enzymes Involved in Shikimic Acid Biosynthesis in Tea Plant," *Agric. Biol. Chem.*, 43(7):1427–1432, 1979.

Schmidt and Mishkind, "Rapid Degradation of Unassembled Ribulose 1,5 Bisphosphate Carboxylase Small Subunits in Chloroplasts," *Proc. Natl. Acad. Sci.,* 80:2632–2636, 1983.

Schowanek and Verstraete, "Phosphonate Utilization by Bacterial Cultures and Enrichments from Environmental Samples," *Applied and Environmental Microbiology,* 56(4):895–903, Apr. 1990.

Shah et al., "Engineering herbicide Tolerance in Transgenic Plants," *Science,* 233:478–481, Jul. 1986.

Singh, Connelly and Conn, "Chorismate Mutase isoenzymes from *Sorghum bicolor:* Purification and Properties," *Archives of Biochemistry and Biophysicis,* 243(2):374–384, 1985.

Smart et al., "Selective Overproduction of 5–enol–Pyruvylshikimic Acid 3–Phosphate Synthase in a Plant Cell Culture Which Tolerates High Doses of the Herbicide Glyphosate," *The Journal of Biological Chemistry,* 260(30):16338–16346, Dec. 1985.

Spencer et al., "Bialaphos Selection of Stable Transformants from Maize Cell Culture," *Theor. Appl. Genet.,* 79:625–631, 1990.

Spencer et al., "Fertile Transgenic Maize," p. 30 Seventh Annual Meeting of the Mid–Atlantic Plant Molecular Biology Society, Aug. 16 & 17, 1990, University of Maryland College Park.

Spencer et al., "Segregation of Transgenes in Maize," *Plant Molecular Biology,* 18:201–210, 1992.

Spencer et al., "Selection of Stable Transformants from Maize Suspension Cultures Using the herbicide Bialaphos," Department of Plant Genetics, Dekalb/Pfizer Genetics, Groton, CT 06340.

Stalker, Hiatt and Comai, "A Single Amino Acid Substitution in the Enzyme 5–Enolpyruvylshikimate–3–Phosphate synthase Confers Resistance to the Herbicide Glyphosate," The Journal of Biological Chemistry, 260(8):4724–4728, Apr. 1985.

Sun, M., "Engineering Crops to Resist Week Killers," *Science,* 231:1360–1361, Mar. 1986.

Thompson et al., "Characterization of the Herbicide–Resistance Gene bar from *Steptomyces hygroscopicus,*" *The EMBO Journal,* 6(9);2519–2523, 1987.

Van den Broeck et al., "Targeting of a Foreign Protein to Chloroplasts by Fusion to the Transit Peptide from the Small Subunit of Ribulose 1,5 Biphosphate Carboxylase," *Nature,* 313:358–363, Jan. 1985.

Wan and Lemaux, "Generation of Large Numbers of Independently Transformed Fertile Barley Plants," Plant Physiol., 104:37–48, 1994.

Wan et al., "Maize Transformation and Regeneration of Transgenic Plants by Microprojectile Bombardment of Type I Callus," *In Vitro Cellular & Developmental Biology,* 28(3), Part II, Mar. 1992.

Weidhase et al., "Utilization of Glyphosate by Pseudomonas sp. GS," *Zentralbl. Mikrobiol.,* 145:433–438, 1990.

Weising et al., "Foreign Genes in Plants: Transfer, Structure, Expression, and Applications," *Annu. Rev. Genet.,* 22:421–477, 1988.

White et al., "A Cassette Containing the bar Gene of *Streptomyces hygroscopicus:* A Selectable Marker for Plant Transformation," *Nucleic Acids Research,* 18(4):1062, Dec. 1989.

Polylinker1: 4.26/SacI.BstXI.SacII.XmaIII.NotI.XbaI.SpeI.BamHI.

| HYBRID | EVENT | MEAN ELH 10 DAT V4 ROUNDUP APPLICATION | | | | | | | MALE STERILE |
|---|---|---|---|---|---|---|---|---|---|
| | | 0X | 1X | Diff | RANK | 4X | Diff | RANK | |
| DK580 | GA21 | 104.1 | 102.4 | 1.7 | 1 | 102.3 | 1.8 | 1 | None |
| | FI117 | 100.1 | 97.7 | 2.3 | 2 | 97.7 | 2.4 | 2 | None |
| | GJ11 | 105.0 | 102.4 | 2.6 | 3 | 98.6 | 6.5 | 3 | None |
| | GG25 | 105.5 | 99.4 | 6.2 | 4 | 97.3 | 8.3 | 4 | None |
| DK626 | GA21 | 98.8 | 97.1 | 1.8 | 3 | 97.9 | 1.0 | 1 | None |
| | FI117 | 96.4 | 91.3 | 5.1 | 4 | 92.7 | 3.7 | 3 | None |
| | GJ11 | 96.0 | 96.8 | -0.8 | 1 | 94.0 | 2.0 | 2 | None |
| | GG25 | 99.5 | 97.8 | 1.6 | 2 | 93.1 | 6.4 | 4 | None |

FIG. 8A

| HYBRID | EVENT | MEAN ELH 10 DAT V8 ROUNDUP APPLICATION | | | | | | | | MALE STERILE |
|---|---|---|---|---|---|---|---|---|---|---|
| | | 0X | 1X | Diff | RANK | 4X | Diff | RANK | | |
| DK580 | GA21 | 142.7 | 139.6 | 3.1 | 3 | 139.2 | 3.5 | 2 | None |
| | FI117 | 143.4 | 139.5 | 3.9 | 4 | 139.1 | 4.3 | 3 | None |
| | GG25 | 141.4 | 139.8 | 1.6 | 2 | 136.5 | 5.0 | 4 | Yes |
| | GJ11 | 139.3 | 139.3 | 0.0 | 1 | 137.3 | 2.0 | 1 | Yes |
| DK626 | GA21 | 134.8 | 139.2 | -4.4 | 1 | 134.0 | 0.8 | 1 | None |
| | FI117 | 135.4 | 134.2 | 1.3 | 4 | 132.1 | 3.3 | 4 | None |
| | GJ11 | 135.7 | 137.7 | -2.0 | 2 | 133.1 | 2.6 | 3 | Yes |
| | GG25 | 135.5 | 136.6 | -1.0 | 3 | 134.0 | 1.6 | 2 | Yes |

FIG. 8B

| LEVEL 1 | | LEVEL 2 | | DIFFERENCE | Prob>T |
|---|---|---|---|---|---|
| HYBRID | RU*@TIMING | HYBRID | RU*@TIMING | (LEV. 1 - LEV. 2) | |
| DK580 | 0X | DK580 FI117 | 0X | -16.60 | 0.0339 |
| DK580 | 0X | DK580 FI117 | 4X@V4 | 11.33 | 0.1468 |
| DK580 FI117 | 0X | DK580 FI117 | 4X@V4 | 27.97 | 0.0004 |
| DK580 | 0X | DK580 GA21 | 0X | 3.67 | 0.6378 |
| DK580 | 0X | DK580 GA21 | 4X@V4 | -5.35 | 0.4923 |
| DK580 GA21 | 0X | DK580 GG21 | 4X@V4 | -9.02 | 0.2478 |
| DK580 | 0X | DK580 GG25 | 0X | -4.13 | 0.5957 |
| DK580 | 0X | DK580 GG25 | 4X@V4 | -3.50 | 0.6531 |
| DK580 GG25 | 0X | DK580 GG25 | 4X@V4 | 0.63 | 0.9352 |
| DK580 | 0X | DK580 GJ11 | 0X | -9.43 | 0.2267 |
| DK580 | 0X | DK580 GJ11 | 4X@V4 | -6.05 | 0.4376 |
| DK580 GJ11 | 0X | DK580 GJ11 | 4X@V4 | 3.38 | 0.6640 |

FIG. 9A

| LEVEL 1 | | LEVEL 2 | | DIFFERENCE | Prob>T |
|---|---|---|---|---|---|
| HYBRID | RU*@ TIMING | HYBRID | RU*@TIMING | (LEV. 1 - LEV. 2) | |
| DK626 | 0X | DK626 FI117 | 0X | -11.10 | 0.1559 |
| DK626 | 0X | DK626 FI117 | 4X@V8 | 5.12 | 0.5113 |
| DK626 FI117 | 0X | DK626 FI117 | 4X@V8 | 16.20 | 0.0388 |
| DK626 | 0X | DK626 GA21 | 0X | -2.58 | 0.7401 |
| DK626 | 0X | DK626 GA21 | 4X@V8 | -9.63 | 0.2171 |
| DK626 GA21 | 0X | DK626 GG21 | 4X@V8 | -7.05 | 0.3658 |
| DK626 | 0X | DK626 GG25 | 0X | -6.93 | 0.3738 |
| DK626 | 0X | DK626 GG25 | 4X@V8 | 23.97 | 0.0024 |
| DK626 GG25 | 0X | DK626 GG25 | 4X@V8 | 30.90 | 0.0001 |
| DK626 | 0X | DK626 GJ11 | 0X | 1.70 | 0.8272 |
| DK626 | 0X | DK626 GJ11 | 4X@V8 | 27.62 | 0.0005 |
| DK626 GJ11 | 0X | DK626 GJ11 | 4X@V8 | 25.92 | 0.0011 |

FIG.9B

```
  1  MASISSSVAT  VSRTAPAQAN  MVAPFTGLKS  NAAFPTTKKA  NDFSTLPSNG
 51  GGRVQCMQVW  PAYGNKKFET  LSYLPPLSMA  PTVMMASSAT  AVAPFQGLKS
101  TASLPVARRS  SRSLGNVSNG  GRIRCMAGAE  EIVLQPIKEI  SGTVKLPGSK
151  SLSNRILLIA  ALSEGTTVVD  NLLNSEDVHY  MLGALRTLGL  SVEADKAAKR
201  AVVVGCGGKF  PVEDAKEEVQ  LFLGNAGIAM  RSLTAAVTAA  GGNATYVLDG
251  VPRMRERPIG  DLVVGLKQLG  ADVDCFLGTD  CPPVRVNGIG  GLPGGKVKLS
301  GSISSQYLSA  LLMAAPLALG  DVEIEIIDKL  ISIPYVEMTL  RLMERFGVKA
351  EHSDSWDRFY  IKGGQKYKSP  KNAYVEGDAS  SASYFLAGAA  ITGGTVTVEG
401  CGTTSLQGDV  KFAEVLEMMG  AKVTWTETSV  TVTGPPREPF  GRKHLKAIDV
451  NMNKMPDVAM  TLAVVALFAD  GPTAIRDVAS  WRVKETERMV  AIRTELTKLG
501  ASVEEGPDYC  IITPPEKLNV  TAIDTYDDHR  MAMAFSLAAC  AEVPVTIRDP
551  GCTRKTFPDY  FDVLSTFVKN
```

FIG. 12

| FIG. 13-1 | FIG. 13-2 |
|---|---|
| FIG. 13-3 | FIG. 13-4 |

FIG. 13

963019 Test Map Example

| REP | ROW | COL1 | COL2 | COL3 | COL4 | COL5 | COL6 | COL7 | COL8 |
|---|---|---|---|---|---|---|---|---|---|
| 3 | 4 | DK580<br>GA21<br>T-4X@V4 | DK580<br>GA21<br>T-4X@V8 | DK580<br>GA21<br>T-1X@V4 | DK580<br>GA21<br>T-1X@V4 | DK580 | DK580<br>GA21<br>T-OX | DK626<br>GJ11<br>T-4X@V4 | DK626<br>GJ11<br>T-1X@V8 |
| 3 | 3 | DK580<br>FI117<br>T-1X@V4 | DK580<br>FI117<br>T-1X@V8 | DK580 | DK580<br>FI117<br>T-OX | DK580<br>FI117<br>T-4X@V8 | DK580<br>FI117<br>T-4X@V8 | DK626<br>GA21<br>T-1X@V8 | DK626<br>GA21<br>T-4X@V4 |
| 3 | 2 | DK580<br>GG25<br>T-1X@V8 | DK580<br>GG25<br>T-4X@V8 | DK580<br>GG25<br>T-OX | DK580<br>GG25<br>T-1X@V4 | DK580 | DK580<br>GG25<br>T-4X@V4 | DK626<br>GG25<br>T-1X@V4 | DK626<br>GG25<br>T-4X@V8 |
| 3 | 1 | DK580 | DK580<br>GJ11<br>T-4X@V8 | DK580<br>GJ11<br>T-1X@V4 | DK580<br>GJ11<br>T-4X@V8 | DK626<br>GJ11<br>T-OX | DK626<br>GJ11<br>T-1X@V8 | DK626<br>FI117<br>T-4X@V8 | DK626<br>FI117<br>T-OX |
| 3 | 1 | N-OX | | N-OX | T-OX | T-OX | T-4X@V4 | T-4X@V8 | |
| 2 | 4 | DK580<br>GJ11<br>T-OX | DK580<br>GJ11<br>T-1X@V4 | DK580 | DK580<br>GJ11<br>T-4X@V4 | DK580<br>GJ11<br>T-1X@V8 | DK580 | DK626<br>GJ11<br>T-1X@V4 | DK626<br>GJ11<br>T-1X@V4 |
| 2 | 4 | | | | | | | | |
| 2 | 4 | | N-OX | N-OX | T-OX | N-OX | T-1X@V4 | N-OX | T-OX |
| 2 | 3 | DK580<br>GG21<br>T-4X@V8 | DK580<br>GA21<br>T-1X@V8 | DK580<br>GA21<br>T-4X@V4 | DK580<br>GA21<br>T-OX | DK580 | DK580<br>GA21<br>T-1X@V4 | DK626 | DK626<br>GG25<br>T-OX |
| 2 | 2 | DK580<br>GG25<br>T-1X@V4 | DK580 | DK580<br>GG25<br>T-4X@V4 | DK580<br>GG25<br>T-4X@V4 | DK580<br>GG25<br>T-OX | DK580<br>GG25<br>T-4X@V4 | DK626<br>GG25<br>T-OX | DK626<br>FI117<br>T-OX |
| 2 | 1 | DK580<br>FI117<br>T-4X@V8 | N-OX | DK580<br>FI117<br>T-OX | DK580<br>FI117<br>T-1X@V4 | DK580<br>FI117<br>T-1X@V8 | DK580<br>FI117<br>T-4X@V4 | DK626<br>GA21<br>T-4X@V4 | DK626<br>N-OX |

FIG. 13-1

| COL9 | COL10 | COL11 | COL12 |
|---|---|---|---|
| DK626<br>GJ11<br>T-4X@V8 | DK626<br>GJ11<br>T-4X@V8 | DK626<br>GJ11<br>T-0X | DK626<br>GJ11<br>T-1X@V4 |
| N-OX | DK626<br>GA21<br>T-0X | DK626<br>GA21<br>T-1X@V4 | DK626<br>GA21<br>T-4X@V8 |
| DK626 | DK626<br>GG25<br>T-1X@V8 | DK626<br>GG25<br>T-4X@V4 | DK626 |
| N-OX | DK626<br>FI117<br>T-4X@V4 | DK626 | N-OX |
| DK626<br>GG25<br>T-0X | DK626<br>GJ11<br>T-1X@V8 | N-OX | DK626<br>FI117<br>T-1X@V4 |
| DK626<br>FI117<br>T-1X@V8 | DK626<br>GG25<br>T-4X@V4 | DK626 | DK626<br>GJ11<br>T-0X |
| DK626<br>GJ11<br>T-4X@V4 | DK626<br>FI117<br>T-4X@V8 | DK626<br>GG25<br>T-1X@V4 | DK626<br>GG25<br>T-4X@V4 |
| DK626<br>GG25<br>T-4X@V8 | DK626<br>GA21<br>T-1X@V4 | DK626<br>FI117<br>T-1X@V8 | DK626 |
| DK626<br>FI117<br>T-1X@V4 | DK626<br>GA21<br>T-0X | DK626<br>GA21<br>T-0X | N-OX |
| DK626<br>GA21<br>T-4X@V8 |  | DK626<br>GA21<br>T-0X | DK626<br>GA21<br>T-1X@V4 |

FIG. 13-2

| 1 | 4 | DK580 GA21 T-4X@V8 | DK580 | DK580 GA21 T-1X@V8 | DK580 GA21 T-4X@V4 | DK580 GA21 T-1X@V4 | DK580 GA21 T-0X | DK626 GA21 T-4X@V8 |
| --- | --- | --- | --- | --- | --- | --- | --- | --- |
| 1 | 4 | DK580 FI117 T-4X@V4 | DK580 FI117 | DK580 | DK580 FI117 T-4X@V4 | DK580 FI117 T-1X@V4 | DK580 FI117 T-4X@V8 | DK626 FI117 T-4X@V8 |
| 1 | 4 | | T-1X@V4 | | T-1X@V8 | T-0X | T-4X@V8 | |
| 1 | 3 | DK580 FI117 T-4X@V4 | DK580 FI117 T-1X@V4 | DK580 | DK580 FI117 T-1X@V8 | DK580 FI117 T-0X | DK580 FI117 T-4X@V8 | DK626 FI117 T-4X@V8 |
| 1 | 3 | DK580 GJ11 T-4X@V4 | DK580 GJ11 T-4X@V4 | N-0X | DK580 | DK580 GJ11 T-1X@V4 | DK580 GJ11 T-1X@V8 | DK626 GJ11 T-1X@V8 |
| 1 | 3 | | | | | | | T-4X@V8 |
| 1 | 2 | DK580 GJ11 T-4X@V4 | DK580 GJ11 T-4X@V4 | DK580 GJ11 T-0X | DK580 N-0X | DK580 | DK580 GJ11 T-1X@V8 | DK626 GG25 T-4X@V8 |
| 1 | 2 | DK580 GG25 T-4X@V4 | DK580 GG25 T-4X@V4 | DK580 GG25 T-4X@V4 | DK580 GG25 T-4X@V4 | DK580 GG25 T-1X@V4 | DK580 GG25 T-1X@V8 | DK626 GG25 T-4X@V8 |
| 1 | 2 | | | | | | | |
| 1 | 1 | DK580 | DK580 GG25 T-0X | DK580 GG25 T-4X@V4 | DK580 GG25 T-4X@V4 | DK580 GG25 T-1X@V4 | DK580 GG25 T-1X@V8 | DK626 GJ11 T-1X@V8 |
| 1 | 1 | N-0X | | | | | | |
| 1 | 1 | | | | | | | |

FIG. 13-3

| DK626 GA21 T-0X | DK626 GA21 T-1X@V4 | DK626 GA21 T-1X@V8 | DK626 N-0X |
|---|---|---|---|
| DK626 FI117 T-4X@V4 | DK626 N-0X | DK626 FI117 T-1X@V8 | DK626 FI117 T-0X |
| DK626 GG25 T-0X | DK626 N-0X | DK626 GG25 T-1X@V8 | DK626 GG25 T-1X@V4 |
| DK626 GJ11 T-0X | DK626 GJ11 T04X@V8 | DK626 GJ11 T01X@V4 | DK626 N-0X |

FIG. 13-4

GLYPHOSATE RESISTANT MAIZE LINES

BACKGROUND OF THE INVENTION

1. Field of the Invention

The present invention relates generally to transgenic maize plants which are resistant to the herbicide glyphosate. More specifically, it relates to the maize transformation events GA21, GG25, FI117 and GJ11.

2. Description of the Related Art

Chemical weed control is a powerful tool of our technological age. Long known as one of the most arduous of agricultural operations, weed killing has taken on an entirely new aspect as chemical after chemical is added to the arsenal of herbicides. The U.S. has led the world both in production and use of herbicides and as a result yields of maize, soybeans, cotton, sugar beets, and many other crops have increased since 1945, in some cases 100% or more. Thus while use of fertilizers and new high-yielding crop varieties have contributed greatly to the "green revolution" chemical weed control has been at the forefront in technological achievement.

A particularly useful type of herbicide is one having a broad spectrum of herbicidal activity. Use of such herbicides obviates the need for application of multiple herbicides. The problem with such herbicides is that they typically have a deleterious effect on any crops which are exposed to the herbicide. One way to overcome this is to produce transformed crop plants with genes which confer resistance to certain broad spectrum herbicides.

Recent advances in genetic engineering have provided the requisite tools to transform plants to contain foreign genes. Plants may, therefore, be produced which have unique characteristics of agronomic importance. Certainly, weed control via herbicide tolerance is one such advantageous trait which is highly cost effective and environmentally compatible. Herbicide-tolerant plants may reduce the need for tillage to control weeds, thereby effectively reducing soil erosion. Further, herbicide resistant plants can reduce the number of different herbicides applied in the field.

One herbicide which is the subject of much investigation in this regard is N-phosphonomethyl-glycine, commonly referred to as glyphosate. Glyphosate inhibits the shikimic acid pathway which leads to the biosynthesis of aromatic compounds including amino acids and vitamins. Specifically, glyphosate inhibits the conversion of phosphoenolpyruvic acid and 3-phosphoshikimic acid to 5-enolpyruvyl-3-phosphoshikimic acid by inhibiting the enzyme 5-enolpyruvyl-3-phosphoshikimic acid synthase (EPSP synthase or EPSPS).

It has been shown that glyphosate tolerant plants can be produced by introducing, into the genome of the plant, the capacity to produce a higher level of EPSP synthase which enzyme is preferably glyphosate tolerant (Shah et al., 1986). The introduction into plants of glyphosate degradation gene (s) can provide a means of conferring glyphosate tolerance to plants and/or to augment the tolerance of transgenic plants already expressing a glyphosate tolerant EPSP synthase depending upon the physiological effects of the degradation products.

Glyphosate metabolism (degradation) has been examined in a wide variety of plants and little degradation has been reported in most of those studies. In those instances where degradation has been reported, the initial breakdown product is usually aminomethylphosphonate (AMPA) (Coupland, 1985; Marshall et al., 1987). In these instances, it is not clear if glyphosate is metabolized by the plant or by the contaminating microbes on the leaf surface to which glyphosate was applied. AMPA has been reported to be much less phytotoxic than glyphosate for most plant species (Franz, 1985) but not for all plant species (Maier, 1983; Tanaka et al., 1986). Glyphosate degradation in soils is much more extensive and rapid (Torstensson, 1985). The principal breakdown product identified is AMPA (Rueppel et al., 1977; Nomura and Hilton, 1977); a phosphonate that can be metabolized by a wide variety of microorganisms (Zeleznick et al., 1963; Mastalerz et al., 1965; Cook et al., 1978; Daughton et al., 1979a; 1979b; 1979c; Wackett et al., 1987a). A number of pure cultures of bacteria have been identified that degrade glyphosate by one of the two known routes (Schowanek and Verstraete, 1990; Weidhase et al., 1990; Liu et al., 1991). A route involving a "C—P lyase" that degrades glyphosate to sarcosine and inorganic orthophosphate (Pi) has been reported for a Pseudomonas sp. (Shinabarger and Braymer, 1986; Kishore and Jacob, 1987) and an Arthrobacter sp. (Pipke et al., 1987b). Pure cultures capable of degrading glyphosate to AMPA have been reported for a Flavobacterium sp. (Balthazor and Hallas, 1986), for a Pseudomonas sp. (Jacob et al., 1988) and for *Arthrobacter atrocyaneus* (Pipke and Amrhein, 1988). In addition, a large number of isolates that convert glyphosate to AMPA have been identified from industrial activated sludges that treat glyphosate wastes (Hallas et al., 1988). However, the number and nature of bacterial genes responsible for these degradations have not been heretofore determined nor have the gene(s) been isolated.

The development of plants resistant to the herbicidal compound glyphosate has been a goal in the engineering of many plant species (U.S. Pat. No. 4,769,061). The development of glyphosate resistant tobacco plants was reported by Comai et al., (1985). Herbicide resistance was conferred on plants by expression of an aroA gene derived from *Salmonella typhimurium* encoding a glyphosate resistant form of the enzyme EPSP synthase. In addition, glyphosate resistant soybeans were produced (Monsanto, APHIS petition 93-258-01p). Methods for production of glyphosate resistant corn plants also have been described (WO 95/06128; U.S. Pat. No. 5,554,798). Similarly, a glyphosate oxidoreductase gene has been described for use in conferring glyphosate resistance (U.S. Pat. No. 5,463,175).

The ultimate goal in producing transgenic glyphosate resistant maize plants is to provide plants which may be treated with glyphosate at a level sufficient for killing weeds, without a deleterious effect on yield or fertility. In this respect, the prior art has failed. There is, therefore, a great need in agriculture for maize plants which can be directly sprayed in the field with glyphosate, thereby killing weeds, but otherwise not producing a deleterious effect on the crop itself.

SUMMARY OF THE INVENTION

The present invention seeks to overcome deficiencies in the prior art by providing fertile transgenic maize plants which can be treated with glyphosate in the field without a resulting loss in yield or fertility. Therefore, one aspect of the present invention relates to a fertile transgenic maize plant comprising a chromosomally incorporated expression cassette. In particular embodiments the expression cassette comprises: (i) a modified maize EPSPS gene encoding an EPSPS product having isoleucine at position 102 and serine at position 106, and (ii) a promoter active in maize operably linked to said EPSPS gene, wherein the yield of said fertile transgenic maize plant is not affected by a glyphosate application rate that affects the yield of a maize plant lacking said modified maize gene.

In another aspect, the maize plant may comprise a promoter which is selected from the group consisting of a rice actin promoter, a maize histone promoter and a fused CMV 35S-Arabidopsis histone promoter. In one embodiment, the plant may comprise an expression cassette which is derived from pDPG434, pDPG427 or pDPG443. The expression cassette may, in particular embodiments, be further be defined as pDPG434, and the maize plant may be further defined as comprising a transformation event selected from the group consisting of GA21 and FI117. The maize plant comprising the FI117 transformation event may further be defined as comprising a bar gene.

In yet another aspect, the maize plant may comprise a pDPG427 expression cassette and may be further defined as comprising the transformation event GG25 or, may comprise an expression cassette of pDPG443 and the maize plant may be further defined as comprising the transformation event GJ11. The invention is intended to include the progeny and seeds of the above maize plants, as well as the seeds of the progeny.

Still yet another aspect of the current invention comprises a method of preparing a fertile transgenic maize plant. The method comprises: (i) providing an expression cassette comprising (a) a modified maize EPSPS gene encoding an EPSPS product having isoleucine at position 102 and serine at position 106 and (b) a promoter active in maize operably linked to said EPSPS gene; (ii) contacting recipient maize cells with said expression cassette under conditions permitting the uptake of said expression cassette by said recipient cells; (iii) selecting recipient cells comprising a chromosomally incorporated expression cassette; (iv) regenerating plants from said selected cells; and (v) identifying a fertile transgenic maize plant, the yield of which is not affected by a glyphosate application rate that affects the yield of a maize lacking said modified maize gene.

The method may comprise any method of contacting including, but not limited to, microprojectile bombardment, electroporation, or Agrobacterium-mediated transformation. Said selecting may comprise treating recipient cells with glyphosate. The promoter may be selected from the group consisting of a rice actin promoter, a maize histone promoter and a fused CMV 35S-Arabidopsis histone promoter. In particular embodiments, said expression cassette may be derived from pDPG434, pDPG427 and pDPG443. The expression cassette may, in particular, be pDPG434 and the maize plant may be further defined as comprising a transformation event selected from the group consisting of GA21 and FI117. In the method, the transformation event may also be FI117, and said maize plant may further defined as comprising an bar gene. The expression cassette may also be pDPG427, and the maize plant may be further defined as comprising the transformation event GG25. The method also includes an expression cassette of pDPG443 where the maize plant may be further defined as comprising the transformation event GJ11.

In still yet another aspect, the invention is a fertile transgenic maize plant prepared according to a method comprising: (i) providing an expression cassette comprising (a) a modified maize EPSPS gene encoding an EPSPS product having isoleucine at position 102 and serine at position 106 and (b) a promoter active in maize operably linked to said EPSPS gene; (ii) contacting recipient maize cells with said expression cassette under conditions permitting the uptake of said expression cassette by said recipient cells; (iii) selecting recipient cells comprising a chromosomally incorporated expression cassette; (iv) regenerating plants from said selected cells; and (v) identifying a fertile transgenic maize, the yield of which is not affected by a glyphosate application rate that affects the yield of a maize lacking said modified maize gene. The maize may have a promoter selected from the group consisting of a rice actin promoter, a maize histone promoter and a fused CMV 35S-Arabidopsis histone promoter. The expression cassette may be derived from pDPG434, pDPG427 and pDPG443. The invention includes progeny and seeds of the fertile transgenic maize plant, as well as seeds of the progeny of the maize plant.

Still yet another aspect of the current invention is a glyphosate resistant, inbred, fertile maize plant comprising chromosomally incorporated expression cassette comprising (a) a modified maize EPSPS gene encoding an EPSPS product having isoleucine at position 102 and serine at position 106 and (b) a promoter active in maize operably linked to said EPSPS gene. The promoter may be selected from the group consisting of a rice actin promoter, a maize histone promoter and a fused CMV 35S-Arabidopsis histone promoter. The expression cassette may be derived from pDPG434, pDPG427 and pDPG443. In particular embodiments the inbred maize plant may be further defined as comprising a transformation event selected from the group consisting of GA21, GG25, GJ11 and FI117.

Still yet another aspect of the current invention is a glyphosate resistant, crossed fertile transgenic maize plant prepared according to the method comprising: (i) obtaining a fertile transgenic maize plant comprising a chromosomally incorporated expression cassette comprising (a) a modified maize EPSPS gene encoding an EPSPS product having isoleucine at position 102 and serine at position 106 and (b) a promoter active in maize operably linked to said EPSPS gene; (ii) crossing said fertile transgenic maize plant with a second maize plant lacking said expression cassette to obtain a third maize plant comprising said expression cassette; and (iii) backcrossing said third maize plant to obtain a backcrossed fertile maize plant; wherein said modified EPSPS gene is inherited through a male parent. In particular embodiments the second maize plant is an inbred. The third maize plant may be a hybrid. The maize plant may, in particular embodiments be further defined as comprising a transformation event selected from the group consisting of GA21, GG25, GJ11 and FI117.

Still yet another embodiment of the invention is a glyphosate resistant, crossed fertile transgenic maize plant prepared according to the method comprising: (i) obtaining a fertile transgenic maize plant comprising a chromosomally incorporated expression cassette comprising (a) a modified maize EPSPS gene encoding an EPSPS product having isoleucine at position 102 and serine at position 106 and (b) a promoter active in maize operably linked to said EPSPS gene; and (ii) crossing said fertile transgenic maize plant with a second maize plant lacking said expression cassette to obtain a third maize plant comprising said expression cassette; wherein said modified EPSPS gene is inherited through a female parent. In particular embodiments, the second maize plant may be an inbred, and the third maize plant may be a hybrid. The maize plant may, in particular embodiments, be further defined as comprising a transformation event selected from the group consisting of GA21, GG25, GJ11 and FI117.

Still yet another aspect of the invention is a glyphosate resistant, crossed fertile transgenic maize plant prepared according to the method comprising: (i) obtaining a fertile transgenic maize plant comprising a chromosomally incorporated expression cassette comprising (a) a modified maize EPSPS gene encoding an EPSPS product having isoleucine at position 102 and serine at position 106 and (b) a promoter active in maize operably linked to said EPSPS gene; (ii) crossing said fertile transgenic maize plant with a second maize plant to obtain a third maize plant comprising said expression cassette; and (iii) backcrossing said third maize plant to obtain a backcrossed fertile maize plant; wherein said modified EPSPS gene is inherited through a female parent. In particular embodiments, the maize plant may be an inbred and the third maize plant may be a hybrid. In one embodiment the maize plant may be further defined as comprising a transformation event selected from the group consisting of GA21, GG25, GJ11 and FI117.

Still yet another aspect of the current invention is a glyphosate resistant, hybrid maize plant comprising a chromosomally incorporated expression cassette comprising (a) a modified maize EPSPS gene encoding an EPSPS product having isoleucine at position 102 and serine at position 106 and (b) a promoter active in maize operably linked to said EPSPS gene. In one embodiment, the promoter is selected from the group consisting of a rice actin promoter, a maize histone promoter and a fused CMV 35S-Arabidopsis histone promoter and the expression cassette is derived from pDPG434, pDPG427 and pDPG443. The maize plant may, in particular embodiments, be further defined as comprising a transformation event selected from the group consisting of GA21, GG25, GJ11 and FI117.

Still yet another aspect of the invention is a glyphosate resistant, hybrid, transgenic maize plant prepared according to the method comprising crossing a first and second inbred maize plant, wherein one of said first and second inbred maize plants comprises a chromosomally incorporated expression cassette comprising (a) a modified maize EPSPS gene encoding an EPSPS product having isoleucine at position 102 and serine at position 106 and (b) a promoter active in maize operably linked to said EPSPS gene. In one embodiment, the promoter is selected from the group consisting of a rice actin promoter, a maize histone promoter and a fused CMV 35S-Arabidopsis histone promoter, and said expression cassette is derived from pDPG434, pDPG427 and/or pDPG443. The maize plant may, in particular embodiments, be further defined as comprising a transformation event selected from the group consisting of GA21, GG25, GJ11 and FI117.

Still yet another aspect of the invention is a glyphosate resistant, crossed fertile transgenic maize plant prepared by a process comprising: (i) obtaining a fertile transgenic maize plant comprising a chromosomally integrated expression cassette comprising (a) a modified maize EPSPS gene encoding an EPSPS product having isoleucine at position 102 and serine at position 106 and (b) a promoter active in maize operably linked to said EPSPS gene; (ii) crossing said fertile transgenic maize plant with a second maize plant to obtain a third maize plant comprising said expression cassette; and (iii) crossing said third fertile transgenic maize plant with a fourth maize plant to obtain a fifth transgenic maize plant comprising said expression cassette. In one embodiment, the second and fourth maize plants have the same genotype. In another embodiment the second and fourth maize plants have different genotypes.

Still yet another aspect of the invention is seed of a fertile, transgenic maize plant, said seed comprising a chromosomally incorporated expression cassette comprising (a) a modified maize EPSPS gene encoding an EPSPS product having isoleucine at position 102 and serine at position 106 and (b) a promoter active in maize operably linked to said EPSPS gene, said seed prepared by a process comprising the steps of: (i) obtaining a parental fertile, transgenic maize plant comprising a chromosomally incorporated expression cassette comprising (a) a modified maize EPSPS gene encoding an EPSPS product having isoleucine at position 102 and serine at position 106 and (b) a promoter active in maize operably linked to said EPSPS gene; (ii) breeding said parental plant with a second fertile maize plant to produce a plurality of progeny fertile, transgenic maize plants, said progeny maize plants including plants that express a chromosomally incorporated expression cassette comprising (a) a modified maize EPSPS gene encoding an EPSPS product having isoleucine at position 102 and serine at position 106 and (b) a promoter active in maize operably linked to said EPSPS gene; (iii) selecting from said progeny maize plants a plant having resistance to glyphosate; and (iv) obtaining seed from said selected progeny maize plant. In one embodiment the progeny maize plants are two generations removed from the parental transgenic maize plant.

The progeny maize plants having resistance to glyphosate may be selected by testing plants for resistance to glyphosate at an application rate of 1× (1× is equivalent to 16 ounces of Roundup™ per acre). The progeny maize plants having resistance to glyphosate may be selected by testing plants for resistance to glyphosate at an application rate of 4×. In a particular embodiment, the second fertile maize plant is a non-transgenic maize plant. The second fertile maize plant may be pollinated with pollen from a male parental transgenic maize plant. The parental maize plant may be pollinated with pollen from said second fertile maize plant and wherein said parental maize plant is a female parental transgenic maize plant.

Still yet another aspect of the invention is a method of increasing the yield of corn in a field comprising: (i) planting fertile transgenic maize plants transformed with an expression cassette comprising (a) a modified maize EPSPS gene encoding an EPSPS protein having isoleucine at position 102 and serine at position 106 and (b) a promoter active in maize operably linked to said EPSPS gene; and (ii) applying glyphosate to said field at an application rate that inhibits the yield of a maize plant that does not comprise said modified maize gene, wherein the yield of said fertile transgenic maize plant is not affected by said glyphosate application. In particular embodiments, the glyphosate application rate may be 1×, 2× or 4×.

Still yet another aspect of the invention is a method of inhibiting weed growth in a corn field comprising: (i) planting fertile transgenic maize plants transformed with an expression cassette comprising (a) a modified maize EPSPS gene encoding an EPSPS protein having isoleucine at position 102 and serine at position 106 and (b) a promoter active in maize operably linked to said EPSPS gene; and (ii) applying glyphosate to said field at an application rate that inhibits the yield of a maize plant that does not comprise said modified maize gene, wherein the yield of said fertile transgenic maize plant is not affected by said glyphosate application. In particular embodiments, the glyphosate application rate may be 1×, 2×, or 4×.

Still yet another aspect of the invention is a method of growing corn comprising: (i) planting fertile transgenic maize plants transformed with an expression cassette comprising (a) a modified maize EPSPS gene encoding an EPSPS protein having isoleucine at position 102 and serine at position 106 and (b) a promoter active in maize operably linked to said EPSPS gene; and (ii) treating said corn with glyphosate at an application rate that inhibits the yield of a maize plant that does not comprise said modified maize gene, wherein the yield of said fertile transgenic maize plant is not affected by said glyphosate application. In particular embodiments, the application rate may be, 1×, 2× or 4×.

It is clear that the ability to provide even a single fertile, transgenic corn line is generally sufficient to allow the introduction of the transgenic component (e.g., recombinant DNA) of that line into a second corn line of choice. This is because by providing fertile, transgenic offspring, the practice of the invention allows one to subsequently, through a series of breeding manipulations, move a selected gene from one corn line into an entirely different corn line. Therefore, the current invention is intended to include any maize plant, from any generation which has one or more transgenes comprising a GA21, GJ11, GG25 or FI117 transformation event, and includes the seeds thereof.

BRIEF DESCRIPTION OF THE DRAWINGS

FIGS. 9A and 9B. Yield effect of glyphosate application on DK580 and DK626 hybrids with the FI117, GA21, GG25 and GJ11 transformation events. Comparisons are made between the 4 transformation events in each of the two hybrids both with and without glyphosate application. Additionally, comparisons are made between each of the hybrids with the introgressed transformation event versus the hybrid without the transformation event. A. Comparisons of effect of glyphosate application on the yield of DK580 hybrids when applied at V4. B. Effect of glyphosate application on the yield of DK626 hybrids when applied at V8.

(FIG. 11C).

FIG. 12: Deduced amino acid sequence of the mutant corn EPSPS Protein. Sequence includes the OTP transit peptide isolated from corn and sunflower ribulose-1,5-bis phosphate carboxylase oxygenase (RuBisCo) genes, (amino acids 1–125 are the transit peptide).

FIGS. 13, 13-1, 13-2, 13-3, and 13-4: Field layout for study of glyphosate resistance in GA21, GG25, FI117 and GJ11 DK580 and DK626 hybrids. The repetition (1-3), column (COL1-COL12), row (1-4), hybrid (DK580 or DK626), transformation event (GA21, FI117, GG25, or GJ11), transformed or non-transformed status (N or T), glyphosate application level (0×, 1× or 4×), and developmental stage at glyphosate application (V4 or V8), are given. Tests were conducted in Dekalb, Ill., and Thomasboro, Ill. during 1996. All rows were planted at double normal planting density, i.e., 60 seeds per row, because hybrids segregated 1:1 for the glyphosate resistance trait. Sprayed plants were thinned to 30 plants per row no sooner than 7 days after application of glyphosate at a time when glyphosate susceptible plants could be identified. Unsprayed plots were thinned to 30 plants per row at the same time.

DETAILED DESCRIPTION OF THE INVENTION

Figure 1:
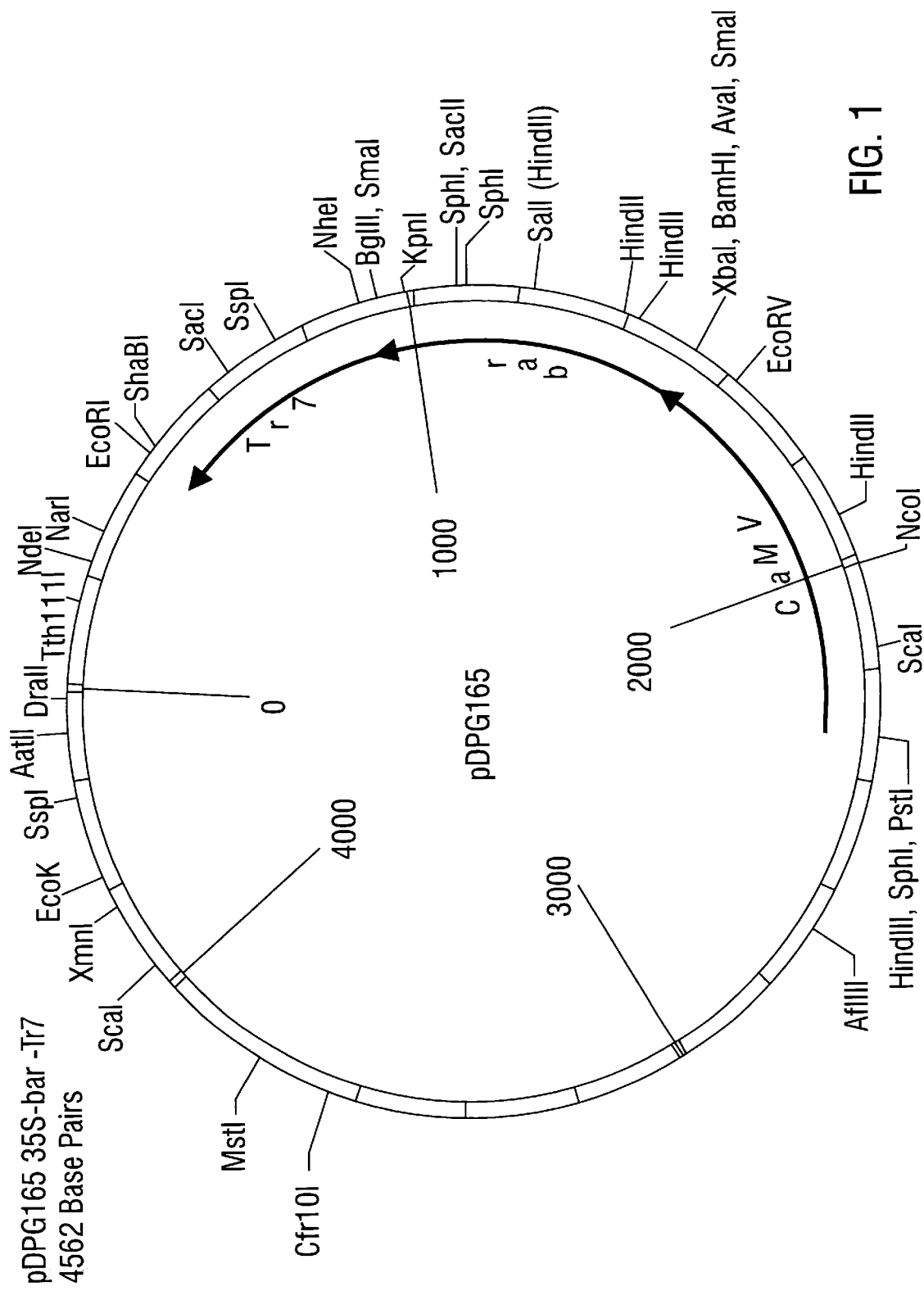
FIG. 1. Plasmid map of pDPG165. Restriction sites are shown and locations are indicated in base pairs.
Figure 2:
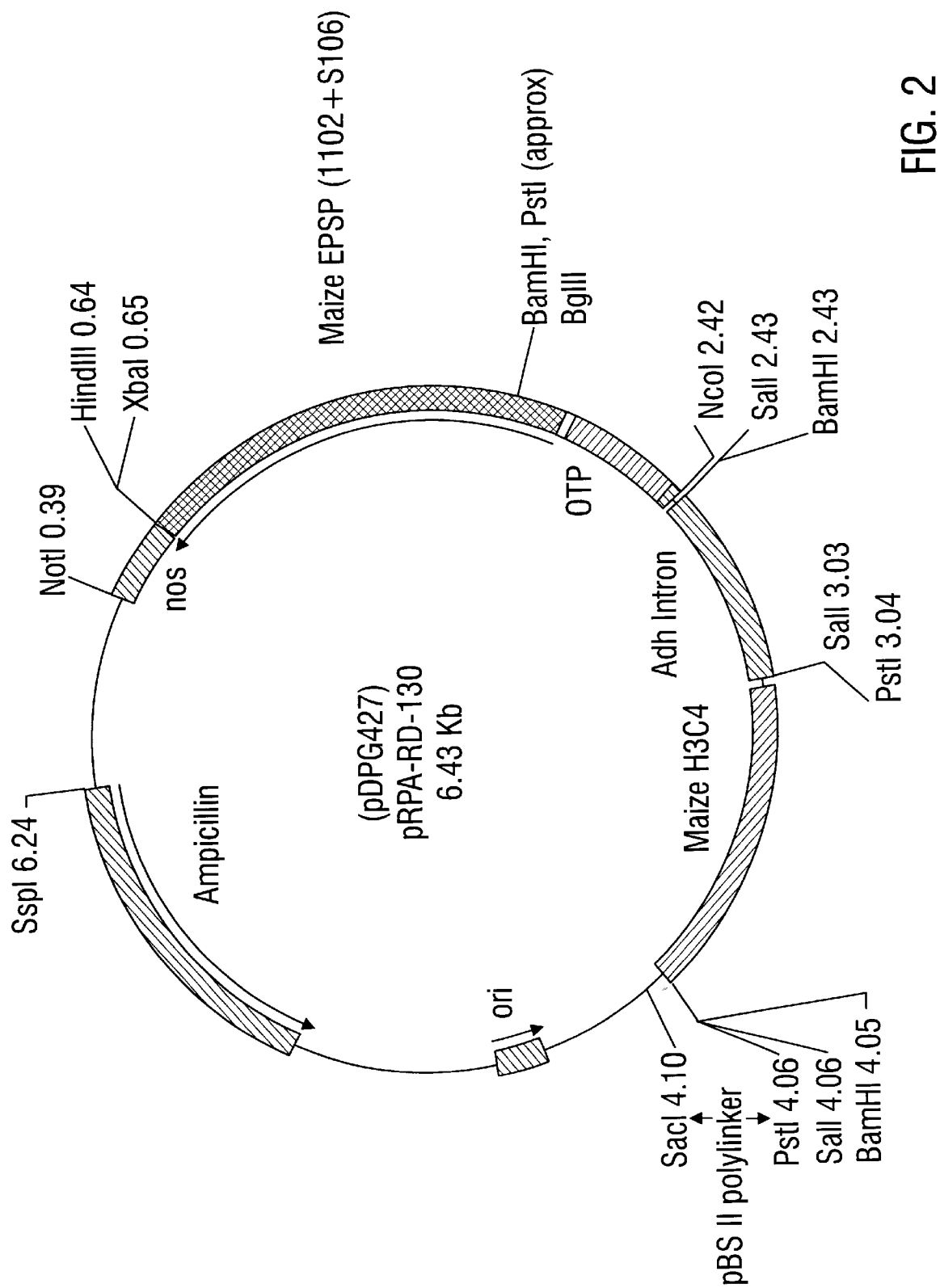
FIG. 2. Plasmid map of pDPG427. Restriction sites used for Southern blot analyses are shown and locations are indicated in base pairs.

In addition to direct transformation of a particular genotype with a mutant EPSPS gene, glyphosate resistant plants may be made by crossing a plant having a mutant EPSPS gene to a second, glyphosate sensitive plant. "Crossing" a plant to provide a plant line having an increased yield relative to a starting plant line, as disclosed herein, is defined as the techniques that result in a mutant EPSPS gene being introduced into a plant line by crossing a starting line with a donor plant line that comprises a mutant EPSPS gene. To achieve this one would, generally, perform the following steps:
(a) plant seeds of the first (starting line) and second (donor plant line that comprises a mutant EPSPS gene) parent plants;
(b) grow the seeds of the first and second parent plants into plants that bear flowers;
(c) pollinate the female flower of the first parent plant with the pollen of the second parent plant; and
(d) harvest seeds produced on the parent plant bearing the female flower.

Backcross conversion is herein defined as the process including the steps of:
(a) crossing a plant of a first genotype containing a desired gene, DNA sequence or element to a plant of a second genotype lacking said desired gene, DNA sequence or element;
(b) selecting one or more progeny plant containing the desired gene, DNA sequence or element;
(c) crossing the progeny plant to a plant of the second genotype; and
(d) repeating steps (b) and (c) for the purpose of transferring said desired gene, DNA sequence or element from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking said desired DNA sequence may be referred to as an unconverted genotype, line, inbred, or hybrid.

It is contemplated that glyphosate resistant plants may be obtained by transfer of the DNA sequence comprising a mutant EPSPS gene and adjacent plant genomic DNA sequences from FI117, GA21, GG25 and GJ11 mutant EPSPS gene transformed donor plants to a recipient plant whereby the recipient plant has increased tolerance to the herbicide glyphosate following introduction of the mutant EPSPS gene-encoding DNA segment. The DNA sequence may further be transferred to other genotypes through the process of backcross conversion and the glyphosate resistance of said backcross converted plants, or hybrids derived therefrom, is increased relative to the unconverted plant. The mutant EPSPS gene integration events, as well as the associated vector DNA, may be used as genetic markers in marker assisted breeding for the purpose of selecting maize plants with increased herbicide resistance.

I. Herbicide Control of Weeds

Chemical weed control is a science that involves knowledge in the fields of chemistry and biology, some familiarity with reactions of plants to phytotoxic agents, and at least observational experience in the responses of common weeds and crops to herbicides. Weed and crop ecology and appreciation of the factors determining selectivity, tolerance, and susceptibility are important. And finally, one needs a vast backlog of detailed information concerning the role of weed control in practical agriculture.

Weeds pose a threat to human health and welfare. They reduce the yield and value of crops; as well as increasing production and harvesting costs. The principal means by which weeds cause these effects are:

1. Competing with crop plants for the essentials of growth and development.
2. Production of toxic or irritant chemicals that cause human or animal health problems.
3. Production of immense quantities of seed or vegetative reproductive parts or both that contaminate agricultural products and perpetuate the species in agricultural lands.
4. Production on agricultural and nonagricultural lands of vast amounts of vegetation that must be disposed of.

In nonagricultural areas, weeds are often considered more of a nuisance than a threat; but even in this case weeds are a potential human hazard. Weed pollen may cause hay fever or other allergies, and toxic chemicals present in their sap or on their leaves may cause skin irritations or rashes when brushed against. Some substances produced by weeds are deadly when ingested. Weeds tend to hide tools and equipment, switches and valves, irrigation gates, and even holes in the ground. Dense, moisture-holding weed growth aids in the deterioration of wooden structures and the rusting of metal fences, buildings, and immobile machinery. Dead, dry weeds constitute a fire hazard, subject to ignition by a spark, a carelessly tossed cigarette, or even a piece of glass reflecting sunlight. Weeds reduce the enjoyment of recreation areas. They impede the flow of water in waterways and hamper water traffic especially in tropical and subtropical regions.

In agricultural lands, weeds reduce crop yields and quality, interfere with harvesting, and increase the time and costs involved in crop production. Weeds harbor insects and plant disease organisms; and in some cases, they serve as essential alternate hosts for these pests. Some weeds are undesirable in hay, pastures, and rangelands because of the mechanical injury that they inflict on livestock. Woody stems, thorns, and stiff seed awns cause injury to the mouth and digestive tract of livestock; and the hairs and fibers of some plants tend to ball up and obstruct the intestines, especially in horses, causing serious problems. Ingested by milk cows, some weeds such as ragweeds, wild garlic (*Allium vineale* L.), and mustard, among others, impart a distinctly distasteful odor or flavor to milk and butter. Barbed seed dispersal units may become so entangled in the wool of sheep as to greatly diminish its market value. Parasitic plants, such as dodder (Cuscuta sp.), broomrape (Orobanche sp.), and witchweed, rob their host plants of organic foodstuffs.

Weeds may additionally serve as host plants for pests of agriculture. Examples of weeds that serve as hosts for plant pests are cited below. Pepperweed and tansymustard (Descurainia sp.) maintain large populations of diamondback moths during the late fall, winter, and spring; they are also hosts to the turnip aphid and green peach aphid. Several weed species by the nightshade family (Solanaceae) are hosts to insects that commonly attack eggplant, pepper, potato, and tomato; for example, horsenettle (*Solanum carolinense* L.) is a host of the Colorado potato beetle, and black nightshade (*S. nigrum* L.) is a host of the cabbage looper. Morning-glory is an important host of insects attacking sweet potato, especially the highly destructive sweet potato weevil. Ragweed serves as a host for Mansonia mosquitoes, an insect vector for the human diseases encephalitis and rural filariasis. European barberry (*Berberis vulgaris* L.) is an essential host of the wheat stem rust in the northern wheat regions of the United States. Goosegrass (*Eleusine induce* [L.] Great.) and purple nutsedge are hosts of barley yellow dwarf virus. Currants and gooseberries (Ribes sp.) are hosts for white pine blister rust.

One crop which is highly reliant on chemical control of weeds is corn. Corn has been grown on 60 million to 83 million acres per year in the period from 1982 to 1993. In 1993, fifteen states had corn acreage in excess of one million acres, and 74% of the crop was grown in Iowa, Illinois, Nebraska, Minnesota, and Indiana. Herbicides were applied to about 97% of the corn acreage in the United States, and over 98% of the corn acreage in Iowa, Illinois, Minnesota, and Indiana had herbicide applications (Agricultural Chemical Usage, 1994). Furthermore, an average of 2.1 active ingredients were applied per acre in 1992.

Weeds compete with corn for nutrients, water, and light and when not controlled can significantly reduce the yield of corn. For examples, it is estimated that between 1972 and 1976 corn yields were reduced by about 10% due to weeds (Chandler, J. M., 1981, CRC Handbook of Pest Management in Agriculture, Vol. I, edited by Pimentel, D., pp. 95–109). It is especially important to control weed growth early in corn plant development, because even small numbers of weeds can have a dramatic negative impact on crop yield. Weeds are primarily controlled by mechanical or chemical means. Although mechanical cultivation is widely practiced, chemical weed control measures are wide spread and greater than 95% of the corn crop in the United States is treated with chemical herbicides. Indiscriminate use of herbicides, however, can lead to development of resistant weeds. Therefore it is important to develop methods of chemical weed control that represent novel modes of action and are unlikely to select for resistant weeds.

A diverse group of weed species necessitates a range of weed control methods in corn. Broad leaf weeds such as velvetleaf, pigweed, wild sunflowers, ragweed, and smartweed are of concern in corn. Furthermore, grass weeds such as johnson grass, shattercane, fall panicum, foxtails, quackgrass, wild proso millet and wooly cupgrass are common in corn. Perennial weeds are an additional problem as they are able to propagate by seed and/or underground plants parts, and may necessitate multiple herbicide applications. The wide array of weed species that are found in corn field requires the use of multiple type of herbicides and multiple applications in order to achieve weed control. Therefore, herbicide application regimes vary depending on the weed spectrum and local agronomic practices. Table 1 summarizes herbicide treatment of corn acreage in 1993.

A diverse group of weed species necessitates a range of weed control methods in corn. Broad leaf weeds such as velvetleaf, pigweed, wild sunflowers, ragweed, and smartweed are of concern in corn. Furthermore, grass weeds such as johnson grass, shattercane, fall panicum, foxtails, quackgrass, wild proso millet and wooly cupgrass are common in corn. Perennial weeds are an additional problem as they are able to propagate by seed and/or underground plants parts, and may necessitate multiple herbicide applications. The wide array of weed species that are found in corn field requires the use of multiple type of herbicides and multiple applications in order to achieve weed control. Therefore, herbicide application regimes vary depending on the weed spectrum and local agronomic practices. Table 1 summarizes herbicide treatment of corn acreage in 1993.

TABLE 1

Herbicide Applications to Corn
Percent of Acres Treated with Major Corn Herbicides

| Herbicide Name | Major Corn Growing States (Including Minn.) | Minnesota |
|---|---|---|
| Atrazine | 69 | 37 |
| Metolachlor | 32 | 24 |
| Alachlor | 24 | 23 |

TABLE 1-continued

Herbicide Applications to Corn
Percent of Acres Treated with Major Corn Herbicides

| Herbicide Name | Major Corn Growing States (Including Minn.) | Minnesota |
|---|---|---|
| Dicamba | 21 | 48 |
| Cyanazine | 20 | 16 |
| 2,4-D | 12 | 13 |
| Bromoxynil | 8 | 14 |
| Nicosulfuron | 6 | 19 |

Source: Agricultural Chemical Usage, March 1994, NASS and ERS, USDA.

A single application of herbicides near the time of planting is most common for corn. Usually this application comprises one of the triazine herbicides (atrazine, cyanazine, simazine) to control broadleaf weeds and an acetanilide herbicide (metolachlor, alachlor) to control annual grasses. Control of broadleaf weeds and problem grasses with postemergent herbicides such as dicamba, bromoxynil, bentazon, nicosulfuron and primisulfuron, occurred on about half of the corn acreage in 1993. Choice of herbicide is consistent in all but the north central states (e.g., Minnesota and South Dakota). Atrazine was used on about 69% of the corn acreage in 1993.

The most common tank mix was atrazine and metolachlor for broad spectrum weed control. Herbicide usage in the north central states, however, differs in that there is reduced usage of atrazine due to carryover to small grains and soybeans in the high pH, low rainfall soils of the region. Furthermore, because the growing season is shorter in the north central region, postemergent herbicides are preferred in that they do not delay planting operations. For example, in 1993, the most common herbicide used on corn in Minnesota was the postemergent herbicide dicamba (all data from Agricultural Chemical Usage, 1994).

In selecting a herbicide for control of weeds in corn, a chemical must be chosen that has a suitable spectrum of weeds that are killed and will not have adverse long lasting effects on the environment. In addition with increasing no till and minimum till acreage for corn, it is necessary to have weed control agents available that can be applied postemergence and spot applied as needed. Some of the herbicides currently applied to corn are limited in weed spectrum, may persist in soil or contaminate ground water, or may lead to the development of herbicide resistant weeds. Moreover, some herbicides that have reduced potential for adverse environmental effects and exhibit a broad spectrum of weed killing ability are non-discriminatory in their plant killing ability, i.e. crop plants such as corn are equally affected as weed species. It is only through introduction of genes conferring resistance to such herbicides that these chemicals can be used for weed control in corn.

Glyphosate is a broad spectrum post-emergence herbicide that is rapidly degraded in soil, has a low toxicity to non-target organisms, and does not contribute to ground water contamination. The availability of glyphosate for weed control in field grown corn has previously been lacking because of the broad spectrum of its effects. The glyphosate resistant transgenic plants described herein will give the farmer increased flexibility in dealing with weed problems. Glyphosate resistant corn hybrids will offer the farmer 1) the use of a new herbicide which offers broad spectrum control of annual and perennial, broad leaf and grass weeds; 2) less dependence on pre-plant herbicide applications; 3) increased flexibility in applying herbicides on an as needed basis; 4) a new herbicidal mode of action which will decrease the likelihood of development of herbicide resistant weeds; and 5) a herbicide for use in no-till systems which conserve fuel and reduce soil erosion. Because of the advantages offered, post-emergent herbicides are being applied to increasing acreage of corn every year, e.g., about 15 million acres of corn, 20% of the total corn acreage, receive only post-emergent herbicide applications. Glyphosate resistant corn will provide the farmer with an alternative weed control method. Currently on the average 2.1 herbicides are applied to corn during the growing season. It is expected that the use of glyphosate for weed control will reduce the number of kinds of herbicides applied as well as the number of required applications. Glyphosate resistant corn will, therefore, decrease the environmental risks posed by herbicides while at the same time increasing the efficacy of chemical weed control.

II. DNA Delivery

Following the generation of recipient cells, the present invention generally next includes steps directed to introducing an exogenous DNA segment into a recipient cell to create a transformed cell. The frequency of occurrence of cells receiving DNA is believed to be low. Moreover, it is most likely that not all recipient cells receiving DNA segments will result in a transformed cell wherein the DNA is stably integrated into the plant genome and/or expressed. Some may show only initial and transient gene expression. However, certain cells from virtually any monocot species may be stably transformed, and these cells developed into transgenic plants, through the application of the techniques disclosed herein.

There are many methods for introducing transforming DNA segments into cells, but not all are suitable for delivering DNA to plant cells. Suitable methods are believed to include virtually any method by which DNA can be introduced into a cell, such as by Agrobacterium infection, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles, etc. Agrobacterium-mediated transformation of maize was described in U.S. Pat. No. 5,591,616, which is specifically incorporated herein by reference. In certain embodiments, acceleration methods are preferred and include, for example, microprojectile bombardment and the like.

(i) Electroporation

Where one wishes to introduce DNA by means of electroporation, it is contemplated that the method of Krzyzek et al. (U.S. Pat. No. 5,384,253, incorporated herein by reference) will be particularly advantageous. In this method, certain cell wall-degrading enzymes, such as pectin-degrading enzymes, are employed to render the target recipient cells more susceptible to transformation by electroporation than untreated cells. Alternatively, recipient cells are made more susceptible to transformation, by mechanical wounding.

To effect transformation by electroporation one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding in a controlled manner. Such cells would then be recipient to DNA transfer by electroporation, which may be carried out at this stage, and transformed cells then identified by a suitable selection or screening protocol dependent on the nature of the newly incorporated DNA.

(ii) Microprojectile Bombardment

A further advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like. It is contemplated that in some instances DNA precipitation onto metal particles would not be necessary for DNA delivery to a recipient cell using microprojectile bombardment. However, it is contemplated that particles may contain DNA rather than be coated with DNA. Hence it is proposed that DNA-coated particles may increase the level of DNA delivery via particle bombardment but are not, in and of themselves, necessary.

An advantage of microprojectile bombardment, in addition to it being an effective means of reproducibly stably transforming monocots, is that neither the isolation of protoplasts (Cristou et al., 1988) nor the susceptibility to Agrobacterium infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with corn cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens may be positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/ microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Results from such small scale optimization studies are disclosed herein and the execution of other routine adjustments will be known to those of skill in the art in light of the present disclosure.

III. Recipient Cells for Transformation

Tissue culture requires media and controlled environments. "Media" refers to the numerous nutrient mixtures that are used to grow cells in vitro, that is, outside of the intact living organism. The medium is usually a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth will also vary among cultures initiated with the array of media that permit growth of that cell type.

Nutrient media is prepared as a liquid, but this may be solidified by adding the liquid to materials capable of providing a solid support. Agar is most commonly used for this purpose. Bactoagar, Hazelton agar, Gelrite, and Gelgro are specific types of solid support that are suitable for growth of plant cells in tissue culture.

Some cell types will grow and divide either in liquid suspension or on solid media. As disclosed herein, maize cells will grow in suspension or on solid medium, but regeneration of plants from suspension cultures requires transfer from liquid to solid media at some point in development. The type and extent of differentiation of cells in culture will be affected not only by the type of media used and by the environment, for example, pH, but also by whether media is solid or liquid. Table 2 illustrates the composition of various media useful for creation of recipient cells and for plant regeneration.

Recipient cell targets include, but are not limited to, meristem cells, Type I, Type II, and Type III callus, immature embryos and gametic cells such as microspores pollen, sperm and egg cells. It is contemplated that any cell from which a fertile transgenic plant may be regenerated is useful as a recipient cell. Type I, Type II, and Type III callus may be initiated from tissue sources including, but not limited to, immature embryos, seedling apical meristems, microspores and the such. Those cells which are capable of proliferating as callus are also recipient cells for genetic transformation. The present invention provides techniques for transforming immature embryos followed by initiation of callus and subsequent regeneration of fertile transgenic plants. Direct transformation of immature embryos obviates the need for long term development of recipient cell cultures. Pollen, as well as its precursor cells, microspores, may be capable of functioning as recipient cells for genetic transformation, or as vectors to carry foreign DNA for incorporation during fertilization. Direct pollen transformation would obviate the need for cell culture. Meristematic cells (i.e., plant cells capable of continual cell division and characterized by an undifferentiated cytological appearance, normally found at growing points or tissues in plants such as root tips, stem apices, lateral buds, etc.) may represent another type of recipient plant cell. Because of their undifferentiated growth and capacity for organ differentiation and totipotency, a single transformed meristematic cell could be recovered as a whole transformed plant. In fact, it is proposed that embryogenic suspension cultures may be an in vitro meristematic cell system, retaining an ability for continued cell division in an undifferentiated state, controlled by the media environment.

Cultured plant cells that can serve as recipient cells for transforming with desired DNA segments include corn cells, and more specifically, cells from *Zea mays* L. Somatic cells are of various types. Embryogenic cells are one example of somatic cells which may be induced to regenerate a plant through embryo formation. Non-embryogenic cells are those which typically will not respond in such a fashion. An example of non-embryogenic cells are certain Black Mexican Sweet (BMS) corn cells. These cells have been transformed by microprojectile bombardment using the neo gene followed by selection with the aminoglycoside, kanamycin (Klein et al., 1989). However, this BMS culture was not found to be regenerable.

The development of embryogenic maize calli and suspension cultures useful in the context of the present invention, e.g., as recipient cells for transformation, has been described in U.S. Pat. No. 5,134,074, which is incorporated herein by reference.

Certain techniques may be used that enrich recipient cells within a cell population. For example, Type II callus development, followed by manual selection and culture of friable, embryogenic tissue, generally results in an enrichment of recipient cells for use in, for example, microprojectile transformation. Suspension culturing, particularly using the media disclosed herein, may improve the ratio of recipient to non-recipient cells in any given population. Manual selection techniques which can be employed to select recipient cells may include, e.g., assessing cell morphology and differentiation, or may use various physical or biological means. Cryopreservation is a possible method of selecting for recipient cells.

Manual selection of recipient cells, e.g., by selecting embryogenic cells from the surface of a Type II callus, is one means that may be used in an attempt to enrich for recipient cells prior to culturing (whether cultured on solid media or in suspension). The preferred cells may be those located at the surface of a cell cluster, and may further be identifiable by their lack of differentiation, their size and dense cytoplasm. The preferred cells will generally be those cells which are less differentiated, or not yet committed to differentiation. Thus, one may wish to identify and select those cells which are cytoplasmically dense, relatively unvacuolated with a high nucleus to cytoplasm ratio (e.g., determined by cytological observations), small in size (e.g., 10–20 :m), and capable of sustained divisions and somatic proembryo formation.

It is proposed that other means for identifying such cells may also be employed. For example, through the use of dyes, such as Evan's blue, which are excluded by cells with relatively non-permeable membranes, such as embryogenic cells, and taken up by relatively differentiated cells such as root-like cells and snake cells (so-called due to their snake-like appearance).

Other possible means of identifying recipient cells include the use of isozyme markers of embryogenic cells, such as glutamate dehydrogenase, which can be detected by cytochemical stains (Fransz et al., 1989). However, it is cautioned that the use of isozyme markers such as glutamate dehydrogenase may lead to some degree of false positives from non-embryogenic cells such as rooty cells which nonetheless have a relatively high metabolic activity.

(i) Culturing Cells to be Recipients for Transformation

The inventors believe that the ability to prepare and cryopreserve cultures of maize cells is important to certain aspects of the present invention, in that it provides a means for reproducibly and successfully preparing cells for particle-mediated transformation, electroporation, or other methods of DNA introduction. The studies described below set forth techniques which have been successfully applied by the inventors to generate transformable and regenerable cultures of maize cells. A variety of different types of media have been developed by the inventors and employed in carrying out various aspects of the invention. The following table, Table 2, sets forth the composition of the media preferred by the inventors for carrying out these aspects of the invention.

TABLE 2

Tissue Culture Media Which are Used for Type II Callus Development, Development of Suspension Cultures and Regeneration of Plant Cells (Specifically Maize Cells)

| MEDIA NO. | BASAL MEDIUM | SUCROSE | pH | OTHER COMPONENTS** (Amount/L) |
|---|---|---|---|---|
| 7 | MS* | 2% | 6.0 | .25 mg thiamine<br>.5 mg BAP<br>.5 mg NAA<br>Bactoagar |
| 10 | MS | 2% | 6.0 | .25 mgthiamine<br>1 mg BAP<br>1 mg 2,4-D<br>400 mg L-proline<br>Bactoagar |
| 19 | MS | 2% | 6.0 | .25 mg thiamine<br>.25 mg BAP<br>.25 mg NAA<br>Bactoagar |
| 20 | MS | 3% | 6.0 | .25 mg<br>1 mg BAP<br>1 mg NAA<br>Bactoagar |
| 52 | MS | 2% | 6.0 | .25 mg thiamine<br>1 mg 2,4-D<br>$10^{-7}$ M ABA<br>BACTOAGAR |
| 101 | MS | 3% | 6.0 | MS vitamins<br>100 mg myo-inositol<br>Bactoagar |
| 142 | MS | 6% | 6.0 | MS vitamins<br>5 mg BAP<br>0.186 mg NAA<br>0.175 mg IAA<br>0.403 mg 2IP<br>Bactoagar |
| 157 | MS | 6% | 6.0 | MS vitamins<br>100 mg myo-inositol<br>Bactoagar |
| 163 | MS | 3% | 6.0 | MS vitamins<br>3.3 mg dicaniba<br>100 mg myo-inositol<br>Bactoagar |
| 171 | MS | 3% | 6.0 | MS vitamins<br>.25 mg 2,4-D<br>100 mg BAP<br>100 mg myo-inositol<br>Bactoagar |
| 173 | MS | 6% | 6.0 | MS vitamins<br>5 mg BAP<br>.186 mg NAA<br>.175 mg IAA<br>.403 mg 2IP<br>$10^{-7}$ M ABA<br>200 mg myo-inositol<br>Bactoagar |
| 177 | MS | 3% | 6.0 | MS vitamins<br>.25 mg 2,4-D<br>10 mg BAP |
| 185 | MS | — | 5.8 | $10^{-7}$ M ABA<br>100 mg myo-inositol<br>Bactoagar<br>3 mg BAP<br>.04 mg NAA<br>RT vitamins<br>1.65 mg thiamine<br>1.38 g L-proline<br>20 g sorbitol<br>Bactoagar |
| 189 | MS | — | 5.8 | 3 mg BAP<br>.04 mg NAA<br>.5 mg niacin<br>800 mg L-asparagine<br>100 mg casamino acids<br>20 g sorbitol<br>1.4 g L-proline<br>100 mg myo-inositol<br>Gelgro |
| 201 | N6 | 2% | 5.8 | N6 vitamins<br>2 mg L-glycine<br>1 mg 2,4-D<br>100 mg casein hydrolysate<br>2.9 g L-proline<br>Gelgro |
| 205 | N6 | 2% | 5.8 | N6 vitamins<br>2 mg L-glycine<br>.5 mg 2,4-D<br>100 mg casein hydrolysate<br>2.9 g L-proline<br>Gelgro |
| 209 | N6 | 6% | 5.8 | N6 vitamins<br>2 mg L-glycine<br>100 mg casein hydrolysate<br>0.69 g L-proline<br>Bactoagar |
| 210 | N6 | 3% | 5.5 | N6 vitamins<br>2 mg 2,4-D<br>250 nig Ca pantothenate<br>100 mg myo-inositol<br>790 mg L-asparagine<br>100 mg casein hydrolpate<br>1.4 g L-proline<br>Hazelton agar**** <br>2 mg L-glycine |
| 212 | N6 | — | 5.5 | N6 vitamins<br>2 mg L-glycine<br>2 mg 2,4-D<br>250 mg Ca pantothenate<br>100 mg myo-inositol<br>100 mg casein hydrolysate<br>1.4 g L-proline<br>Hazelton agar**** |
| 227 | N6 | 2% | 5.8 | N6 vitamins<br>2 mg L-glycine<br>13.2 mg dicamba<br>100 mg casein hydrolysate<br>2.9 g L-proline<br>Gelgro |
| 273 | N6 | 2% | 5.8 | N6 vitamins<br>2 mg L-glycine<br>1 mg 2,4-D<br>16.9 mg $AgNO_3$<br>100 mg casein hydrolysate<br>2.9 g L-proline |
| 279 | N6 | 2% | 5.8 | 3.3 mg dicamba<br>1 mg thiamine<br>.5 mg niacin<br>800 mg L-asparagine<br>100 mg casein hydrolysate<br>100 mg myoinositol<br>1.4 g L-proline |

TABLE 2-continued

Tissue Culture Media Which are Used for Type II Callus Development, Development of Suspension Cultures and Regeneration of Plant Cells (Specifically Maize Cells)

| MEDIA NO. | BASAL MEDIUM | SUCROSE | pH | OTHER COMPONENTS** (Amount/L) |
|---|---|---|---|---|
| 288 | N6 | 3% | | Gelgro**** 3.3 mg dicamba 1 mg thiamine .5 mg niacin .8 g L-asparagine 100 mg myo-inositol 1.4 g L-proline 100 mg casein hydrolysate 16.9 mg AgNO$_3$ Gelgro |
| 401 | MS | 3% | 6.0 | 3.73 mg Na$_2$EDTA .25 mg thiamine 1 mg 2,4-D 2 mg NAA 200 mg casein hydrolysate 500 mg K$_2$SO$_4$ 400 mg KH$_2$PO$_4$ 100 mg myo-inositol |
| 402 | MS | 3% | 6.0 | 3.73 mg Na$_2$EDTA .25 mg thiamine 1 mg 2,4-D 200 mg casein hydrolysate 2.9 g L-proline 500 mg K$_2$SO$_4$ 400 mg KH$_2$PO$_4$ 100 mg myo-inositol |
| 409 | MS | 3% | 6.0 | 3.73 mg Na$_2$EDTA .25 mg thiamine 9.9 mg dicamba 200 mg casein hydrolysate 2.9 g L-proline 500 mg K$_2$SO$_4$ 400 mg KH$_2$PO$_4$ 100 mg myo-inositol |
| 501 | Clark's Medium*** | 2% | 5.7 | |
| 607 | ½ × MS | 3% | 5.8 | 1 mg thiamine 1 mg niacin Gelrite |
| 615 | MS | 3% | 6.0 | MS vitamins 6 mg BAP 100 mg myo-inositol Bactoagar |
| 617 | ½ × MS | 1.5% | 6.0 | MS vitamins 50 mg myo-inositol Bactoagar |
| 708 | N6 | 2% | 5.8 | N6 vitamins 2 mg L-glycine 1.5 mg 2,4-D 200 mg casein hydrolysate 0.69 g L-proline Gelrite |
| 721 | N6 | 2% | 5.8 | 3.3 mg dicamba 1 mg thiamine .5 mg niacin 800 mg L-asparagine 100 mg myo-inositol 100 mg casein hydrolysate 1.4 g L-proline 54.65 g mannitoL Gelgro |
| 726 | N6 | 3% | 5.8 | 3.3 mg dicamba .5 mg niacin 1 mg thiamine 800 mg L-asparagine 100 mg myo-inositol 100 mg casein hydrolysate 1.4 g L-proline |
| 727 | N6 | 3% | 5.8 | N6 vitamins 2 mg L-glycine 9.9 mg dicamba 100 mg casein hydrolysate 2.9 g L-proline Gelgro |
| 728 | N6 | 3% | 5.8 | N6 vitamins 2 mg L-glycine 9.9 mg dicamba 16.9 mg AgNO$_3$ 100 mg casein hydrolysate 2.9 g L-proline Gelgro |
| 734 | N6 | 2% | 5.8 | N6 vitamins 2 mg L-glycine 1.5 mg 2,4-D 1 4 g Fe sequestreene (replaces Fe-EDTA) 200 mg casein hydrolyste 0.69 g L-proline Gelrite |
| 735 | N6 | 2% | 5.8 | 1 mg 2,4-D .5 mg niacin .91 g L-asparagine 100 mg myo-inositol 1 mg thiamine .5 g MES .75 g MgCl$_2$ 100 mg casein hydrolysate 0.69 g L-proline Gelgro |
| 2004 | N6 | 3% | 5.8 | 1 mg thiamine 0.5 mg niacin 3.3 mg dicamba 17 mg AgNO$_3$ 1.4 g L-proline 0.8 g L-asparagine 100 mg casein hydrolysate 100 mg myo-inositol Gelrite |
| 2008 | N6 | 3% | 5.8 | 1 mg thiamine 0.5 mg niacin 3.3 mg dicamba 1.4 g L-proline 0.8 g L-asparagine Gelrite |

*Basic MS medium described in Murashige and Skoog (1962). This medium is typically modified by decreasing the NH$_4$NO$_3$ from 1.64 g/l to 1.55 g/l, and omitting the pyridoxine HCl, nicotinic acid, myo-inositol and glycine.
**NAA = Napthol Acetic Acid
IAA = Indole Acetic Acid
2-IP = 2, isopentyl adenine
2,4-D = 2,4-Dichlorophenoxyacetic Acid
BAP = 6-benzyl aminopurine
ABA = abscisic acid
***Basic medium described in Clark (1982)
****These media may be made with or without solidifying agent.

A number of transformable maize cultures have been developed using the protocols outlined in the following examples. A compilation of the cultures initiated and tested for transformability is set forth in Table 3, with the results of the studies given in the two right-hand columns. The Table indicates the general selection protocol that was used for each of these cultures. The numeral designations under "Protocol" represent the following:

1. Tissue (suspension) was plated on filters, bombarded and then filters were transferred to culture medium. After 2–7 days, the filters were transferred to selective medium. Approximately 3 weeks after bombardment, tissue was picked from filters as separate callus clumps onto fresh selective medium.

2. As in 1 above, except after bombardment the suspension was put back into liquid—subjected to liquid selection for 7–14 days and then pipetted at a low density onto fresh selection plates.
3. Callus was bombarded while sitting directly on medium or on filters. Cells were transferred to selective medium 1–14 days after particle bombardment. Tissue was transferred on filters 1–3 times at 2 weeks intervals to fresh selective medium. Callus was then briefly put into liquid to disperse the tissue onto selective plates at a low density.
4. Callus tissue was transferred onto selective plates one to seven days after DNA introduction. Tissue was subcultured as small units of callus on selective plates until transformants were identified.

The totals demonstrate that 27 of 37 maize cultures were transformable. Of those cell lines tested 11 out of 20 have produced fertile plants and 7 are in progress. As this table indicates, transformable cultures have been produced from ten different genotypes of maize, including both hybrid and inbred varieties. These techniques for development of transformable cultures are important in direct transformation of intact tissues, such as immature embryos as these techniques rely on the ability to select transformants in cultured cell systems.

TABLE 3

Initiated Maize Cultures

| Genotype | Culture | Method | Transformable | Fertile Plants |
|---|---|---|---|---|
| A188 × B73 | G(1 × 6)92 | 1 | + | − |
| | G(1 × 6)716 | 1, 2 | + | + |
| | G(1 × 6)82 | 1 | + | + |
| | G(1 × 6)98 | 1 | − | NA |
| | G(1 × 6)99 | 1 | − | NA |
| | D(1 × 6)122#3 | 2 | − | NA |
| | D(1 × 6)114 | 2 | − | NA |
| | D(1 × 6)17#33 | 2 | − | NA |
| | HB13-3 | 3 | + | + |
| | HA133-227 | 2 | − | NA |
| | G(6 × 1)17#25C | 3 | + | + |
| | ABT4 | 4 | + | + |
| | ABT3 | 4 | + | + |
| | AB60 | 4 | + | + |
| | AB61 | 4 | + | + |
| | AB63 | 4 | + | + |
| | AB80 | 4 | + | + |
| | AB82 | 4 | + | + |
| | ABT6 | 4 | + | ND |
| | AB12 | 4 | + | + |
| | PH2 | 4 | + | + |
| | AB69 | 4 | + | − |
| | AB44 | 4 | + | − |
| | AB62 | 4 | + | ND |
| A188 × B84 | G(1 × M)82 | 1 | + | − |
| A188 × H99 | HJ11-7 | 3 | + | − |
| B73 × A188 | G(6 × 1)12#7 | 2 | − | NA |
| | D(6 × 1)11#43 | 2 | − | NA |
| | E1 | 2 | + | − |
| Hi-II | G(CW)31#24 | | + | + |
| B73 | (6)91#3 | 2 | − | NA |
| | (6)91#2 | 2 | − | NA |
| B73-derived | AT824 | 1, 2, 3 | + | + |
| N1017A | AZ11137a | 2 | + | − |
| Cat 100 | CB | 2 | + | ND |
| | CC | 2 | + | ND |
| A188 | E4 | 2 | + | − |

The symbol "−" indicates that the line was not transformable after 3 attempts or plants were sterile
NA indicates Not Applicable
ND indicates Not Done (ii) Media In certain embodiments, recipient cells are selected following growth in culture. Where employed, cultured cells may be grown either on solid supports or in the form of liquid suspensions. In either instance, nutrients may be provided to the cells in the form of media, and environmental conditions controlled. There are many types of tissue culture media comprised of amino acids, salts, sugars, growth regulators and vitamins. Most of the media employed in the practice of the invention will have some similar components (see, Table 2), the media differ in the composition and proportions of their ingredients depending on the particular application envisioned. For example, various cell types usually grow in more than one type of media, but will exhibit different growth rates and different morphologies, depending on the growth media. In some media, cells survive but do not divide.

Various types of media suitable for culture of plant cells have been previously described. Examples of these media include, but are not limited to, the N6 medium described by Chu et al. (1975) and MS media (Murashige & Skoog, 1962). The inventors have discovered that media such as MS which have a high ammonia/nitrate ratio are counterproductive to the generation of recipient cells in that they promote loss of morphogenic capacity. N6 media, on the other hand, has a somewhat lower ammonia/nitrate ratio, and is contemplated to promote the generation of recipient cells by maintaining cells in a proembryonic state capable of sustained divisions.

(iii) Maintenance

The method of maintenance of cell cultures may contribute to their utility as sources of recipient cells for transformation. Manual selection of cells for transfer to fresh culture medium, frequency of transfer to fresh culture medium, composition of culture medium, and environment factors including, but not limited to, light quality and quantity and temperature are all important factors in maintaining callus and/or suspension cultures that are useful as sources of recipient cells. It is contemplated that alternating callus between different culture conditions may be beneficial in enriching for recipient cells within a culture. For example, it is proposed that cells may be cultured in suspension culture, but transferred to solid medium at regular intervals. After a period of growth on solid medium cells can be manually selected for return to liquid culture medium. It is proposed that by repeating this sequence of transfers to fresh culture medium it is possible to enrich for recipient cells. It is also contemplated that passing cell cultures through a 1.9 mm sieve is useful in maintaining the friability of a callus or suspension culture and may be beneficial is enriching for transformable cells.

(iv) Cryopreservation Methods

Cryopreservation is important because it allows one to maintain and preserve a known transformable cell culture for future use, while eliminating the cumulative detrimental effects associated with extended culture periods.

Cell suspensions and callus were cryopreserved using modifications of methods previously reported (Finkle, 1985; Withers & King, 1979). The cryopreservation protocol comprised adding a pre-cooled (0° C.) concentrated cryoprotectant mixture stepwise over a period of one to two hours to pre-cooled (0° C.) cells. The mixture was maintained at 0° C. throughout this period. The volume of added cryoprotectant was equal to the initial volume of the cell suspension (1:1 addition), and the final concentration of cryoprotectant additives was 10% dimethyl sulfoxide, 10% polyethylene glycol (6000 MW), 0.23 M proline and 0.23 M glucose. The mixture was allowed to equilibrate at 0° C. for 30 minutes, during which time the cell suspension/cryoprotectant mixture was divided into 1.5 ml aliquot (0.5 ml packed cell volume) in 2 ml polyethylene cryo-vials. The tubes were cooled at 0.5° C./minute to −8° C. and held at this temperature for ice nucleation.

Once extracellular ice formation had been visually confirmed, the tubes were cooled at 0.5° C./minute from −8° C. to −35° C. They were held at this temperature for 45 minutes (to insure uniform freeze-induced dehydration throughout the cell clusters). At this point, the cells had lost the majority of their osmotic volume (i.e. there is little free water left in the cells), and they could be safely plunged into liquid nitrogen for storage. The paucity of free water remaining in the cells in conjunction with the rapid cooling rates from −35 to −196° C. prevented large organized ice crystals from forming in the cells. The cells are stored in liquid nitrogen, which effectively immobilizes the cells and slows metabolic processes to the point where long-term storage should not be detrimental.

Thawing of the extracellular solution was accomplished by removing the cryo-tube from liquid nitrogen and swirling it in sterile 42° C. water for approximately 2 minutes. The tube was removed from the heat immediately after the last ice crystals had melted to prevent heating the tissue. The cell suspension (still in the cryoprotectant mixture) was pipetted onto a filter, resting on a layer of BMS cells (the feeder layer which provided a nurse effect during recovery). Dilution of the cryoprotectant occurred slowly as the solutes diffused away through the filter and nutrients diffused upward to the recovering cells. Once subsequent growth of the thawed cells was noted, the growing tissue was transferred to fresh culture medium. The cell clusters were transferred back into liquid suspension medium as soon as sufficient cell mass had been regained (usually within 1 to 2 weeks). After the culture was reestablished in liquid (within 1 to 2 additional weeks), it was used for transformation experiments. When desired, previously cryopreserved cultures may be frozen again for storage.

IV. DNA Segments Comprising Exogenous Genes

As mentioned previously, there are several methods to construct the DNA segments carrying DNA into a host cell that are well known to those skilled in the art. The general construct of the vectors used herein are plasmids comprising a promoter, other regulatory regions, structural genes, and a 3' end.

The plants of the current invention have a mutant EPSPS gene which confers glyphosate resistance. The preferred EPSPS sequence, as shown in FIG. 12, includes a chloroplast transit peptide from maize in combination with the EPSPS gene. It is to be understood, that this chloroplast transit peptide could be homologous, i.e., from the maize EPSPS gene, or heterologous, i.e., from any other gene. Preferably the transit peptide will be the optimized transit peptide used in the constructs disclosed herein. Alternatively, the EPSPS gene may be used without a transit peptide and the gene transformed into the chloroplast genome following the techniques described in U.S. Pat. No. 5,451,513, specifically incorporated herein by reference.

Figure 3:
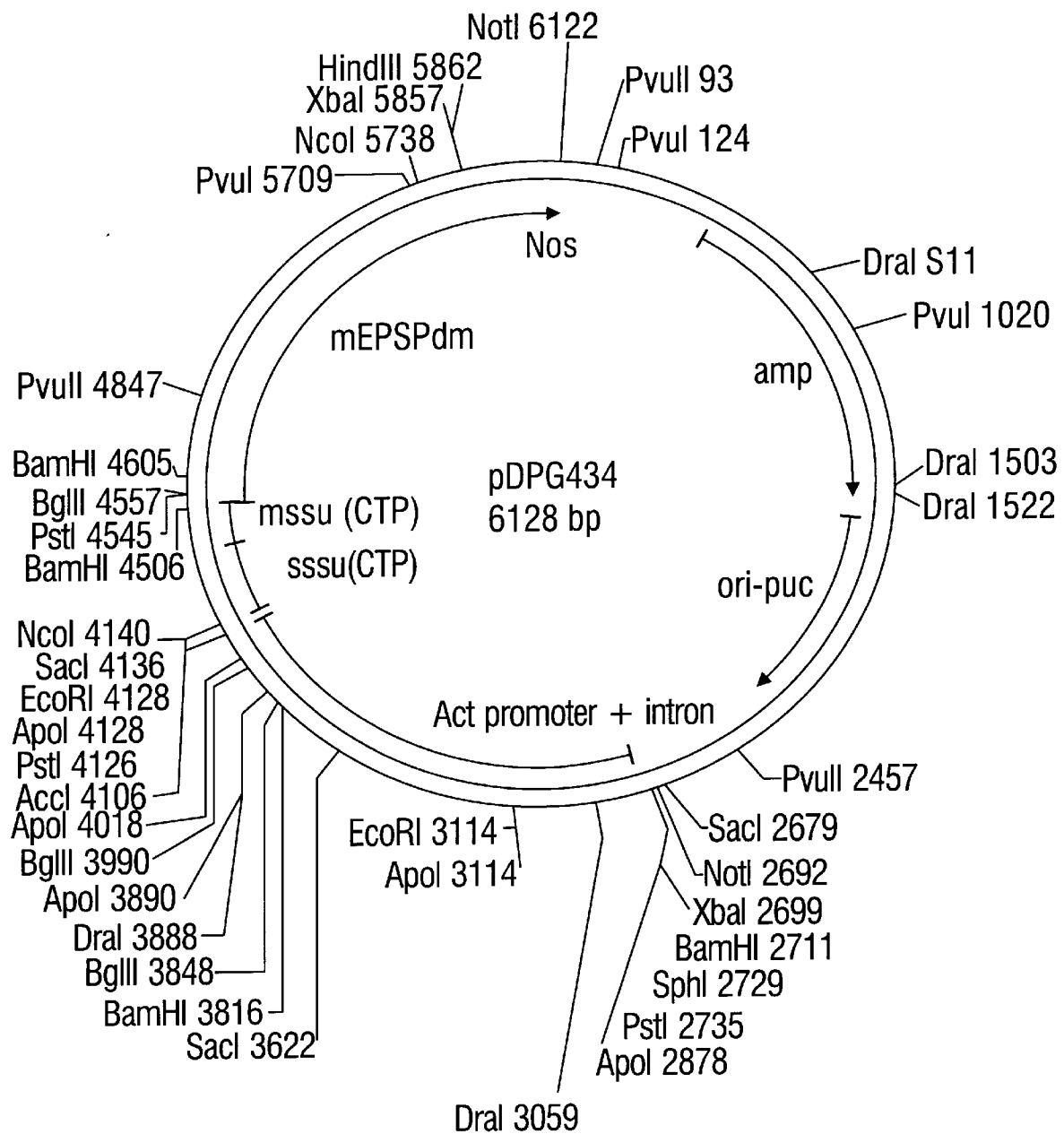
FIG. 3. Plasmid map of pDPG434. Restriction sites used for Southern blot analyses are shown and locations are indicated in base pairs.
Figure 4:
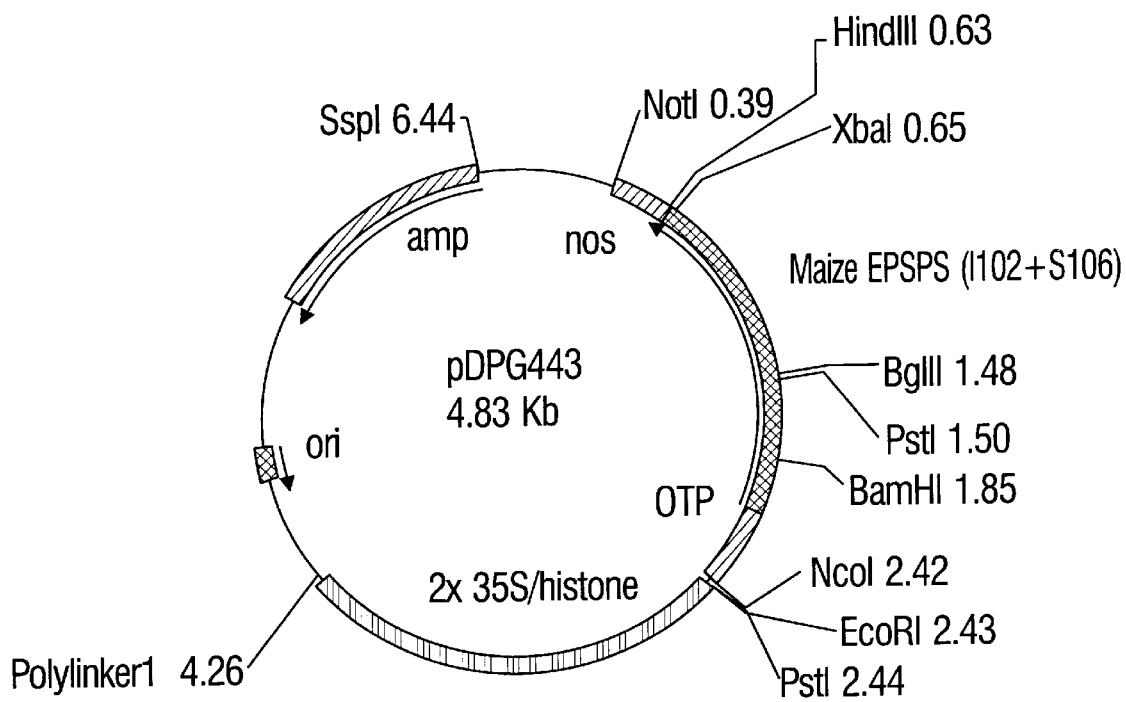
FIG. 4. Plasmid map of pDPG443. Restriction sites used for Southern blot analyses are shown and locations are indicated in base pairs.

Several plasmids encoding a variety of different genes have been constructed by the present inventors, the important features of which are represented below in Table 4. Certain of these plasmids are also shown in FIGS. 1–4: pDPG165 (FIG. 1), pDPG427 (FIG. 2), pDPG434 (FIG. 3), and pDPG443 (FIG. 4).

Table 4 shows vectors used in the construction of maize glyphosate resistant lines GA21, GG25, GJ11, and FI117. Table 5 shows the components of the plasmid pDPG434, which was used in the transformation of GA21 and FI117. The gene encoding the enzyme EPSPS was cloned from Zea mays. Two mutations were introduced into the amino acid sequence of EPSPS to confer glyphosate resistance, i.e., a substitution of isoleucine for threonine at amino acid position 102 and a substitution of serine for proline at amino acid position 106. Plant expression vectors pDPG427, pDPG434, and pDPG443 were constructed using the promoterless mutant maize EPSPS expression vector obtained from Rhone Poulenc Agrochimie (pDPG425). The mutant EPSPS gene in this vector encodes an enzyme with amino acid changes at positions 102 (threonine to isoleucine) and 106 (proline to serine). A description of the construction of these vectors is presented herein.

TABLE 4

Vectors used in the transformation of maize glyphosate resistant lines GA21, GG25, GJ11, and F1117.

| RECOMBINANT VECTOR DESIGNATION & SOURCE | PARENT REPLICON | INSERT DNA | DELIBERATE EXPRESSION ATTEMPT |
|---|---|---|---|
| pDPG165 | pUC19 | 1, 3, 4 | 1 |
| pDPG427 | pSK- | 2, 5, 6, 7 | 2 |
| pDPG434 | pSK- | 2, 9, 7, 6 | 2, 7 |
| pDPG443 | pSK- | 2, 6, 7, 8 | 2, 7 |

KEY: Insert DNA and Deliberate Expression Attempt

1. The bar gene from *Streptomyces hygroscopicus* encodes phosphinothricin acetyltransferase (PAT). Cells expressing PAT are resistant to the herbicide Basta. White, J., Chang, S.-Y. P., Bibb, M. J., and Bibb, M. J. 1990. Nucl. Ac. Research 18: 1062.

2. The EPSPS gene (5-enolpyruvy/shikimate-3-phosphate synthase) gene from *Zea Mays* was mutated to confer resistance to the herbicide glyphosate. An isoleucine has been substituted for threonine at amino acid position 102 and a serine has been substituted for proline at amino acid position 106.

3. Promoter sequences from the Cauliflower Mosaic Virus genome. Odell, J. T., Nagy, F., and Chua, N.-H. 1985. Nature 313: 810–812.

4. Terminator sequence from the Ti plasmid of *Agrobacterium tumefaciens*. (a) Bevan, M., 1984. Nucleic Acid Research 12: 8711–8721; (b) Ingelbrecht, I. L. W., Herman, L. M. F., DeKeyser, R. A., Van Montagu, M. C., Depicker, A. G. 1989. The Plant Cell 1: 671–680; (c) Bevan, M., Barnes, W. M., Chilton, M. D., 1983. Nucleic Acid Research. 11: 369–385; (d) Ellis, J. G., Llewellyn, D. J., Walker, J. C., Dennis, E. S., Peacocu, W. J. 1987. EMBO J. 6: 3203–3208.

5. Enhancer sequences from the maize alcohol dehydrogenase gene. Callis, J., Fromm, M. E., Walbot, V., 1987. Genes Dev. 1: 1183–1200.

6. Terminator sequences from Ti plasmid of Agrobacterium (nos 3'-end) (a) Bevan, M., 1984. Nucleic Acid Research 12: 8711–8721; (b) Ingelbrecht, I. L. W., Herman, L. M. F., DeKeyser, R. A., Van Montagu, M. C., Depicker, A. G. 1989. The Plant Cell 1: 671–680; (c) Bevan, M., Barnes, W. M., Chilton, M. D., 1983. Nucleic Acid Research. 11: 369–385.

7. A chloroplast transit peptide sequence, referred to here as the optimized transit peptide sequence (OTP), consisting of DNA sequence from maize and sunflower ribulose-1,5-bis phosphate carboxylase oxygenase (RuBisCo) genes (Lebrun et al., 1996; Rhone Poulenc Agrochimie).

8. Fused promoter sequences from Cauliflower Mosaic Virus genome and *Arabidopsis thaliana* H4 histone gene. Constructed by Rhone Poulenc Agrochimie.

9. Actin-1 5' region including promoter from *Oryza sativa* (McElroy et al. 1991).

TABLE 5

Summary of Sequences Present in Plasmid pDPG434

| Vector Component | Approx. Size, Kb | Description |
|---|---|---|
| rice actin promoter and intron | 1.37 | 5' region of the rice actin 1 gene containing the promoter and first intron (McElroy et al., 1991) |
| optimized transit peptide (OTP) | 0.37 | chloroplast transit peptide sequence constructed based on transit peptide sequences from maize and sunflower ribulose-1,5-bis phosphate carboxylase oxygenase (RuBisCo) genes (Lebrun et al., 1996) |
| mutant maize EPSPS gene | 1.34 | wild-type maize EPSPS gene (Lebrun et al., 1991) containing mutations at amino acid position 102 (threonine to isoleucine) and 106 proline to serine) |
| nos 3'-end | 0.24 | polyadenlylation region from the nopaline synthase gene from Agrobacteriuin tumefaciens (Bevan, 1984) |
| lac | 0.24 | A partial lacI coding sequence, the promoter plac, and a partial coding sequence for β-galactosidase or lacZ protein (Yanisch-Perron et al., 1985) |
| bla | 0.86 | The TEM type β-lactamase gene from *E. coli* plasmid pBR322 confers resistance on bacterial cells to ampicillin and other penicillins (Sutcliffe, 1978). The gene is under control of its native bacterial promoter. |
| ColE1 ori | 0.65 | The origin of DNA replication from the *E. coli* high copy plasmid pUC19 (Yanisch-Perron et al., 1985) |

V. Identification of Transformed Cells Using Selection

It is believed that DNA is introduced into only a small percentage of cells in any one experiment. In order to provide a more efficient system for identification of those cells receiving DNA and integrating it into their genomes, therefore, one may desire to employ a means for selecting those cells that are stably transformed. One exemplary embodiment of such a method is to introduce into the host cell, a marker gene which confers resistance to some normally inhibitory agent, e.g. an antibiotic or herbicide. The potentially transformed cells are then exposed to the agent. In the population of surviving cells are those cells wherein generally the resistance-conferring gene has been integrated and expressed at sufficient levels to permit cell survival. Cells may be tested further to confirm stable integration of the exogenous DNA. Using embryogenic suspension cultures, stable transformants are recovered at a frequency of approximately 1 per 1000 transiently expressing foci.

One herbicide which has been suggested as a desirable selection agent is the broad spectrum herbicide bialaphos. Bialaphos is a tripeptide antibiotic produced by Streptomyces hygroscopicus and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ is also effective as a selection agent. Inhibition of GS in plants by PPT causes the rapid accumulation of ammonia and death of the plant cells.

The organism producing bialaphos and other species of the genus Streptomyces also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato and potato plants (De Block, 1987) and Brassica (De Block, 1989). In previous reports, some transgenic plants which expressed the resistance gene were completely resistant to commercial formulations of PPT and bialaphos in greenhouses.

Another herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which infer glyphosate resistance on the *Salmonella typhimurium* gene for EPSPS, aroA. The EPSPS gene was cloned from *Zea mays* and mutations similar to those found in a glyphosate resistant aroA gene were introduced in vitro. The mutant gene encodes a protein with amino acid changes at residues 102 and 106. Although these mutations confer resistance to glyphosate on the enzyme EPSPS it is anticipated that other mutations will also be useful.

Exemplary embodiments of vectors capable of delivering DNA to plant host cells in the current invention are the plasmids, pDPG165, pDPG427, pDPG434, and pDPG443. These and other suitable plasmid vectors are further discussed in U.S. patent application Ser. No. 08/113,561, filed Aug. 25, 1993, which is specifically incorporated herein by reference. A very important component of the pDPG165 plasmid for purposes of genetic transformation is the bar gene which encodes a marker for selection of transformed cells exposed to bialaphos or PPT. Plasmids pDPG434, pDPG427, pDPG441, pDPG443, and pDPG436, pDPG447, pDPG465, and pDPG467 contain a maize EPSPS gene with mutations at amino acid residues 102 and 106 driven by various different promoters (U.S. patent application Ser. No. 08/113,561, filed Aug. 25, 1993). A very important component of these plasmids for purposes of genetic transformation is the mutated EPSPS gene which encodes a marker for selection of transformed cells.

VI. Production and Characterization of Stable Transgenic Corn

After effecting delivery of exogenous DNA to recipient cells, the next steps generally concern identifying the transformed cells for further culturing and plant regeneration. As mentioned herein, in order to improve the ability to identify transformants, one may desire to employ a selectable or screenable marker gene as, or in addition to, the expressible gene of interest. In this case, one would then generally assay the potentially transformed cell population by exposing the cells to a selective agent or agents, or one would screen the cells for the desired marker gene trait.

(i) Selection

An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

To use the bar-bialaphos or the EPSPS-glyphosate selective system, bombarded tissue is cultured for 0–28 days on nonselective medium and subsequently transferred to medium containing from 1–3 mg/l bialaphos or 1–3 mM glyphosate as appropriate. While ranges of 1–3 mg/l bialaphos or 1–3 mM glyphosate will typically be preferred, it is proposed that ranges of 0.1–50 mg/l bialaphos or 0.1–50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase may be used as a screenable marker in the context of the present invention. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time. Another screenable marker which may be used is the gene coding for green fluorescent protein.

It is further contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. It is proposed that combinations of selection and screening may enable one to identify transformants in a wider variety of cell and tissue types.

(ii) Regeneration and Seed Production

Cells that survive the exposure to the selective agent, or cells that have been scored positive in a screening assay, may be cultured in media that supports regeneration of plants. In an exemplary embodiment, MS and N6 media may be modified (see Table 2) by including further substances such as growth regulators. A preferred growth regulator for such purposes is dicamba or 2,4-D. However, other growth regulators may be employed, including NAA, NAA+2,4-D or perhaps even picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are transferred every two weeks on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber at about 85% relative humidity, 600 ppm $CO_2$, and 25–250 microeinsteins $m^{-2}s^{-1}$ of light. Plants are preferably matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Cons. Regenerating plants are preferably grown at about 19 to 28° C. After the regenerating plants have reached the stage of shoot and root development, they may be transferred to a greenhouse for further growth and testing.

Note, however, that kernels on transformed plants may occasionally require embryo rescue due to cessation of kernel development and premature senescence of plants. To rescue developing embryos, they are excised from surface-disinfected kernels 10–20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for one week on media containing the above ingredients along with $10^{-5}M$ abscisic acid and then transferred to growth regulator-free medium for germination.

Progeny may be recovered from the transformed plants and tested for expression of the exogenous expressible gene by localized application of an appropriate substrate to plant parts such as leaves. In the case of bar transformed plants, it was found that transformed parental plants ($R_0$) and their progeny ($R_1$) exhibited no bialaphos-related necrosis after localized application of the herbicide Basta7 to leaves, if there was functional PAT activity in the plants as assessed by an in vitro enzymatic assay. All PAT positive progeny tested contained bar, confirming that the presence of the enzyme and the resistance to bialaphos were associated with the transmission through the germline of the marker gene.

(iii) Characterization

To confirm the presence of the exogenous DNA or "transgene (s)" in the regenerating plants, a variety of assays may be performed. Such assays include, for example, "molecular biological" assays, such as Southern and Northern blotting and PCR; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

1. DNA Integration, RNA Expression and Inheritance

Genomic DNA may be isolated from callus cell lines or any plant parts to determine the presence of the exogenous gene through the use of techniques well known to those skilled in the art. Note, that intact sequences will not always be present, presumably due to rearrangement or deletion of sequences in the cell.

The presence of DNA elements introduced through the methods of this invention may be determined by polymerase chain reaction (PCR). Using this technique discreet fragments of DNA are amplified and detected by gel electrophoresis. This type of analysis permits one to determine whether a gene is present in a stable transformant, but does not prove integration of the introduced gene into the host cell genome. It is the experience of the inventors, however, that DNA has been integrated into the genome of all transformants that demonstrate the presence of the gene through PCR analysis. In addition, it is not possible using PCR techniques to determine whether transformants have exogenous genes introduced into different sites in the genome, i.e., whether transformants are of independent origin. It is contemplated that using PCR techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR, e.g., the presence of a gene.

Both PCR and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR techniques may also be used for detection and quantitation of RNA produced from introduced genes. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

2. Gene Expression

While Southern blotting and PCR may be used to detect the gene(s) in question, they do not provide information as to whether the gene is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}C$-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

VII. Purification of Proteins

It may, in particular embodiments of the current invention, be desirable to purify proteins encoded by transgenes of the current invention. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; and isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

VIII. Genetic Analysis of Glyphosate Resistant Transgenic Plants

In particular embodiments of the invention, methods may be used for detecting variation in the expression of particular transgenes such as the bar gene and mutant EPSPS. This method may comprise determining the level of protein expressed by these genes or by determining specific alterations in the expressed product. Obviously, this sort of assay has importance in the screening of transformants for potential herbicide resistance. Such assays may in some cases be faster, more accurate or less expensive than conventional screening assays.

The biological sample may potentially be any type of plant tissue. Nucleic acid is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given plant with a statistically significant reference group of non-transformed control plants. Typically, the non-transformed control plants will be of a genetic background similar to the transformed plants. In this way, it is possible to detect differences in the amount or kind of protein detected in various transformed plants.

A variety of different assays are contemplated in the screening of the glyphosate resistant plants of the current invention and associated exogenous elements. These techniques may in cases be used to detect for both the presence of the particular genes as well as rearrangements that may have occurred in the gene construct. The techniques include but are not limited to, fluorescent in situ hybridization (FISH), direct DNA sequencing, PFGE analysis, Southern or Northern blotting, single-stranded conformation analysis (SSCA), RNAse protection assay, allele-specific oligonucleotide (ASO), dot blot analysis, denaturing gradient gel electrophoresis, RFLP and PCR-SSCP.

(i) Primers and Probes

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

In preferred embodiments, the probes or primers are labeled with radioactive species ($^{32}p$, $^{14}C$, $^{35}S$, $^{3}H$, or other label), with a fluorophore (rhodamine, fluorescein), an antigen (biotin, streptavidin, digoxigenin), or a chemillumiscent (luciferase).

(ii) Template Dependent Amplification Methods

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, each of which is incorporated herein by reference in its entirety.

Briefly, in PCR, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPO No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention, Walker et al., (1992).

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EPO No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, M. A., In: *PCR PROTOCOLS: A GUIDE TO METHODS AND APPLICATIONS*, Academic Press, New York, 1990; Ohara et al., 1989; each herein incorporated by reference in their entirety).

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al., (1989), incorporated herein by reference in its entirety.

(iii) Southern/Northern Blotting

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

(iv) Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

(v) Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols. See Sambrook et al., 1989. For example, chromophore or radiolabel probes or primers identify the target during or following amplification.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al, 1994). The present invention provides methods by which any or all of these types of analyses may be used. Using the sequences disclosed herein, oligonucleotide primers may be designed to permit the amplification of sequences throughout the GA21, GG25, GJ11 and FI117 transformation events, as well as flanking genomic regions, which may then be analyzed by direct sequencing.

(vi) Design and Theoretical Considerations for Relative Quantitative RT-PCR

Reverse transcription (RT) of RNA to cDNA followed by relative quantitative PCR (RT-PCR) can be used to determine the relative concentrations of specific mRNA species isolated from plants. By determining that the concentration of a specific mRNA species varies, it is shown that the gene encoding the specific mRNA species is differentially expressed.

In PCR, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR amplification is directly proportional to the starting concentration of the target before the reaction began. By determining the concentration of the amplified products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR products and the relative mRNA abundances is only true in the linear range of the PCR reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR for a collection of RNA populations is that the concentrations of the amplified PCR products must be sampled when the PCR reactions are in the linear portion of their curves.

The second condition that must be met for an RT-PCR experiment to successfully determine the relative abundances of a particular mRNA species is that relative concentrations of the amplifiable cDNAs must be normalized to some independent standard. The goal of an RT-PCR experiment is to determine the abundance of a particular mRNA species relative to the average abundance of all mRNA species in the sample.

Most protocols for competitive PCR utilize internal PCR standards that are approximately as abundant as the target. These strategies are effective if the products of the PCR amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR assay for plant tissue. The problems inherent in plant tissue samples are that they are of variable quantity (making normalization problematic), and that they are of variable quality (necessitating the co-amplification of a reliable internal control, preferably of larger size than the target). Both of these problems are overcome if the RT-PCR is performed as a relative quantitative RT-PCR with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other studies may be performed using a more conventional relative quantitative RT-PCR assay with an external standard protocol. These assays sample the PCR products in the linear portion of their amplification curves. The number of PCR cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR assays can be superior to those derived from the relative quantitative RT-PCR assay with an internal standard.

One reason for this advantage is that without the internal standard/competitor, all of the reagents can be converted into a single PCR product in the linear range of the amplification curve, thus increasing the sensitivity of the assay. Another reason is that with only one PCR product, display of the product on an electrophoretic gel or another display method becomes less complex, has less background and is easier to interpret.

(vii) Chip Technologies

Specifically contemplated by the present inventors are chip-based DNA technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization. See also Pease et al. (1994); Fodor et al. (1991).

IX. Regeneration of Plants From Transformed Cells

For use in agriculture, transformation of cells in vitro is only one step toward commercial utilization of these new methods. Plants must be regenerated from the transformed cells, and the regenerated plants must be developed into full plants capable of growing crops in open fields. For this purpose, fertile corn plants are required.

During suspension culture development, small cell aggregates (10–100 cells) are formed, apparently from larger cell clusters, giving the culture a dispersed appearance. Upon plating these cells to solid media, somatic embryo development can be induced, and these embryos can be matured, germinated and grown into fertile seed-bearing plants. Alternatively, callus cells growing on solid culture medium can be induced to form somatic embryos from which fertile seed bearing plants may develop. The characteristics of embryogenicity, regenerability, and plant fertility are gradually lost as a function of time in suspension culture. Cryopreservation of suspension cells arrests development of the culture and prevents loss of these characteristics during the cryopreservation period.

DEPOSIT INFORMATION

A deposit of seeds comprising the GJ11, FI117, GG25 and GA21 transformation events has been made with the American Type Culture Collection (ATCC), 12301 Parklawn Drive, Rockville, Md., 20852. The date of deposit was May 14, 1997. The ATCC accession numbers for seed of maize plants comprising the GJ11, FI117, GG25 and GA21 transformation events are: ATCC 209030, ATCC 209031, ATCC 209032, and ATCC 209033, respectively.

X. EXAMPLES

Example 1

Initiation and Maintenance of Cell Line AT824

This example describes the initiation and maintenance of cell line AT824, which has been used routinely for transformation experiments. Immature embryos (0.5–1.0 mm) were excised from the B73-derived inbred line AT and cultured on N6 medium with 100 $\mu$M silver nitrate, 3.3 mg/L dicamba, 3% sucrose and 12 mM proline (2004). Six months after initiation type I callus was transferred to medium 2008. Two months later type I callus was transferred to a medium with a lower concentration of sucrose (279). A sector of type II callus was identified 17 months later and was transferred to 279 medium. This cell line is uniform in nature, unorganized, rapid growing, and embryogenic. This culture was desirable in the context of this invention as it is easily adaptable to culture in liquid or on solid medium.

The first suspension cultures of AT824 were initiated 31 months after culture initiation. Suspension cultures may be initiated in a variety of culture media including media containing 2,4-D as well as dicamba as the auxin source, e.g., media designated 210, 401, 409, 279. Cultures are maintained by transfer of approximately 2 ml packed cell volume to 20 ml fresh culture medium at 3 2 day intervals. AT824 can be routinely transferred between liquid and solid culture media with no effect on growth or morphology.

Suspension cultures of AT824 were initially cryopreserved 33–37 months after culture initiation. The survival rate of this culture was improved when it was cryopreserved following three months in suspension culture. AT824 suspension cultures have been cryopreserved and reinitiated from cryopreservation at regular intervals since the initial date of freezing. Repeated cycles of freezing have not affected the growth or transformability of this culture.

Example 2

Generation of Glyphosate Resistant Line GA21 by Microprojectile Bombardment of AT824 Cells The mutant maize EPSPS gene was introduced into AT824 suspension culture cells via microprojectile bombardment, essentially as described by U.S. Pat. No. 5,554,798 and U.S. patent application Ser. No. 08/113,561, filed Aug. 25, 1993, which are both specifically incorporated herein by reference in their entirety. In this example, the mutant maize EPSPS gene was derived from plasmid pDPG434 (FIG. 3). Plasmid pDPG434 contains a maize EPSPS gene with two amino acid changes, Thr to Ile at position 102 and Pro to Ser at position 106. An approximately 3.4 kb NotI restriction fragment containing the mutant maize EPSPS expression cassette of pPDG434 was used for transformation. The mutant maize EPSPS expression cassette contains a rice actin promoter and the nos 3' end.

Suspension culture AT824 (described in example 1) was subcultured to fresh medium 409 3 days prior to particle bombardment. Cells were plated on solid 279 medium 0–8 hours before bombardment (about 0.5 ml packed cell volume per filter).

DNA was precipitated onto gold particles as follows. A stock solution of gold particles was prepared by adding 60 mg of 0.7 μm or 1 μm gold particles to 1000 μl absolute ethanol and incubating for at least 3 hours at room temperature followed by storage at −20° C. Twenty to thirty five μl sterile gold particles were centrifuged in a microcentrifuge for 1 min. The supernatant was removed and one ml sterile water was added to the tube, followed by centrifugation at 2000 rpm for 5 minutes. Microprojectile particles were resuspended in 30 μl of DNA solution containing about 10–20 μg of the NotI restricted pDPG434 mutant EPSPS expression cassette. Two hundred twenty microliters sterile water, 250 μl 2.5 M CaCl$_2$ and 50 μl spermidine were added. The mixture was thoroughly mixed and placed on ice, followed by vortexing at 4 C. for 10 minutes and centrifugation at 500 rpm for 5 minutes. The supernatant was removed and the pellet resuspended in 600 μl absolute ethanol. Following centrifugation at 500 rpm for 5 minutes the pellet was resuspended in 36 μl of absolute ethanol and was allowed to settle for 4 minutes. Ten μl of the particle preparation were dispensed on the surface of the flyer disk and the ethanol was allowed to dry completely. The particles were then accelerated by a helium blast of approximately 1100 psi using the DuPont Biolistics PDS1000He particle bombardment device.

Following bombardment with gold particles coated with the pDPG434 expression cassette, AT824 cells were cultured on 279 medium (Table 2) for four days. Subsequently, the cells were returned to liquid 401 medium (Table 2), at a density of about 2 ml packed cell volume (PCV) per 20 ml, and cultured for four days. The cells were then transferred, at a density of 2 ml PCV/20 ml, to fresh 401 medium containing 1 mg/L bialaphos (bialaphos was accidently used instead of glyphosate at this stage) and cultured for four days. The subculture was repeated, this time into 401 plus 1 mM glyphosate, and after four days the cells were plated at a density of about 0.1 ml PCV per 100×20 mm petri dish containing 279 plus 1 mM glyphosate. Six to eight weeks after bombardment, glyphosate resistant colonies were removed from the selection plates and subcultured onto fresh 279 plus 1 mM glyphosate. Thirty five glyphosate resistant callus lines were recovered in this example. Approximately 96 plants were regenerated from 18 of the transgenic callus lines.

Example 3

Stable Transformation of AT824 Cells by Electroporation

Maize suspension culture cells were enzyme treated and electroporated using conditions described in Krzyek et al. (U.S. Pat. No. 5,384,956). AT824 suspension culture cells, three days post subculture, were sieved through 1000 μm stainless steel mesh and washed, 1.5 ml packed cells per 10 ml, in incubation buffer (0.2 M mannitol, 0.1% bovine serum albumin, 80 mM calcium chloride, and 20 mM 2-(N-morpholino)-ethane sulfonic acid, pH 5.6). Cells were then treated for 90 minutes in incubation buffer containing 0.5% pectolyase Y-23 (Seishin Pharmaceutical, Tokyo, Japan) at a density of 1.5 ml packed cells per 5 ml of enzyme solution. During the enzyme treatment, cells were incubated in the dark at approximately 25° C. on a rotary shaker at 60 rpm. Following pectolyase treatment, cells were washed once with 10 ml of incubation buffer followed by three washes with electroporation buffer (10 mM HEPES, 0.4 mM mannitol). Cells were resuspended in electroporation buffer at a density of 1.5 ml packed cells in a total volume of 3 ml.

Linearized plasmid DNA, about 60 μg of NotI excised EPSPS expression cassette from pDPG427 (GG25) or pDPG443 (GJ11); or 100 μg of whole pDPG165 and pDPG434 (FI117) plasmid DNA (50 μg from each plasmid), was added to 0.5 ml aliquots of electroporation buffer. The DNA/electroporation buffer was incubated at room temperature for approximately 10 minutes. To these aliquots, 0.5 ml of suspension culture cells/electroporation buffer (containing approximately 0.25 ml packed cells) were added. Cells and DNA in electroporation buffer were incubated at room temperature for approximately 10 minutes. One half ml aliquots of this mixture were transferred to the electroporation chamber (Puite, 1985) which was placed in a sterile 60×15 mm petri dish. Cells were electroporated with a 70, 100, or 140 volt (V) pulse discharged from a 140 microfarad (μf) capacitor.

Approximately 10 minutes post-electroporation, cells were diluted with 2.5 ml 409 medium containing 0.3 M mannitol. Cells were then separated from most of the liquid medium by drawing the suspension up in a pipet, and expelling the medium with the tip of the pipet placed against the petri dish to retain the cells. The cells, and a small amount of medium (approximately 0.2 ml) were dispensed onto a filter (Whatman #1, 4.25 cm) overlaying solid 279 medium (Table 2) containing 0.3 M mannitol. After about five days, the tissue and the supporting filters were transferred to 279 medium containing 0.2 M mannitol. After about six days, tissue and supporting filters were transferred to 279 medium without mannitol.

Example 4

Regeneration of AT824 Transformants

Transformants were produced as described in Example 2 and Example 3. For regeneration, tissue was maintained on maintenance medium (279) containing 1 mM glyphosate or 1 mg/L bialaphos. Subsequently transformants were subcultured one to three times, but usually twice on 189 medium (first passage in the dark and second passage in low light) and once or twice on 101 medium in petri dishes before being transferred to 501 or 607 medium in Plant Cons. Variations in the regeneration protocol are normal based on the progress of plant regeneration. Hence some of the transformants were first routinely subcultured on maintenance medium, followed by twice on 189 medium, once or twice on 101 medium, followed by transfer to 501 or 607 medium in Plant Cons8. As shoots developed on 101 medium, the light intensity was increased by slowly adjusting the distance of the plates from the light source located overhead. All subculture intervals were for about 2 weeks at about 24° C. Transformed plants that developed shoots roots were transferred to soil.

Plantlets in soil were incubated in an illuminated growth chamber and conditions were slowly adjusted to adapt or condition the plantlets to the drier and more illuminated conditions of the greenhouse. After adaptation/conditioning in the growth chamber, plants were transplanted individually to 5 gallon pots of soil in the greenhouse.

Example 5

Regeneration of Glyphosate Resistant Line FI117 Using Bialaphos Selection

Cells of AT824 were electroporated with plasmids pDPG165 and pDPG434 as described in example 3. In this case, co-transformation with the bar gene-containing plasmid pDPG165 allowed for selection on bialaphos. Following recovery and after the tissue had grown for about four days on 279 medium, the tissue on each filter was transferred to a flask containing about 20 ml of liquid 401 medium containing 1 mg/L bialaphos. Four days later, tissue in each flask was transferred to a new flask containing about 20 ml fresh 401 medium containing 1 mg/L bialaphos. Three days later the cells were plated at a density of about 0.1 ml PCV per 100×20 mm petri dish containing 279 medium plus 1 mg/L bialaphos. Approximately 34 bialaphos resistant callus lines were selected in this example, at a frequency of 17 callus lines per electroporation. Approximately 48 plants were regenerated from 18 callus lines. Screening of plants for glyphosate resistance was subsequently carried out as described in example 5.

Example 6

Screening Transgenic Plants for Glyphosate Resistance

Plants regenerated from callus lines GA21, GG25, GJ11, and FI117 ($R_0$ generation), which each contained the mutant EPSPS gene, were crossed to nontransgenic inbred plants in the greenhouse. The progeny of these crosses were expected to segregate 1:1 for the herbicide resistance trait. Glyphosate resistance was evaluated in the progeny of the $R_0$ crosses ($R_1$ generation) in a greenhouse by application of Roundup™ brand (Monsanto) glyphosate at a rate of 16 oz./acre. Transgenic lines that exhibited resistance to glyphosate were selected and again backcrossed to a nontransgenic inbred. The resulting progeny were then screened for glyphosate resistance in field tests. From these tests, the GA21, FI117, GG25 and GJ11 transformation events were selected for further study based their glyphosate resistant phenotype.

Example 7

Isolation of Genomic Corn DNA

Glyphosate resistant corn lines GA21, FI117, GG25 and GJ11 were crossed to various inbred lines to facilitate hybrid development as described in example 14. Genomic DNA used for Southern blot analyses was isolated from the resulting backcrossed plants. The backcross populations consisted of plants that were segregating 1:1 for the GA21, FI117, GG25 or GJ11 insertion. Positive and negative GA21 segregants were identified by polymerase chain reaction (PCR) using oligonucleotide primers specific to the pDPG434 fragment used for transformation. Negative segregants served as nontransgenic control plants. The PCR primers used for the analysis spanned the mutant EPSPS-nos junction and generated a 192 bp fragment. The sequence of the upper primer located on the mutant EPSPS gene is 5'-ACGTACGACGACCACAGGATG-3' (SEQ ID NO:1). The sequence of the lower primer located in nos is 5'-GCAAGACCGGCAACAGGATTC-3' (SEQ ID NO:2). Genomic DNA was isolated from positive and negative plants as described in Dellaporta et al., (1983). DNA was isolated from field-grown and greenhouse-grown plants.

Example 8

DNA Probe Preparation and Hybridization

DNA fragments used for probe preparation were isolated by gel-purification of restriction digests of plasmid DNA or were generated by PCR. The mutant EPSPS PCR fragment used as a probe was generated using primers that produce a 324 bp fragment internal to the EPSPS gene. This fragment initiates approximately 400 bp down stream from the start codon. The primer sequences used to generate this fragment are: 5'-TTTGGCTCTTGGGGATGTG-3' (SEQ ID NO:3) (upper) and 5'-TTACGCTAGTCTCGGTCCAT-3' (SEQ ID NO:4)(lower). Probes were labeled with $^{32}P$ using the random priming method (Boehringer Mannheim) and purified using Quik-Sep® spin columns (Isolab Inc., Akron, Ohio). Blots were prehybridized at 65° C. for 1–2 hours and hybridized with denatured probe for approximately 18 hours at 65° C. Prehybridization and hybridization solution consisted of 5× SCP, 2× Denhardt's Solution, 0.05 M Tris, pH 8.0, 0.2% SDS, 10 mM EDTA, 100 mg/l dextran sulfate, and 125 µg/ml denatured salmon sperm DNA. Following hybridization, blots were washed 4 times for 10 min. in 0.25× SCP/0.2% SDS. Membranes were blotted dry and visualized by autoradiography. To reprobe blots, probes were removed by treating blots in 0.05 M NaOH/0.2% SDS for 10 min. followed by neutralization in 0.2 M Tris, pH 7.5/0.2% SDS/0.1× SCP for 20 minutes at approximately 25° C.

Approximately 10 µg of genomic DNA was used for each restriction digest. DNA was digested with restriction enzymes according to the manufacturer's recommendations (Boehringer Mannheim, Indianapolis, Ind.). DNA was separated on TAE gels (0.04 M Tris-acetate, 0.001 M EDTA) containing 0.8% agarose. Southern blotting (Southern, 1975) was performed using Magnacharge™ membrane (Micron Separations Inc., Westborough, Mass.) and the DNA was cross-linked to the membrane using UV light and membranes were baked for 2 hrs. in a vacuum oven at 80° C.

Example 9

Copy Number and Integrity of the Mutant EPSPS Transgene in GA21

Figure 5A:
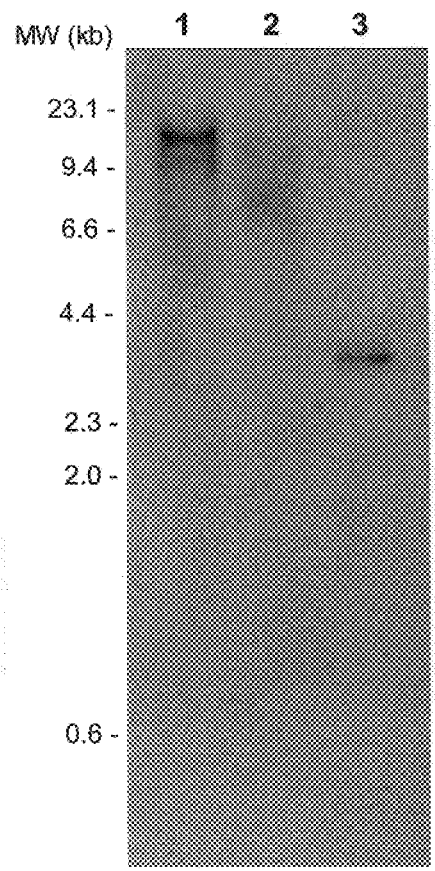
FIGS. 5A and 5B. (Scanned image) Southern blot analysis to determine the number of transgene insertions in GA21. A: Lane 1 contains GA21 DNA digested with EcoRV. Lane 2 contains non-transformed control DNA digested with EcoRV. Lane 3 contains pDPG434 digested with NotI. The blot was probed with the 3.4 kb NotI fragment from pDPG434. B: The blot shown in A was stripped and reprobed with a 324 bp fragment of the mutant EPSPS gene.

Corn line GA21 was analyzed to determine the number of insertions of the pDPG434 NotI EPSPS fragment used for transformation. GA21 genomic DNA was digested with a restriction enzyme that does not cut within the NotI EPSPS fragment used for transformation and probed with the entire NotI EPSPS fragment. For this analysis, GA21 DNA and nontransformed control DNAs were digested with EcoRV and probed with the NotI EPSPS fragment from pDPG434. NotI digested pDPG434 was included as a positive control at the level of approximately one copy per genome. For GA21, a single band of approximately 15 kb hybridized to the probe, indicating that a single insertion of the plasmid DNA fragment used for transformation had occurred (FIG. 5A). Some additional hybridization was observed in GA21 and nontransformed control DNA; this result was expected given that the probe used contained the transit peptide sequence (which includes maize DNA) and the mutant maize EPSPS gene. Both of these sequences are expected to hybridize to nontransformed maize DNA due to the presence of endogenous sequences with homology to the probe sequence.

Figure 5B:
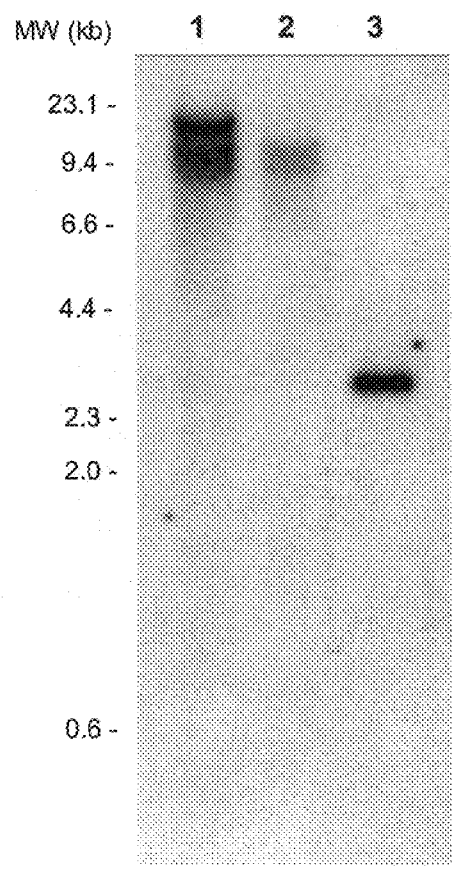

To further clarify the presence of a single insertion of the pDPG434 plasmid fragment in GA21, the probe was removed from the blot shown in FIG. 5A and the blot was rehybridized using a small DNA fragment internal to the mutant EPSPS gene. The 324 bp EPSPS probe hybridized strongly to the same approximately 15 kb band in GA21 DNA, indicating the presence of a single insertion of the NotI EPSPS fragment used for transformation (FIG. 5B).

Using the 324 bp EPSPS probe, hybridization to two smaller molecular weight bands was observed in both GA21 and nontransformed control DNA, indicating the presence of endogenous copies of the native EPSPS gene.

Figure 6:
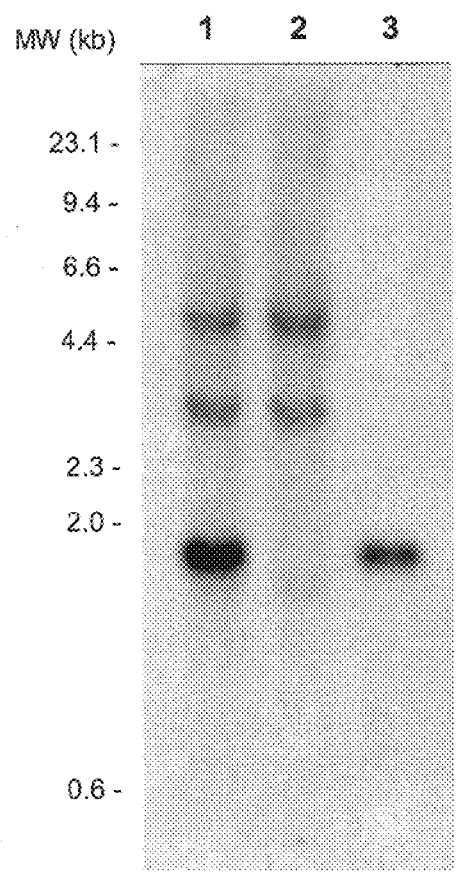
FIG. 6. (Scanned image) Southern blot analysis to estimate the copy number and integrity of the mutant EPSPS Gene. Lane 1 contains GA21 DNA digested with EcoRI/XbaI. Lane 2 contains nontransformed control DNA digested with EcoRI/XbaI. Lane 3 contains pDPG434 digested with EcoRI/XbaI. The blot was probed with the 324 bp EPSPS gene PCR fragment.

To determine if the mutant EPSPS gene in glyphosate resistant corn line GA21 was intact and to estimate copy number, genomic DNA from a GA21 transformant, nontransformed control DNA, and pDPG434 were digested with EcoRI/XbaI and probed with the 324 bp EPSPS probe. This restriction enzyme digest releases a fragment of approximately 1.8 kb from pDPG434 that contains the OTP sequence and the mutant EPSPS gene (FIG. 3). EcoRI/XbaI digested pDPG434 was run on the gel to approximate one copy of the EcoRI/XbaI OTP-EPSPS sequence per genome. The 324 bp mutant EPSPS probe was found to hybridize to an approximately 1.8 kb fragment in GA21 and the pDPG434 digests, but not in the digest of nontransformed control DNA (FIG. 6). This result demonstrates that the 1.8 kb OTP-EPSPS fragment present on pDPG434 is intact in glyphosate resistant corn line GA21. Comparison of the hybridization intensity of the pDPG434 digest to the digest of GA21 DNA indicates the presence of approximately two copies of the OTP-EPSPS sequence in GA21 (FIG. 6).

Example 10

Lack of Plasmid Backbone Sequences in GA21

Figure 7:
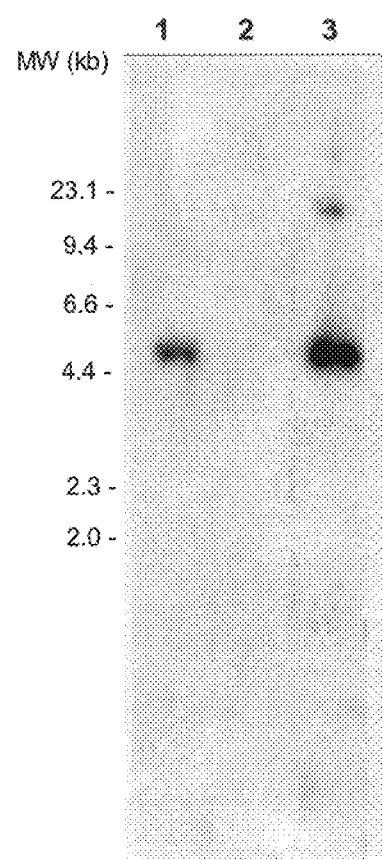
FIG. 7. (Scanned image) Southern blot analysis to confirm the lack of plasmid backbone sequence in GA21. Genomic DNA of a bla gene transformed plant (lane 1), a GA21 plant (lane 2), and plasmid DNA of pDPG427 was digested with BglII. The blot was probed with a 1.7 SspI/AflIII kb fragment from pBluescript SK(−) that contains the ColE1 origin of replication and the bla gene FIGS. 8A and 8B. Effect of glyphosate application on the growth and fertility of DK580 and DK626 BC$_4$ hybrids of GA21, FI117, GG25 and GJ11 transformation events. Treatments consisted of glyphosate applications at the 0×, 1× and 4× rates (1×X=16 ounces of Roundup Ultra™/acre). Mean ELH (extended leaf height in centimeters) was measured 10 days after glyphosate application. A. Effects of glyphosate application at the V4 stage of development. B. Effects of glyphosate application at the V8 stage of development.
Figure 10:
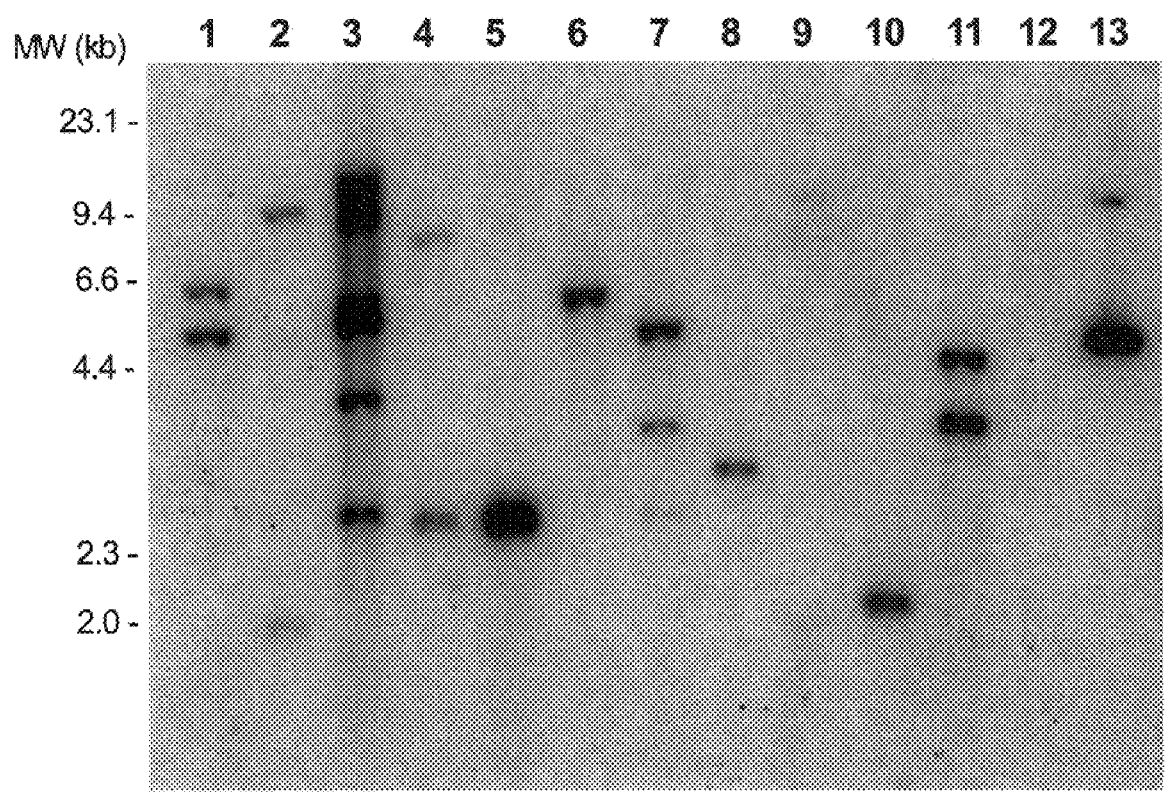
FIG. 10. (Scanned image) Southern blot analysis to detect transgene insertions GA21. FI117. GG25 and GJ11. Southern blot of BglII digested genomic DNA (lanes 2,5,10,11,12) and plasmid DNA (lane 13). Blot was probed with the 0.27 kb nos 3' polyadenlylation region from the nopaline synthase gene of Agrobacterium tumefaciens (Bevan, 1984). Lanes 2, 5, 10 and 11 contain genomic DNA from plants having the FI117, GA21, GG25 and GJ11 transformation events, respectively. Lane 12 contains negative control DNA from a non-transformed maize plant and lane 13 contains pDPG427 plasmid DNA.
Figures 11A, 11B:
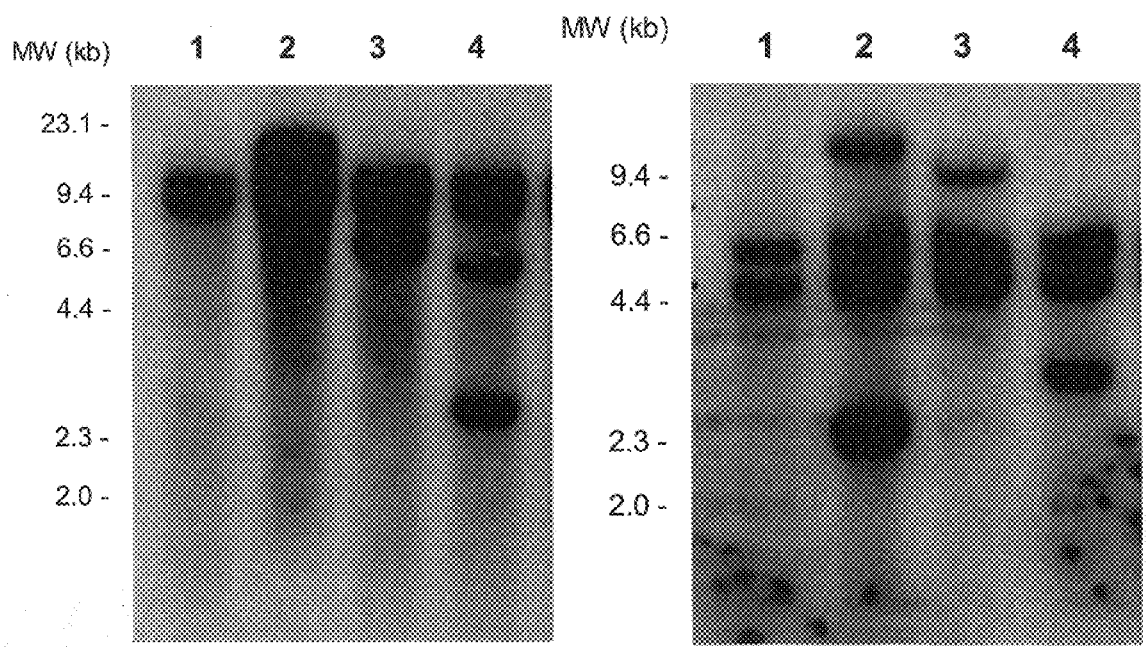
FIGS. 11A, 11B and 11C: (Scanned image) Southern blot analysis to detect transgene insertions GA21, GG25 and GJ11 using various restriction enzymes. Genomic DNA of a non-transformed control plant (lane 1) as well as GA21, GG25 and GJ11 (lanes 2, 3 and 4, respectively) transformation event containing plants was digested with various restriction enzymes and probed with a PCR generated 324 bp fragment of the EPSPS gene (see example 8 for generation of EPSPS fragment). DNA was digested with EcoRI (FIG. 11A), SphI (FIG. 11B) and SacI.
Figure 11C:
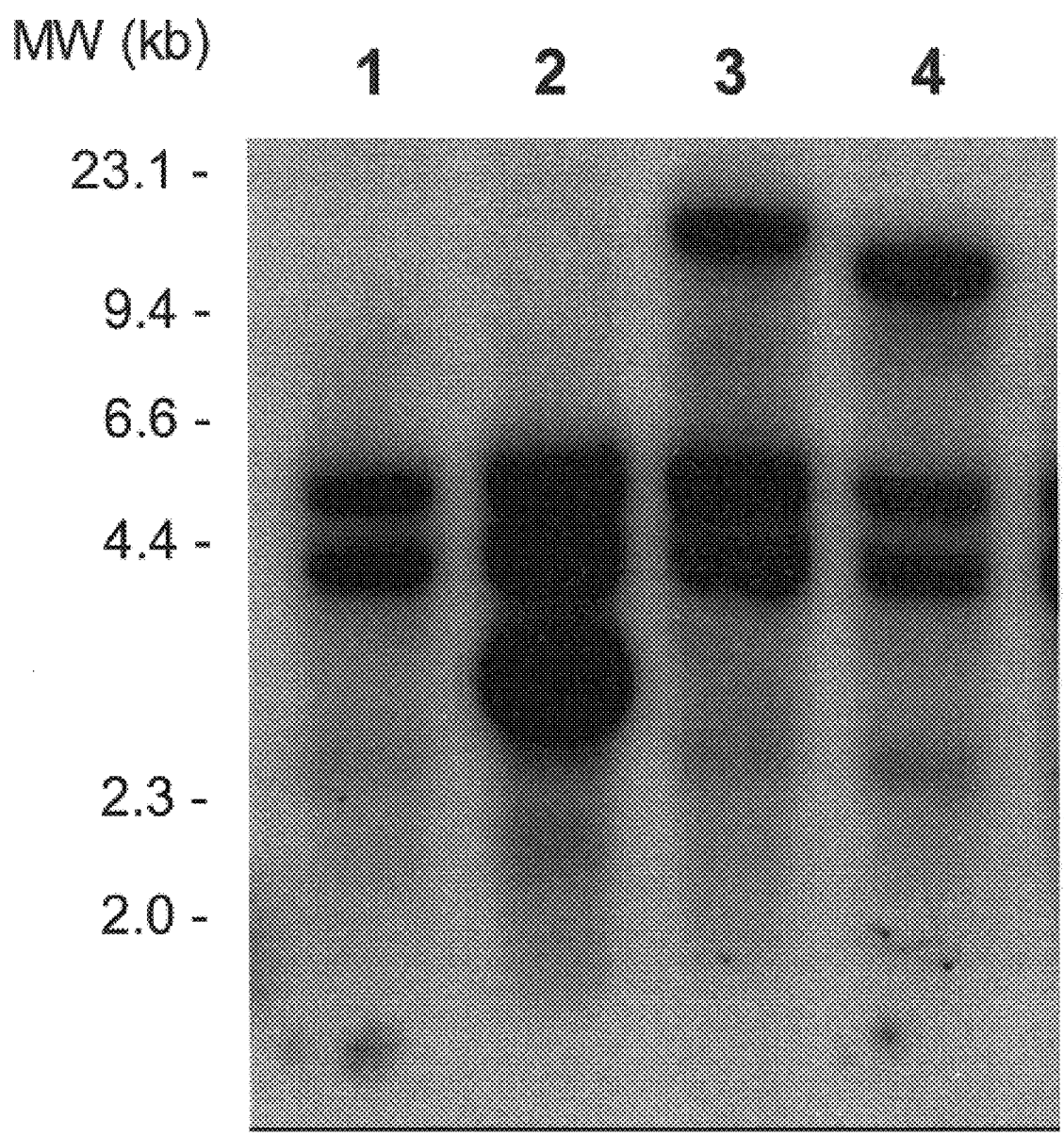

To confirm the lack of plasmid backbone sequences containing the ColE1 origin of replication and the bla gene encoding β-lactamase, DNA from a transgenic corn line containing a single copy of bla, DNA from a GA21 plant, and plasmid DNA were digested with BglII and probed with a 1.7 kb SspI/AflIII fragment from pBluescript SK(−) (Stratgene, La Jolla, Calif.) containing ColE1 and bla. The plasmid used, pDPG427, is identical to pDPG434 but contains a maize histone promoter instead of the rice actin promoter. As expected, no hybridization to the GA21 DNA was observed. Also as expected, hybridization to an approximately 5 kb band in the DNA from the bla-positive plant and from pDPG427 was observed (FIG. 7).

Example 11

Construction of Plasmids pDPG165, pDPG434 and pDPG443

DNA segments encoding the bar gene were constructed into plasmid pDPG165 (FIG. 1) essentially as described in U.S. patent application Ser. No. 08/113,561, filed Aug. 25, 1993, which is specifically incorporated herein by reference in its entirety. The bar gene was cloned from *Streptomyces hygroscopicus* (White et al., 1990) and exists as a 559-bp SmaI fragment in the plasmid pIJ4101. The sequence of the coding region of this gene is identical to that published (Thompson et al., 1987). To create plasmid pDPG165, the SmaI fragment from pIJ4104 was ligated into a pUC19-based vector containing the Cauliflower Mosaic Virus (CaMV) 35S promoter (derived from pBI221.1. provided by R. Jefferson, Plant Breeding Institute, Cambridge, England), a polylinker, and the transcript 7 (Tr7) 3' end from *Agrobacterium tumefaciens* (3' end provided by D. Stalker, Calgene, Inc., Davis, Calif.).

Figure 14:
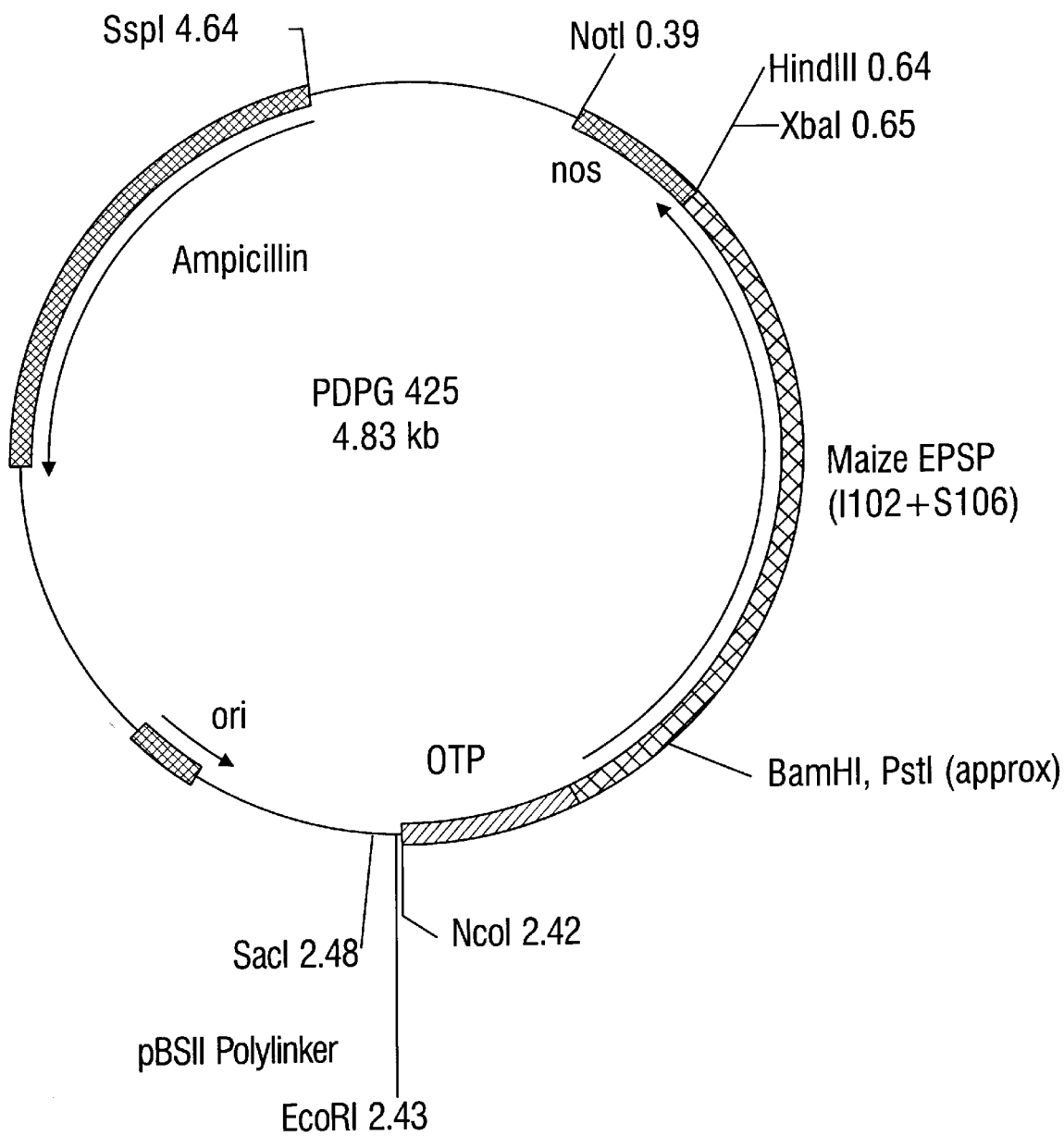
FIG. 14. Plasmid map of pDPG425. Major components and restriction sites are shown and locations are indicated in kilobase pairs.
Figure 15:
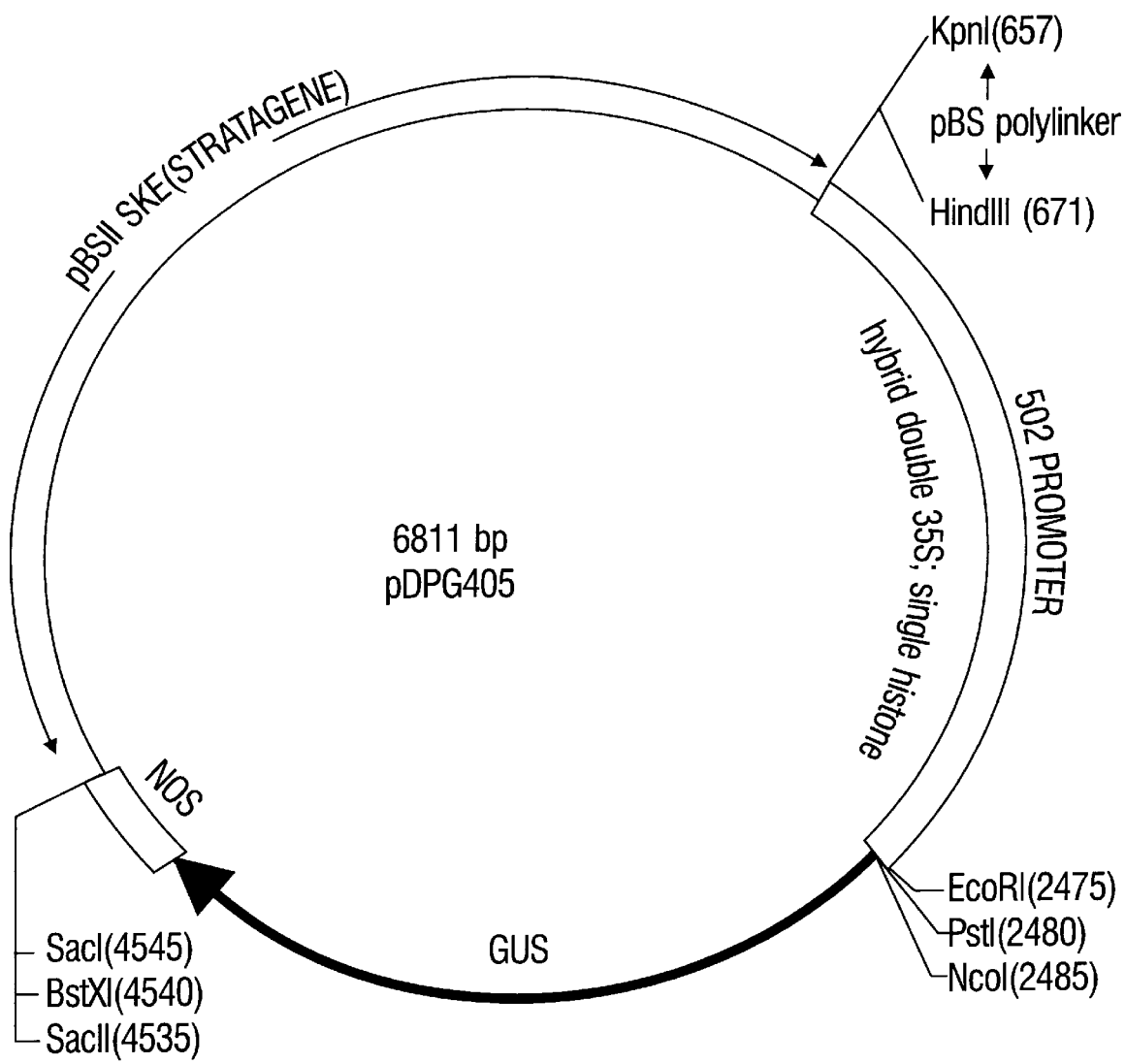
FIG. 15. Plasmid map of pDPG405. Major components and restriction sites are shown and locations are indicated in base pairs.

The plasmids pDPG434 (FIG. 3) and pDPG443 (FIG. 4) were constructed by cloning the respective promoters into SmaI-linearized pDPG425 (FIG. 14). Linearized vectors were treated with calf alkaline phosphatase to prevent recircularization prior to ligation. The rice actin promoter and intron were isolated as a 1.5 kb HindIII fragment from pDPG421 (pDM302; Cao et al., Plant Cell Rep (1992) 11:586–591). The 2× 35S/Arabidopsis histone promoter was isolated as a 1.8 kb EcoRI/HindIII fragment from pDPG405 (FIG. 15). The above mentioned promoter fragments were $T_4$ DNA polymerase-treated to create blunt ends prior to ligation into SmaI linearized pDPG425 (Rhone Poulenc Agrochimie). The fourth plasmid used, pDPG427 (FIG. 2), was obtained from Rhone Poulenc Agrochimie. A list of plasmids used in the current invention as well as the components of the plasmids is given in Table 4. A list of components of pDPG434 is shown in Table 5.

Example 12

Effect of Glyphosate Application on the Growth and Fertility of DK580 and DK626 Hybrids of FI117, GA21, GG25 and GJ11

$BC_4$ hybrids of DK580 and DK626 were produced containing one of the FI117, GA21, GG25 or GJ11 transformation events as described in example 14. Comparisons of the effect of glyphosate application on growth (mean extended leaf height) and male fertility was compared at both the V4 and V8 developmental stage. The developmental scale that was used to rate the corn plants is well known in the art, and is described in Special Report No. 48, Iowa State University of Science and Technology, Cooperative Extension Service, Ames, Iowa. Each of the hybrids was studied at both the V4 and V8 stage using 0× glyphosate (i.e. water only), 1× glyphosate, or 4× glyphosate (the 1× level corresponds to 16 ounces/acre of Roundup Ultra™).

Tests were designed as four row, 3 rep., split-split-plot with main plots as hybrids, subplots as transformant sources (i.e. GA21, GG25, FI117, and GJ11) and subplots as timing/ rate combinations (FIG. 12). Statistical methods for design and analysis of data derived from experimental field plots are described in Gomez and Gomez, (1984). Tests were conducted in Dekalb, Ill., and Thomasboro, Ill. during 1996. All rows were planted at double normal planting density, i.e., 60 seeds per row, because hybrids segregated 1:1 for the glyphosate resistance trait. Sprayed plants were thinned to 30 plants per row no sooner than 7 days after application of Roundup at a time when Roundup susceptible plants could be identified. Unsprayed plots were thinned to 30 plants per row at the same time. At 5–10 days after herbicide application, the following data was collected in each row: number of dead plants, number of damaged plants, and number of normal plants. After thinning, the mean extended leaf height was measured on 10 resistant plants per plot. During the remainder of the growing season the following agronomic data was collected: early stand count, seedling vigor, final stand count, plant height, ear height, intactness, stay green, number of barren plants, number of male-sterile plants, number of dropped ears, number of root lodged plants, number of stalks lodged plants, shelled grain weight, per cent grain moisture at harvest, and test weight.

The results show that all 4 transformation events gave significant resistance to glyphosate at both the 1× and 4× application levels (FIGS. 7A, 7B). Overall, the GA21 transformation event yielded the most efficacious resistance, in that at the 4× application level, 3 of the 4 GA21 treatments (FIGS. 7A, 7B) had the greatest mean extended leaf heights. Additionally, all 4 of the GA21 treatments yielded male fertile plants. At the V8 stage of application, only GJ11 and GJ25 treatments yielded male sterile plants (FIG. 8B), while at the V4 stage of application all plants were male fertile (FIG. 8A).

Example 13

Yield Effect of Glyphosate Application on DK580 and DK626 Hybrids of FI117, GA21, GG25 and GJ11 Transformation Events Four DK580 and four DK626 hybrids, each containing a different mutant EPSPS transgene from one of the GA21, FI117, GJ11 or GG25 transformation events, were field tested for possible effects on yield with glyphosate application as described in Example 12, with treatments as shown in FIG. 12. Hybrids were produced as described in example 14.

Yield estimates were computed using shelled grain weights, adjusted to 15.5% moisture. Data were analyzed using the SAS PROC MIXED and PROC SUM procedures. Only hybrids to which no glyphosate was applied were compared in order to remove any effects of herbicide application rates and/or weed competition on grain yield. The discussion herein will concentrate on results relating to grain yield.

FIG. 9A shows that when glyphosate is applied at the V4 stage, significant decreases in yield are not observed for 3 of the 4 DK580 hybrids. Further, in the case of the GA21 transformation event, the treatment group had a higher yield, although the difference was not found to be statistically significant. The differences in yield between DK580 hybrids with the introgressed mutant EPSPS transformation event relative to the hybrid without the event was significant only for the FI117 event. In this case, the glyphosate resistant hybrid had a higher yield than the corresponding non-resistant hybrid. The results demonstrate that glyphosate may be applied to three of the four DK580 hybrids at the V4 developmental stage without a corresponding decrease in yield.

Comparisons of the effect of glyphosate application on yield in each of the DK626 hybrids at the V8 developmental stage are given in FIG. 9B. The results demonstrate that even at the V8 stage, no significant loss in yield is observed upon a 4× rate of glyphosate application in either the GA21 or the FI117 introgressed DK626 hybrid. Further, the GA21 hybrid again realized a gain in yield relative to untreated controls of the same genetic background.

Example 14

Introgression of GA21, FI117, GG25, and GJ11 Into Elite Inbreds and Hybrids of Maize Backcrossing can be used to improve an inbred plant. Backcrossing transfers a specific desirable trait from one inbred source to an inbred that lacks that trait. This can be accomplished, for example, by first crossing a superior inbred (A) (recurrent parent) to a donor inbred (non-recurrent parent), which carries the appropriate gene(s) for the trait in question. The progeny of this cross are first selected in the resultant progeny for the desired trait to be transferred from the non-recurrent parent, then the selected progeny are mated back to the superior recurrent parent (A). After five or more backcross generations with selection for the desired trait, the progeny are hemizygous for loci controlling the characteristic being transferred, in this case a mutant EPSPS transgene, but are like the superior parent for most or almost all other genes. The last backcross generation would be selfed to give progeny which are pure breeding for the gene(s) being transferred, i.e. a GA21, GG25, GJ11, and/or FI117 transformation event.

Therefore, through a series a breeding manipulations, a selected gene encoding a mutant EPSPS may be moved from one corn line into an entirely different corn line without the need for further recombinant manipulation. Introduced transgenes are valuable in that they behave genetically as any other corn gene and can be manipulated by breeding techniques in a manner identical to any other corn gene. Exemplary procedures of this nature have been successfully carried out by the inventors. In these backcrossing studies, the transformants GA21, FI117, GG25, and GJ11 were each introgressed into the elite inbred lines FBLL (U.S. patent application Ser. No. 08/181,708, filed Jan. 14, 1994) and NL054B (U.S. patent application Ser. No. 08/595,549, filed Feb. 6, 1996) by backcrossing, although conversion to many more inbreds is currently in progress. Using these inbreds as female parents, two such exemplary hybrids were produced, DK626 and DK580. These hybrids were field tested for yield and other agronomic characteristics as well as herbicide tolerance.

The elite inbreds FBLL and NL054B were each backcrossed four times to the GA21, FI117, GJ11 and GG25 transformants. At each backcross generation plants containing the mutant EPSPS gene were identified based on resistance to a 1× application of glyphosate. Following four generations of backcrossing to a recurrent elite inbred parent, it is anticipated that the transformed line will be present in a genetic background that is at least 93% identical to the recurrent parent (FBLL or NL054B). Following backcross conversion, the plants were self-pollinated twice in order to identify plants homozygous for the introgressed gene of interest, i.e., the GA21, FI117, GJ11 and GG25 insertion events. Hybrids were produced by crossing the FBLL and NL054B inbred parents, which contained an insertion event of the GA21, FI117, GJ11 or GG25, to a non-transformed inbred male parent. DK580 hybrids were produced by a cross of FBLL to MBZA (U.S. patent application Ser. No. 08/182,616, filed Jan. 14, 1994) and DK626 hybrids were produced by a cross of NL054B by MM402A (U.S. patent application Ser. No. 08/181,019, filed Jan. 13, 1994), thereby yielding hybrids which were hemizygous for the respective transformation event.

Example 15

Marker Assisted Breeding

The identification of maize lines that are bred for increased glyphosate resistance may be readily assisted by using a mutant EPSPS gene integration event from the GA21, GG25, FI117 or GJ11 transformation events. Techniques for isolating nucleic acids and proteins are well known to those of skill in the art (Sambrook et al., 1989), and may be used in conjunction with the integration events of the present invention to selectively segregate plants that have increased glyphosate resistance.

It is contemplated that mutant EPSPS gene integration events will be useful as DNA probes for marker assisted breeding. In the process of marker assisted breeding DNA sequences are used to follow desirable agronomic traits (Tanksley et al., 1989) in the process of plant breeding. Therefore, assays which indicate the presence mutant EPSPS integration events of the current invention can be used for identification of plants with enhanced glyphosate resistance.

Marker assisted breeding using a mutant EPSPS gene integration event is undertaken as follows. Seed of plants with desired yield are planted in soil in the greenhouse or in the field. Leaf tissue is harvested from the plant for preparation of DNA at any point in growth at which approximately one gram of leaf tissue can be removed from the plant without compromising the viability of the plant. Genomic DNA is isolated using procedure modified from Shure et al. (1983). Approximately one gram of leaf tissue from a seedling is lypholyzed overnight in 15 ml polypropylene tubes. Freeze-dried tissue is ground to a power in the tube using a glass rod. Powdered tissue is mixed thoroughly with 3 ml extraction buffer (7.0 urea, 0.35 M NaCl, 0.05 M Tris-HCI ph 8.0, 0.01 M EDTA, 1% sarcosine). Tissue/buffer homogenate is extracted with 3 ml phenol/chloroform. The aqueous phase is separated by centrifugation, and precipitated twice using 1/10 volume of 4.4 M ammonium acetate pH 5.2, and an equal volume of isopropanol. The precipitate is washed with 75% ethanol and resuspended in 100–500 µl TE (0.01 M Tris-HCI, 0.001 M EDTA, pH 8.0). Genomic DNA is digested with a 3-fold excess of restriction enzymes, electrophoresed through 0.8% agarose (FMC), and transferred (Southern, 1975) to Nytran (Schleicher and Schuell) using 10× SCP (20 SCP: 2M NaCl, 0.6 M disodium phosphate, 0.02 M disodium EDTA).

One of skill in the art will recognize that many different restriction enzymes will be useful and the choice of restriction enzyme will depend on the DNA sequence of the mutant EPSPS gene integration event that is used as a probe and the DNA sequences in the maize genome surrounding the mutant EPSPS gene integration event. For a probe, one will want to use DNA or RNA sequences which will hybridize to DNA from the plasmid DNA of the integration event. The transformation event—plasmid combinations used herein are, for example, GA21-pDPG434, GG25-pDPG427, GJ11-pDPG443, and FI117-pDPG434 and pDPG165. One will select a restriction enzyme that produces a DNA fragment following hybridization that is identifiable as that mutant EPSPS gene integration event.

It is expected that one or more restriction enzymes will be used to digest genomic DNA either singly or in combinations. Filters are prehybridized in 6× SCP, 10% dextran sulfate, 2% sarcosine, and 500 µg/ml denatured salmon sperm DNA and $^{32}$P-labeled probe generated by random priming (Feinberg & Vogelstein, 1983). Hybridized filters are washed in 2× SCP, 1% SDS at 65° for 30 minutes and visualized by autoradiography using Kodak XAR5 film. Those of skill in the art will recognize that there are many different ways to isolate DNA from plant tissues and that there are many different protocols for Southern hybridization that will produce identical results. Those of skill in the art will recognize that a Southern blot can be stripped of radioactive probe following autoradiography and re-probed with a different mutant EPSPS gene integration event probe. In this manner one may identify each of the various mutant EPSPS gene integration events that is present in the plant.

Each lane of the Southern blot represents DNA isolated from one plant. Through the use of multiplicity of mutant EPSPS gene integration events as probes on the same genomic DNA blot, the integration event composition of each plant may be determined. Correlations are established between the contributions of particular integration events to increasing the herbicide resistance of the plant. Only those plants that contain the desired combination of integration events are advanced to maturity and used for pollination. DNA probes corresponding to mutant EPSPS gene integration events are useful markers during the course of plant breeding to identify and combine particular integration events without having to grow the plants and assay the plants for agronomic performance.

Example 16

General Methods for Assays

DNA analysis was performed as follows. Genomic DNA was isolated using a procedure modified from Shure, et al., 1983. Approximately 1 gm callus tissue was ground to a fine powder in liquid nitrogen using a mortar and pestle. Powdered tissue was mixed thoroughly with 4 ml extraction buffer (7.0 M urea, 0.35 M NaCl, 0.05 M Tris-HCl pH 8.0, 0.01 M EDTA, 1% sarcosine). Tissue/buffer homogenate was extracted with 4 ml phenol/chloroform. The aqueous phase was separated by centrifugation, passed through Miracloth, and precipitated twice using 1/10 volume of 4.4 M ammonium acetate, pH 5.2 and an equal volume of isopropanol. The precipitate was washed with 70% ethanol and resuspended in 200–500:1 TE (0.01 M Tris-HCl, 0.001 M EDTA, pH 8.0). Plant tissue may also be employed for the isolation of DNA using the foregoing procedure.

The presence of a gene in a transformed cell may be detected through the use of polymerase chain reaction (PCR). Using this technique specific fragments of DNA can be amplified and detected following agarose gel electrophoresis. For example the mutant EPSPS gene may be detected using PCR. Two hundred to 1000 ng genomic DNA is added to a reaction mix containing 10 mM Tris-HCl pH 8.3, 1.5 mM MgCl$_2$, 50 mM KCl, 0.1 mg/ml gelatin, 200 µM each dATP, dCTP, dGTP, dTTP, 0.5 µM each forward and reverse DNA primers, 20% glycerol, and 2.5 units Taq DNA polymerase. The primer sequences are (upper) 5'-TTTGGCTCTTGGGGATGTG-3' and (lower) 5'-TTACGCTAGTCTCGGTCCAT-3'. The reaction is run in a thermal cycling machine as follows: 3 minutes at 94 C., 39 repeats of the cycle 1 minute at 94 C., 1 minute at 50 C., 30 seconds at 72 C., followed by 5 minutes at 72 C. Twenty µl of each reaction mix is run on a 3.5% NuSieve gel in TBE buffer (90 mM Tris-borate, 2 mM EDTA) at 50V for two to four hours. Using these primers a 324 base pair fragment of the mutant EPSPS transgene is amplified.

For Southern blot analysis genomic DNA was digested with a 3-fold excess of restriction enzymes, electrophoresed through 0.8% agarose (FMC), and transferred (Southern, 1975) to Nytran (Schleicher and Schuell) using 10× SCP (20× SCP: 2 M NaCl, 0.6 M disodium phosphate, 0.02 M disodium EDTA). Filters were prehybridized at 65° C. in 6× SCP, 10% dextran sulfate, 2% sarcosine, and 500 µg/ml heparin (Chomet et al., 1987) for 15 min. Filters were hybridized overnight at 65 C. in 6× SCP containing 100 µg/ml denatured salmon sperm DNA and 32P-labeled probe. Filters were washed in 2× SCP, 1% SDS at 65 C. for 30 min. and visualized by autoradiography using Kodak XAR5 film. For rehybridization, the filters were boiled for 10 min. in distilled H$_2$O to remove the first probe and then prehybridized as described above.

Example 17

Weed Control in Agricultural Fields of Glyphosate Resistant Maize Plants

Roundup™ is a commercial formulation of glyphosate manufactured and sold by the Monsanto Company. The amount of Roundup™ (glyphosate) which is applied to an agricultural field in which glyphosate resistant maize plants grow depends on the particular weed or spectrum of weeds present in the field and for which control is desired. Herbicide application rates may typically range from four ounces of Roundup™ to 256 ounces Roundup™ per acre (the 1× rate is equivalent to 16 ounces per acre of Roundup™, i.e., 64 ounces/acre is 4×). Preferably, from 8 ounces to 128 ounces per acre of Roundup™ are applied to an agricultural field in which glyphosate resistant maize plants are present. More preferably, from about 16 ounces to about 64 ounces per acre of Roundup™ may be applied to the field. An application of Roundup™ in excess of the 1× rate, including 1×, 2×, 3×, 4× and greater, is sufficient to kill maize plants which do not have an expressed copy of the mutant EPSPS gene, and will additionally kill a wide spectrum of weeds.

An initial field application of glyphosate is typically carried out between about the V3 to V5 stages of development and will typically consist of about a 2× application. The application rate may be increased or decreased as needed, based on the abundance and/or type of weeds being treated. Depending on the location of the field and weather conditions, which will influence weed growth and the type of weed infestation, it may be desirable to conduct further glyphosate treatments. The second glyphosate application will typically consist of about a 2× glyphosate application made between the V6 and V8 stage of maturity. Again the treatment rate may be adjusted based on field conditions. Such methods of application of herbicides to agricultural crops are well known in the art and are summarized in general in Anderson, (1983).

A farmer may also apply a combination of herbicides including Roundup™, to a field in which glyphosate resistant maize plants are present. Combination of herbicides are referred to as "tank mixes." A second herbicide is supplied in combination with Roundup™ in order to complement the activity of Roundup™ and thereby increase the efficiency of weed control. For example, Roundup™ may be applied to a field of glyphosate resistant maize plants in conjunction with a herbicide with residual activity, such as a triazine herbicide, in order to provide longer lasting weed control. One herbicide which may be particularly useful in mixture with glyphosate is acetochlor. It is contemplated that Roundup™ may be applied to an agricultural field comprising glyphosate resistant maize plants in conjunction with one or more of the herbicides listed in Table 1. It is understood that the list of herbicides in Table 1 is not limiting and one of skill in the art will know the identity of other herbicidal chemicals which a farmer could apply to a field in combination with Roundup™.

A farmer may wish to apply glyphosate to a field for weed control at any time during the growth of the corn plant at which time the farmer desires to control weed growth. Preferably, glyphosate is applied to the field during vegetative growth of the maize plants, i.e., prior to the onset of flowering. Roundup™ may be applied to glyphosate resistant plants in the field at any stage of development, including between the V1 and V10 stages (the developmental scale is described in, "How a Corn Plant Grows", Special Report No. 48, Iowa State University of Science and Technology, Cooperative Extension Service, Ames, Iowa) of vegetative growth. More preferably, Roundup™ is applied to the field at the V2, V3, V4, V5, V6, V7 or V8 stages of vegetative growth, and most preferably at the V4, V5, V6, V7 or V8 stages of growth of the maize plant. Further, multiple applications of Roundup™ may be desired in order to control weed growth. For example, Roundup™ may be applied to the field at both the V4 stage of growth of the glyphosate resistant maize plant and at the V8 stage of growth. Furthermore, Roundup™ may be applied on an as needed basis in order to control growth of particular weeds when required.

REFERENCES

The references listed below are incorporated herein by reference to the extent that they supplement, explain, provide a background for, or teach methodology, techniques, and/or compositions employed herein.

PCT Application No. WO 89/06700
PCT Application PCT/US89/01025
PCT Application WO 88/10315
PCT No. WO 91/02071
PCT/US87/00880
U.S. Pat. No. 4,769,061
U.S. Pat. No. 4,535,060
U.S. Pat. No. 4,683,195
U.S. Pat. No. 4,683,202
U.S. Pat. No. 4,800,159
U.S. Pat. No. 4,883,750
U.S. Pat. No. 5,279,721
U.S. Pat. No. 5,384,253
U.S. Pat. No. 5,384,956
U.S. Pat. No. 5,463,175
U.S. Pat. No. 5,554,798
U.S. Pat. No. 5,591,616
U.S. patent application Ser. No. 08/113,561, filed Aug. 25, 1993
U.S. patent application Ser. No. 08/181,019, filed Jan. 13, 1994
U.S. patent application Ser. No. 08/182,616, filed Jan. 14, 1994
U.S. patent application Ser. No. 08/181,708, filed Jan. 14, 1994
U.S. patent application Ser. No. 08/595,549, filed Feb. 6, 1996
Anderson, W. P., Weed Science Principles, West Publishing Company, 1983.
Balthazor and Hallas, "Glyphosate-degrading microorganisms from industrial activated sludge," *Appl. Environ. Microbiol.,* 51:432–434, 1986.
Bevan, "Binary Agrobacterium vectors for plant transformation," *Nucleic Acids Res.,* 12:8711–8721, 1984.
Bevan et al., *Nucleic Acid Research,* 11:369–385, 1983.
Callis et al., *Genes and Develop.,* 1:1183–1200, 1987.
Cao et al., *Plant Cell Rep,* 11:586–591, 1992.
Capaldi et al., *Biochem. Biophys. Res. Comm.,* 76:425, 1977
Chomet et al., 1987 EMBO J 6:295–302.
Chu et al., *Scientia Sinica,* 18:659–668, 1975.
Clark, *J. of Plant Nutrition,* 5:1039, 1982.
Comai et al., *Nature,* 317:741–744, 1985.
Coupland, "Metabolism of glyphosate in plants in The Herbicide Glyphosate," 25–34, 1985.
Cristou et al., *Plant Physiol,* 87:671–674, 1988.
Daughten et al., "Biodegradation of phosphonate toxicants yields methane or ethane on cleavage of the C—P bond," *FEMS Microbiol. Lett.,* 5:91–93, 1979b.
Daughton et al., "Bacterial conversion of alkylphosphonates to natural products via carbon-phosphorus bond cleavage," *J Agric. Food Chem.,* 27:1375–1382, 1979a.
Daughton et al., "Phosphate and soil binding: factors limiting bacterial degradation of ionic phosphorous-containing pesticide metabolites," *Appl. Environ. Microbiol.,* 37:605–609, 1979c.
De Block et al., *EMBO J.,* 6:2513–2518; see also PCT Publication number WO 87/05629, 1987.
De Block et al., *Plant Physiol,* 91:694–701, 1989.
Dellaporta et al., in Chromosome Structure and Function: Impact of New Concepts, 18th Stadler Genetics Symposium, J. P. Gustafson and R. Appels, eds (New York: Plenum Press), pp. 263–282, 1988.
Ellis et al., *EMBO Journal,* 6(11):3203–3208, 1987.
EPO No. 329 822
Feinberg and Vogelstein, *Anal Biochem,* 132:6–13, 1983.
Finkle et al., *Plant Sci,* 42:133–140, 1985.

Fodor et al., Light-directed, spatially addressable parallel chemical synthesis. *Science,* 251:767–773, 1991.

Fransz et al., *Plant Cell Rep,* 8:67–70, 1989.

Franz, "Discovery, development and chemistry of glyphosate," *The Herbicide Glyphosate,* 3–17, 1985.

Frohman, In: *PCR Protocols: A Guide to Methods and Applications,* 1990.

GB application 2 202 328

Gomez and Gomez, *Staistical Procedures for Agricultural Research,* John Wiley and Sons, 1984.

Hacia et al., Detection of heterozygous mutations in BRCA1 using high density oligonucleotide arrays and two-colour fluorescence analysis. *Nature Genetics,* 14:441–447, 1996.

Hallas et al., "Characterization of microbial traits associated with glyphosate biodegradation in industrial activated sludge," *J. Industrial Microbiol.,* 3:377–385, 1988.

Ingelbrecht et al., *The Plant Cell,* 1:671–680, 1989.

Jacob et al., "Metabolism of glyphosate in Pseudomonas sp. strain LBr," *Appl. Environ. Microbiol.,* 54:2953–2958, 1988.

Kishore and Jacob, "Degradation of glyphosate by Pseudomonas sp. PG2928 via a sarcosine intermediate," *J Biol. Chem.,* 262:12164–12168, 1987.

Klein et al., *Plant Physiol,* 91:440–444, 1989.

Kwoh et al., *Proc. Nat. Acad. Sci. USA,* 86: 1173, 1989.

Lebrun et al., "Molecular basis of resistance to shikimic herbicides in adapted maize cell cultures," 1991. Genbank Accession X63374.

Lebrun et al., "Chimeric gene for the transformation of plants," U.S. Pat. No. 5,510,471, 1996.

Liu et al., "Degradation of the herbicide glyphosate by members of the family Rhixobiaceae," *Environ. Microbiol.,* 57:1799–1804, 1991.

Maier, *Phosphorus Sulfur,* 14:295, 1983.

Marshall et al., *Pestic. Sci.,* 18:65–77, 1987.

Mastalerz et al., "Utilization of carbon-bound phosphorus by microorganisms," *Acta Biochim. Pol.,* 12:151–156, 1965.

Murakami, *Mol Gen Genet,* 205:42–50, 1986.

Murashige and Skoog, *Physiol Plant,* 15:473–497, 1962.

Odell et al., *Nature,* 313:810–812, 1985.

Ogawa et al, *Sci. Rep.,* 3:42–48, 1973.

Omirulleh et al., *Plant Molecular Biology,* 21:415–428, 1993.

Pease et al., Light-generated oligonucleotide arrays for rapid DNA sequence analysis. *Proc. Natl. Acad. Sci. USA,* 91:5022–5026, 1994.

Pipke and Amrhein, "Degradation of the phosphonate herbicide glyphosate by *Arthrobacter atrocyaneus* ATCC 13752," *Appl. Environ. Microbiol.,* 54:1293–1296, 1988.

Puite et al., *Plant Cell Rep.,* 4:274–276, 1985.

Sambrook et al., *Molecular Cloning, A Laboratory Manual,* 2nd ed., 1989.

Schowanek and Verstraete, "Phosphonate utilization by bacterial cultures and enrichments from environmental samples," *Appl. Environ. Microbiol.,* 56:895–903, 1990.

Shah et al., *Science,* 233:478–481, 1986.

Shinabarger and Braymer, "Glyphosate catabolism by Pseudomonas sp. strain PG2982," *J. Bacteriol.,* 168:702–707, 1986.

Shoemaker et al., Quantitative phenotypic analysis of yeast deletion mutants using a highly parallel molecular barcoding strategy. *Nature Genetics* 14:450–456, 1996.

Shure et al., *Cell,* 35:225–233, 1983.

Southern, "Detection of specific sequences among DNA fragments separated by gel electrophoresis," *J. Mol. Biol.,* 98: 503–517, 1975.

Spencer et al., *Plant Molecular Biology,* 18:201–210, 1992.

Sutcliffe, "Nucleotide sequence of the ampicillin resistance gene of *Escherichia coli* plasmid pBR322," *Proc. Natl. Acad. Sci., USA* 75: 3737–3741, 1978.

Tanaka et al., "Synthesis and pesticidal activities of phosphonate analogs of amino acids," *J. Fac. Agr. Kyushu Univ.,* 30:209–223, 1986.

Tanksley et al., 1989 Bio/Technolgy 7:257–264.

Thompson et al., *EMBO J,* 6:2519–2623, 1987.

Torstensson, "Behavior of glyphosate in soils and its degradation," *The Herbicide Glyphosate,* 137–150, 1985.

Walker et al., Proc. Nat'l Acad. Sci. USA, 89:392–396 1992.

Weidhase et al., "Utilization of glyphosate by Pseudomonas sp. GS," *Zentralbl. Mikrobiol.,* 145:6, 1990.

White et al., *Nucl Acids Res.,* 18:1062, 1990.

Withers and King, *Plant Physiol,* 64:675–678, 1979.

WO 90/07641

WO 95/06128

Wu et al., *Genomics,* 4:560, 1989.

Yanisch-Perron et al., "Improved M13 phage cloning vectors and host strains: nucleotide sequences of the M13mp18 and pUC19 vectors," *Gene,* 33:103–119, 1985.

Zeleznick et al., "Growth of *Escherichia coli* on methly— and ethylphosphonic acids," *Biochim. Biophys. Acta.,* 78:546–547, 1963.

---

We claim:

1. A fertile transgenic maize plant comprising a chromosomally integrated expression cassette comprising (i) a modified maize EPSPS gene encoding an EPSPS protein having isoleucine at position 102 and serine at position 106 and (ii) a promoter active in maize operably linked to said EPSPS gene, wherein the yield of said fertile transgenic maize plant is not affected by a glyphosate application rate that affects the yield of a maize plant lacking said modified maize gene, wherein said fertile transgenic maize plant comprises a transformation event selected from the group consisting of GA21, seed comprising said GA21 transformation event having been deposited as ATCC Accession Number 209033, FI117, seed comprising said FI117 transformation event having been deposited as ATCC Accession Number 209031, GG25, seed comprising said GG25 transformation event having been deposited as ATCC Accession Number 209032, and GJ11, seed comprising said GJ11 transformation event having been deposited as ATCC Accession Number 209030.

2. The maize plant of claim 1, wherein said promoter is selected from the group consisting of a rice actin promoter, a maize histone promoter and a fused CaMV 35S-Arabidopsis histone promoter.

3. The maize plant of claim 1, wherein the transformation event is GA21.

4. The maize plant of claim 1, wherein the transformation event is FI117.

5. The maize plant of claim 4, wherein said maize plant is further defined as comprising a bar gene.

6. The maize plant of claim 1, wherein the transformation event is GG25.

7. The maize plant of claim 1, wherein the transformation event is GJ11.

8. Progeny of a fertile transgenic maize plant comprising a chromosomally integrated expression cassette comprising (i) a modified maize EPSPS gene encoding an EPSPS protein having isoleucine at position 102 and serine at position 106 and (ii) a promoter active in maize operably linked to said EPSPS gene, wherein the yield of said progeny is not affected by a glyphosate application rate that affects the yield of a maize plant lacking said modified maize gene, wherein said fertile transgenic maize plant comprises a transformation event selected from the group consisting of GA21, seed comprising said GA21 transformation event having been deposited as ATCC Accession Number 209033, FI117, seed comprising said FI117 transformation event having been deposited as ATCC Accession Number 209031, GG25, seed comprising said GG25 transformation event having been deposited as ATCC Accession Number 209032, and GJ11, seed comprising said GJ11 transformation event having been deposited as ATCC Accession Number 209030.

9. Seeds of a fertile transgenic maize plant comprising a chromosomally integrated expression cassette comprising (i) a modified maize EPSPS gene encoding an EPSPS protein having isoleucine at position 102 and serine at position 106 and (ii) a promoter active in maize operably linked to said EPSPS gene, wherein the yield of said fertile transgenic maize plant is not affected by a glyphosate application rate that affects the yield of a maize plant lacking said modified maize gene, wherein said fertile transgenic maize plant comprises a transformation event selected from the group consisting of GA21, seed comprising said GA21 transformation event having been deposited as ATCC Accession Number 209033, FI117, seed comprising said FI117 transformation event having been deposited as ATCC Accession Number 209031, GG25, seed comprising said GG25 transformation event having been deposited as ATCC Accession Number 209032, and GJ11, seed comprising said GJ11 transformation event having been deposited as ATCC Accession Number 209030.

10. Seeds of the progeny of a fertile transgenic maize plant comprising a chromosomally integrated expression cassette comprising (i) a modified maize EPSPS gene encoding an EPSPS protein having isoleucine at position 102 and serine at position 106 and (ii) a promoter active in maize operably linked to said EPSPS gene, wherein the yield of said progeny is not affected by a glyphosate application rate that affects the yield of a maize plant lacking said modified maize gene, wherein said fertile transgenic maize plant comprises a transformation event selected from the group consisting of GA21, seed comprising said GA21 transformation event having been deposited as ATCC Accession Number 209033, FI117, seed comprising said FI117 transformation event having been deposited as ATCC Accession Number 209031, GG25, seed comprising said GG25 transformation event having been deposited as ATCC Accession Number 209032, and GJ11, seed comprising said GJ11 transformation event having been deposited as ATCC Accession Number 209030.

11. A method of preparing a fertile transgenic maize plant comprising:
  (i) providing an expression cassette comprising (a) a modified maize EPSPS gene encoding an EPSPS protein having isoleucine at position 102 and serine at position 106 and (b) a promoter active in maize operably linked to said EPSPS gene;
  (ii) contacting recipient maize cells with said expression cassette under conditions permitting the uptake of said expression cassette by said recipient cells;
  (iii) selecting recipient cells comprising a chromosomally incorporated expression cassette;
  (iv) regenerating plants from said selected cells; and
  (v) identifying a fertile transgenic maize plant, the yield of which is not affected by a glyphosate application rate that affects the yield of a maize plant lacking said modified maize gene, wherein said fertile transgenic maize plant comprises a transformation event selected from the group consisting of GA21, seed comprising said GA21 transformation event having been deposited as ATCC Accession Number 209033, FI117, seed comprising said FI117 transformation event having been deposited as ATCC Accession Number 209031, GG25, seed comprising said GG25 transformation event having been deposited as ATCC Accession Number 209032, and GJ11, seed comprising said GJ11 transformation event having been deposited as ATCC Accession Number 209030.

12. The method of claim 11, wherein said contacting comprises microprojectile bombardment, electroporation or Agrobacterium-medicate transformation.

13. The method of claim 11, wherein said selecting comprises treating recipient cells with glyphosate.

14. The method of claim 11, wherein said promoter is selected from the group consisting of a rice actin promoter, a maize histone promoter and a fused CaMV 35S-Arabidopsis histone promoter.

15. The method of claim 11, wherein the transformation event is GA21.

16. The method of claim 11, wherein the transformation event is FI117.

17. The method of claim 16, wherein said maize plant is further defined as comprising a bar gene.

18. The method of claim 11, wherein the transformation event is GG25.

19. The method of claim 11, wherein the transformation event is GJ11.

20. A fertile transgenic maize plant prepared according to a method comprising:
  (i) providing an expression cassette comprising (a) a modified maize EPSPS gene encoding an EPSPS protein having isoleucine at position 102 and serine at position 106 and (b) a promoter active in maize operably linked to said EPSPS gene;
(ii) contacting recipient maize cells with said expression cassette under conditions permitting the uptake of said expression cassette by said recipient cells;
(iii) selecting recipient cells comprising a chromosomally integrated expression cassette;
(iv) regenerating plants from said selected cells; and
(v) identifying a fertile transgenic maize plant, the yield of which is not affected by a glyphosate application rate that affects the yield of a maize plant lacking said modified maize gene, wherein said fertile transgenic maize plant comprises a transformation event selected from the group consisting of GA21, seed comprising said GA21 transformation event having been deposited as ATCC Accession Number 209033, FI117, seed comprising said FI117 transformation event having been deposited as ATCC Accession Number 209031, GG25, seed comprising said GG25 transformation event having been deposited as ATCC Accession Number 209032, and GJ11, seed comprising said GJ11 transformation event having been deposited as ATCC Accession Number 209030.

21. The maize plant of claim 20, wherein said promoter is selected from the group consisting of a rice actin promoter, a maize histone promoter and a fused CaMV 35S-Arabidopsis histone promoter.

22. The maize plant of claim 20, wherein the transformation event is GA21.

23. Progeny of a fertile transgenic maize plant prepared according to a method comprising:
(i) providing an expression cassette comprising (a) a modified maize EPSPS gene encoding an EPSPS protein having isoleucine at position 102 and serine at position 106 and (b) a promoter active in maize operably linked to said EPSPS gene;
(ii) contacting recipient maize cells with said expression cassette under conditions permitting the uptake of said expression cassette by said recipient cells;
(iii) selecting recipient cells comprising a chromosomally integrated expression cassette;
(iv) regenerating plants from said selected cells; and
(v) identifying a fertile transgenic maize plant, the yield of which is not affected by a glyphosate application rate that affects the yield of a maize plant lacking said modified maize gene, wherein said fertile transgenic maize plant comprises a transformation event selected from the group consisting of GA21, seed comprising said GA21 transformation event having been deposited as ATCC Accession Number 209033, FI117, seed comprising said FI117 transformation event having been deposited as ATCC Accession Number 209031, GG25, seed comprising said GG25 transformation event having been deposited as ATCC Accession Number 209032, and GJ11, seed comprising said GJ11 transformation event having been deposited as ATCC Accession Number 209030.

24. Seeds of a fertile transgenic maize plant, wherein said fertile transgenic maize plant is prepared according to a method comprising:
(i) providing an expression cassette comprising (a) a modified maize EPSPS gene encoding an EPSPS protein having isoleucine at position 102 and serine at position 106 and (b) a promoter active in maize operably linked to said EPSPS gene;
(ii) contacting recipient maize cells with said expression cassette under conditions permitting the uptake of said expression cassette by said recipient cells;
(iii) selecting recipient cells comprising a chromosomally integrated expression cassette;
(iv) regenerating plants from said selected cells; and
(v) identifying a fertile transgenic maize plant, the yield of which is not affected by a glyphosate application rate that affects the yield of a maize plant lacking said modified maize gene, wherein said fertile transgenic maize plant comprises a transformation event selected from the group consisting of GA21, seed comprising said GA21 transformation event having been deposited as ATCC Accession Number 209033, FI117, seed comprising said FI117 transformation event having been deposited as ATCC Accession Number 209031, GG25, seed comprising said GG25 transformation event having been deposited as ATCC Accession Number 209032, and GJ11, seed comprising said GJ11 transformation event having been deposited as ATCC Accession Number 209030.

25. Seeds of the progeny of a fertile transgenic maize plant, wherein said fertile transgenic maize plant is prepared according to a method comprising:
(i) providing an expression cassette comprising (a) a modified maize EPSPS gene encoding an EPSPS protein having isoleucine at position 102 and serine at position 106 and (b) a promoter active in maize operably linked to said EPSPS gene;
(ii) contacting recipient maize cells with said expression cassette under conditions permitting the uptake of said expression cassette by said recipient cells;
(iii) selecting recipient cells comprising a chromosomally integrated expression cassette;
(iv) regenerating plants from said selected cells; and
(v) identifying a fertile transgenic maize plant, the yield of which is not affected by a glyphosate application rate that affects the yield of a maize plant lacking said modified maize gene, wherein said fertile transgenic maize plant comprises a transformation event selected from the group consisting of GA21, seed comprising said GA21 transformation event having been deposited as ATCC Accession Number 209033, FI117, seed comprising said FI117 transformation event having been deposited as ATCC Accession Number 209031, GG25, seed comprising said GG25 transformation event having been deposited as ATCC Accession Number 209032, and GJ11, seed comprising said GJ11 transformation event having been deposited as ATCC Accession Number 209030.

26. A glyphosate resistant, inbred, fertile maize plant comprising a chromosomally integrated expression cassette comprising (a) a modified maize EPSPS gene encoding an EPSPS protein having isoleucine at position 102 and serine at position 106 and (b) a promoter active in maize operably linked to said EPSPS gene, wherein said inbred fertile maize plant comprises a transformation event selected from the group consisting of GA21, seed comprising said GA21 transformation event having been deposited as ATCC Accession Number 209033, FI117, seed comprising said FI117 transformation event having been deposited as ATCC Accession Number 209031, GG25, seed comprising said GG25 transformation event having been deposited as ATCC Accession Number 209032, and GJ11, seed comprising said GJ11 transformation event having been deposited as ATCC Accession Number 209030.

27. The maize plant of claim 26, wherein said promoter is selected from the group consisting of a rice actin promoter, a maize histone promoter and a fused CaMV 35S-Arabidopsis histone promoter.

28. The maize plant of claim 26, wherein the transformation event is GA21.

29. The inbred maize plant of claim 26, further defined as comprising a transformation event selected from the group consisting of GA21, GG25, GJ11 and FI117.

30. A glyphosate resistant, crossed fertile transgenic maize plant prepared according to the method comprising:
(i) obtaining a fertile transgenic maize plant comprising a chromosomally integrated expression cassette comprising (a) a modified maize EPSPS gene encoding an EPSPS protein having isoleucine at position 102 and serine at position 106 and (b) a promoter active in maize operably linked to said EPSPS gene;
(ii) crossing said fertile transgenic maize plant with a second maize plant lacking said expression cassette to obtain a third maize plant comprising said expression cassette; and
(iii) backcrossing said third maize plant to obtain a backcrossed fertile maize plant; wherein said modified EPSPS gene is inherited through a male parent, wherein said fertile transgenic maize plant comprises a transformation event selected from the group consisting of GA21, seed comprising said GA21 transformation event having been deposited as ATCC Accession Number 209033, FI117, seed comprising said FI117 transformation event having been deposited as ATCC Accession Number 209031, GG25, seed comprising said GG25 transformation event having been deposited as ATCC Accession Number 209032, and GJ11, seed comprising said GJ11 transformation event having been deposited as ATCC Accession Number 209030.

31. The maize plant of claim 30, wherein said second maize plant is an inbred.

32. The maize plant of claim 30, wherein said third maize plant is a hybrid.

33. The maize plant of claim 30, wherein the transformation event is GA21.

34. A glyphosate resistant, crossed fertile transgenic maize plant prepared according to the method comprising:
(i) obtaining a fertile transgenic maize plant comprising a chromosomally integrated expression cassette comprising (a) a modified maize EPSPS gene encoding an EPSPS protein having isoleucine at position 102 and serine at position 106 and (b) a promoter active in maize operably linked to said EPSPS gene; and
(ii) crossing said fertile transgenic maize plant with a second maize plant lacking said expression cassette to obtain a third maize plant comprising said expression cassette;
wherein said modified EPSPS gene is inherited through a female parent, and wherein said fertile transgenic maize plant comprises a transformation event selected from the group consisting of GA21, seed comprising said GA21 transformation event having been deposited as ATCC Accession Number 209033, FI117, seed comprising said FI117 transformation event having been deposited as ATCC Accession Number 209031, GG25, seed comprising said GG25 transformation event having been deposited as ATCC Accession Number 209032, and GJ11, seed comprising said GJ11 transformation event having been deposited as ATCC Accession Number 209030.

35. The maize plant of claim 34, wherein said second maize plant is an inbred.

36. The maize plant of claim 34, wherein said third maize plant is a hybrid.

37. The maize plant of claim 34, wherein the transformation event is GA21.

38. A glyphosate resistant, crossed fertile transgenic maize plant prepared according to the method comprising:
(i) obtaining a fertile transgenic maize plant comprising a chromosomally integrated expression cassette comprising (a) a modified maize EPSPS gene encoding an EPSPS protein having isoleucine at position 102 and serine at position 106 and (b) a promoter active in maize operably linked to said EPSPS gene; and
(ii) crossing said fertile transgenic maize plant with a second maize plant lacking said expression cassette to obtain a third maize plant comprising said expression cassette;
wherein said modified EPSPS gene is inherited through a male parent, and wherein said fertile transgenic maize plant comprises a transformation event selected from the group consisting of GA21, seed comprising said GA21 transformation event having been deposited as ATCC Accession Number 209033, FI117, seed comprising said FI117 transformation event having been deposited as ATCC Accession Number 209031, GG25, seed comprising said GG25 transformation event having been deposited as ATCC Accession Number 209032, and GJ11, seed comprising said GJ11 transformation event having been deposited as ATCC Accession Number 209030.

39. The maize plant of claim 38, wherein said second maize plant is an inbred.

40. The maize plant of claim 38, wherein said third maize plant is a hybrid.

41. The maize plant of claim 38, wherein the transformation event is GA21.

42. A glyphosate resistant, crossed fertile transgenic maize plant prepared according to the method comprising:
(i) obtaining a fertile transgenic maize plant comprising a chromosomally integrated expression cassette comprising (a) a modified maize EPSPS gene encoding an EPSPS protein having isoleucine at position 102 and serine at position 106 and (b) a promoter active in maize operably linked to said EPSPS gene;
(ii) crossing said fertile transgenic maize plant with a second maize plant to obtain a third maize plant comprising said expression cassette; and
(iii) backcrossing said third maize plant to obtain a backcrossed fertile transgenic maize plant;
wherein said modified EPSPS gene is inherited through a female parent, and wherein said fertile transgenic maize plant comprises a transformation event selected from the group consisting of GA21, seed comprising said GA21 transformation event having been deposited as ATCC Accession Number 209033, FI117, seed comprising said FI117 transformation event having been deposited as ATCC Accession Number 209031, GG25, seed comprising said GG25 transformation event having been deposited as ATCC Accession Number 209032, and GJ11, seed comprising said GJ11 transformation event having been deposited as ATCC Accession Number 209030.

43. The maize plant of claim 42, wherein said second maize plant is an inbred.

44. The maize plant of claim 42, wherein said third maize plant is a hybrid.

45. The maize plant of claim 42, wherein the transformation event is GA21.

46. A glyphosate resistant, hybrid maize plant comprising a chromosomally integrated expression cassette comprising (a) a modified maize EPSPS gene encoding an EPSPS protein having isoleucine at position 102 and serine at position 106 and (b) a promoter active in maize operably linked to said EPSPS gene, wherein said hybrid maize plant comprises a transformation event selected from the group consisting of GA21, seed comprising said GA21 transformation event having been deposited as ATCC Accession Number 209033, FI117, seed comprising said FI117 transformation event having been deposited as ATCC Accession Number 209031, GG25, seed comprising said GG25 transformation event having been deposited as ATCC Accession Number 209032, and GJ11, seed comprising said GJ11 transformation event having been deposited as ATCC Accession Number 209030.

47. The maize plant of claim 46, wherein said promoter is selected from the group consisting of a rice actin promoter, a maize histone promoter and a fused CaMV 35S-Arabidopsis histone promoter.

48. The maize plant of claim 46, wherein the transformation event is GA21.

49. The maize plant of claim 46, wherein the transformation event is FI117.

50. A glyphosate resistant, hybrid, transgenic maize plant prepared according to the method comprising crossing a first and second inbred maize plant, wherein one of said first and second inbred maize plants comprises a chromosomally integrated expression cassette comprising (a) a modified maize EPSPS gene encoding an EPSPS protein having isoleucine at position 102 and serine at position 106 and (b) a promoter active in maize operably linked to said EPSPS gene, wherein said hybrid transgenic maize plant comprises a transformation event selected from the group consisting of GA21, seed comprising said GA21 transformation event having been deposited as ATCC Accession Number 209033, FI117, seed comprising said FI117 transformation event having been deposited as ATCC Accession Number 209031, GG25, seed comprising said GG25 transformation event having been deposited as ATCC Accession Number 209032, and GJ11, seed comprising said GJ11 transformation event having been deposited as ATCC Accession Number 209030.

51. The maize plant of claim 50, wherein said promoter is selected from the group consisting of a rice actin promoter, a maize histone promoter and a fused CaMV 35S-Arabidopsis histone promoter.

52. The maize plant of claim 50, wherein the transformation event is GA21.

53. The maize plant of claim 50, wherein the transformation event is FI117.

54. A glyphosate resistant, crossed fertile transgenic maize plant prepared by a process comprising:
  (i) obtaining a fertile transgenic maize plant comprising a chromosomally integrated expression cassette comprising (a) a modified maize EPSPS gene encoding an EPSPS protein having isoleucine at position 102 and serine at position 106 and (b) a promoter active in maize operably linked to said EPSPS gene;
  (ii) crossing said fertile transgenic maize plant with a second maize plant to obtain a third maize plant comprising said expression cassette; and
  (iii) crossing said third fertile transgenic maize plant with a fourth maize plant to obtain a fifth transgenic maize plant comprising said expression cassette,
wherein said fertile transgenic maize plant comprises a transformation event selected from the group consisting of GA21, seed comprising said GA21 transformation event having been deposited as ATCC Accession Number 209033, FI117, seed comprising said FI117 transformation event having been deposited as ATCC Accession Number 209031, GG25, seed comprising said GG25 transformation event having been deposited as ATCC Accession Number 209032, and GJ11, seed comprising said GJ11 transformation event having been deposited as ATCC Accession Number 209030.

55. The maize plant of claim 54, wherein said second and fourth maize plants have the same genotype.

56. The maize plant of claim 54, wherein said second and fourth maize plants have different genotypes.

57. Seed of a fertile, transgenic maize plant, said seed comprising a chromosomally integrated expression cassette comprising (a) a modified maize EPSPS gene encoding an EPSPS protein having isoleucine at position 102 and serine at position 106 and (b) a promoter active in maize operably linked to said EPSPS gene, said seed prepared by a process comprising the steps of:
  (i) obtaining a parental fertile, transgenic maize plant comprising a chromosomally integrated expression cassette comprising (a) a modified maize EPSPS gene encoding an EPSPS protein having isoleucine at position 102 and serine at position 106 and (b) a promoter active in maize operably linked to said EPSPS gene;
  (ii) breeding said parental plant with a second fertile maize plant to produce a plurality of progeny fertile, transgenic maize plants, said progeny maize plants including plants that express a chromosomally integrated expression cassette comprising (a) a modified maize EPSPS gene encoding an EPSPS protein having isoleucine at position 102 and serine at position 106 and (b) a promoter active in maize operably linked to said EPSPS gene;
  (iii) selecting from said progeny maize plants a plant having resistance to glyphosate; and
  (iv) obtaining seed from said selected progeny maize plant,
wherein said parent fertile transgenic maize plant comprises a transformation event selected from the group consisting of GA21, seed comprising said GA21 transformation event having been deposited as ATCC Accession Number 209033, FI117, seed comprising said FI117 transformation event having been deposited as ATCC Accession Number 209031, GG25, seed comprising said GG25 transformation event having been deposited as ATCC Accession Number 209032, and GJ11, seed comprising said GJ11 transformation event having been deposited as ATCC Accession Number 209030.

58. The seed of claim 57, wherein the progeny maize plants are two generations removed from the parental transgenic maize plant.

59. The seed of claim 57, wherein the progeny maize plants having resistance to glyphosate are selected by testing plants for resistance to glyphosate at an application rate of 1×.

60. The seed of claim 57, wherein the progeny maize plants having resistance to glyphosate are selected by testing plants for resistance to glyphosate at an application rate of 4×.

61. The seed of claim 57, wherein said second fertile maize plant is a non-transgenic maize plant.

62. The seed of claim 57, wherein said second fertile maize plant is pollinated with pollen from a male parental transgenic maize plant.

63. The seed of claim 57, wherein said parental maize plant is pollinated with pollen from said second fertile maize plant and wherein said parental maize plant is a female parental transgenic maize plant.

* * * * *

UNITED STATES PATENT AND TRADEMARK OFFICE
CERTIFICATE OF CORRECTION

PATENT NO. : 6,040,497
DATED : March 21, 2000
INVENTOR(S) : Michael Spencer, Rita Mumm, and Jeff Gwyn It is certified that error appears in the above-identified patent and that said Letters Patent is hereby corrected as shown below:

At Column 63, line 1, please delete the entire text of claim 29 and insert therefor:
-- The inbred maize plant of claim 26, wherein the transformation event is FI117 --.

Signed and Sealed this

Sixth Day of February, 2001

Attest:

Q. TODD DICKINSON

Attesting Officer

Director of Patents and Trademarks

UNITED STATES PATENT AND TRADEMARK OFFICE
CERTIFICATE OF CORRECTION

| | | |
|---|---|---|
| PATENT NO. | : 6,040,497 | Page 1 of 1 |
| APPLICATION NO. | : 08/832078 | |
| DATED | : March 21, 2000 | |
| INVENTOR(S) | : Michael Spencer et al. | |

It is certified that error appears in the above-identified patent and that said Letters Patent is hereby corrected as shown below:

Title Page

Item [75] Inventors should read --Michael Spencer, Mystic, Connecticut (US); Rita Mumm, Tolono, IL (US); Jeff Gwyn, Mahomet, IL (US); Rick DeRose, Evry (FR); Georges Freyssinet, Saint Cyr au Mont d' OR (FR); Michel Lebrun, Lyons (FR); Bernard Leroux, Raleigh, NC (US); Alain Sailland, Lyons (FR)--.

Signed and Sealed this

Twenty-seventh Day of March, 2007

JON W. DUDAS
*Director of the United States Patent and Trademark Office*

SEQUENCE LISTING

<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic Primer

<400> SEQUENCE: 1
acgtacgacg accacaggat g                                              21

<210> SEQ ID NO 2

-continued

```
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
gcaagaccgg caacaggatt c                                                   21

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 3
tttggctctt ggggatgtg                                                      19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 4
ttacgctagt ctcggtccat                                                     20

<210> SEQ ID NO 5
<211> LENGTH: 570
<212> TYPE: PRT
<213> ORGANISM: Artificial Sequence
<220> FEATURE:
<223> OTHER INFORMATION: Description of Artificial Sequence:  Synthetic
      Primer

<400> SEQUENCE: 5

Met Ala Ser Ile Ser Ser Val Ala Thr Val Ser Arg Thr Ala Pro
 1               5                  10                  15

Ala Gln Ala Asn Met Val Ala Pro Phe Thr Gly Leu Lys Ser Asn Ala
                20                  25                  30

Ala Phe Pro Thr Thr Lys Lys Ala Asn Asp Phe Ser Thr Leu Pro Ser
            35                  40                  45

Asn Gly Gly Gly Arg Val Gln Cys Met Gln Val Trp Pro Ala Tyr Gly
        50                  55                  60

Asn Lys Lys Phe Glu Thr Leu Ser Tyr Leu Pro Pro Leu Ser Met Ala
    65                  70                  75                  80

Pro Thr Val Met Met Ala Ser Ser Ala Thr Ala Val Ala Pro Phe Gln
                85                  90                  95

Gly Leu Lys Ser Thr Ala Ser Leu Pro Val Ala Arg Arg Ser Ser Arg
                100                 105                 110

Ser Leu Gly Asn Val Ser Asn Gly Gly Arg Ile Arg Cys Met Ala Gly
            115                 120                 125

Ala Glu Glu Ile Val Leu Gln Pro Ile Lys Glu Ile Ser Gly Thr Val
        130                 135                 140

Lys Leu Pro Gly Ser Lys Ser Leu Ser Asn Arg Ile Leu Leu Ile Ala
    145                 150                 155                 160

Ala Leu Ser Glu Gly Thr Thr Val Val Asp Asn Leu Leu Asn Ser Glu
```

```
                    165                 170                 175
Asp Val His Tyr Met Leu Gly Ala Leu Arg Thr Leu Gly Leu Ser Val
                180                 185                 190
Glu Ala Asp Lys Ala Ala Lys Arg Ala Val Val Gly Cys Gly Gly
            195                 200                 205
Lys Phe Pro Val Glu Asp Ala Lys Glu Val Gln Leu Phe Leu Gly
        210                 215                 220
Asn Ala Gly Ile Ala Met Arg Ser Leu Thr Ala Ala Val Thr Ala Ala
225                 230                 235                 240
Gly Gly Asn Ala Thr Tyr Val Leu Asp Gly Val Pro Arg Met Arg Glu
                245                 250                 255
Arg Pro Ile Gly Asp Leu Val Val Gly Leu Lys Gln Leu Gly Ala Asp
            260                 265                 270
Val Asp Cys Phe Leu Gly Thr Asp Cys Pro Val Arg Val Asn Gly
        275                 280                 285
Ile Gly Gly Leu Pro Gly Gly Lys Val Lys Leu Ser Gly Ser Ile Ser
290                 295                 300
Ser Gln Tyr Leu Ser Ala Leu Leu Met Ala Ala Pro Leu Ala Leu Gly
305                 310                 315                 320
Asp Val Glu Ile Glu Ile Ile Asp Lys Leu Ile Ser Ile Pro Tyr Val
                325                 330                 335
Glu Met Thr Leu Arg Leu Met Glu Arg Phe Gly Val Lys Ala Glu His
            340                 345                 350
Ser Asp Ser Trp Asp Arg Phe Tyr Ile Lys Gly Gly Gln Lys Tyr Lys
        355                 360                 365
Ser Pro Lys Asn Ala Tyr Val Glu Gly Asp Ala Ser Ala Ser Tyr
    370                 375                 380
Phe Leu Ala Gly Ala Ala Ile Thr Gly Thr Val Thr Val Glu Gly
385                 390                 395                 400
Cys Gly Thr Thr Ser Leu Gln Gly Asp Val Lys Phe Ala Glu Val Leu
                405                 410                 415
Glu Met Met Gly Ala Lys Val Thr Trp Thr Glu Thr Ser Val Thr Val
            420                 425                 430
Thr Gly Pro Pro Arg Glu Pro Phe Gly Arg Lys His Leu Lys Ala Ile
        435                 440                 445
Asp Val Asn Met Asn Lys Met Pro Asp Val Ala Met Thr Leu Ala Val
    450                 455                 460
Val Ala Leu Phe Ala Asp Gly Pro Thr Ala Ile Arg Asp Val Ala Ser
465                 470                 475                 480
Trp Arg Val Lys Glu Thr Glu Arg Met Val Ala Ile Arg Thr Glu Leu
                485                 490                 495
Thr Lys Leu Gly Ala Ser Val Glu Glu Gly Pro Asp Tyr Cys Ile Ile
            500                 505                 510
Thr Pro Pro Glu Lys Leu Asn Val Thr Ala Ile Asp Thr Tyr Asp Asp
        515                 520                 525
His Arg Met Ala Met Ala Phe Ser Leu Ala Ala Cys Ala Glu Val Pro
    530                 535                 540
Val Thr Ile Arg Asp Pro Gly Cys Thr Arg Lys Thr Phe Pro Asp Tyr
545                 550                 555                 560
Phe Asp Val Leu Ser Thr Phe Val Lys Asn
                565                 570
```